(12) United States Patent
Curran et al.

(10) Patent No.: US 9,080,208 B2
(45) Date of Patent: *Jul. 14, 2015

(54) COMPOSITE LIQUID CELLS

(71) Applicant: GenCell Biosystems Ltd., Raheen (IE)

(72) Inventors: Kieran Curran, Ballyclough (IE); Paul Fleming, Athy (IE); Séamus Gillhooley, Athenry (IE); Micheál Keane, Tubber (IE); Inga Rosca, Castletroy (IE); Patrick Tuohy, Roscrea (IE)

(73) Assignee: GenCell Biosystems Ltd., Raheen, County Limerick (IE)

( * ) Notice: Subject to any disclaimer, the term of this patent is extended or adjusted under 35 U.S.C. 154(b) by 68 days.

This patent is subject to a terminal disclaimer.

(21) Appl. No.: 13/895,930

(22) Filed: May 16, 2013

(65) Prior Publication Data

US 2013/0280726 A1 Oct. 24, 2013

Related U.S. Application Data

(63) Continuation of application No. 13/147,679, filed as application No. PCT/IE2011/000040 on Jul. 22, 2011, now Pat. No. 8,465,707.

(60) Provisional application No. 61/344,434, filed on Jul. 22, 2010, provisional application No. 61/470,515, filed on Apr. 1, 2011, provisional application No. 61/470,520, filed on Apr. 1, 2011.

(51) Int. Cl.
*B01L 3/02* (2006.01)
*C12Q 1/68* (2006.01)
(Continued)

(52) U.S. Cl.
CPC ............ *C12Q 1/686* (2013.01); *B01F 13/0071* (2013.01); *B01L 3/502784* (2013.01);
(Continued)

(58) Field of Classification Search
CPC .......... G01N 35/1002; G01N 35/1009; G01N 2035/1032; G01N 1/38; B01L 3/0262; B01L 2200/0673; B01F 13/10069; B01F 13/0071

USPC ......... 422/509, 501, 504, 514, 515, 518–519; 436/180, 43, 54, 174, 176, 179

See application file for complete search history.

(56) References Cited

U.S. PATENT DOCUMENTS 5,221,518 A 6/1993 Mills
(Continued)

FOREIGN PATENT DOCUMENTS

| CN | 101028607 A | 9/2007 |
|---|---|---|
| EP | 1019496 B1 | 7/2000 |

(Continued)

OTHER PUBLICATIONS

Mastrobattista et al., "High-Throughput Screening of Enzyme Libraries: In Vitro Evolution of a ?-Galactosidase by Fluorescence-Activated Sorting of Double Emulsions," Chemistry & Biology 12:1291-1300, Dec. 2005.
(Continued)

*Primary Examiner* — Brian R Gordon
(74) *Attorney, Agent, or Firm* — Bret E. Field; Bozicevic, Field & Francis LLP

(57) ABSTRACT

A sample handling method may include drawing an encapsulating liquid from an encapsulating-liquid input; discharging the drawn encapsulating liquid (a) onto a free surface of a carrier liquid in a carrier-liquid conduit comprising a stabilization feature and (b) proximate to the stabilization feature, the encapsulating liquid being immiscible with the carrier liquid, so that the discharged encapsulating liquid does not mix with the carrier liquid, floats on top of the carrier liquid, and is immobilized by the stabilization feature; drawing a sample liquid from a sample-liquid input; and discharging the drawn sample liquid, the sample liquid being immiscible with the encapsulating liquid and with the carrier liquid, so that the sample liquid does not mix with the encapsulating liquid or with the carrier liquid.

16 Claims, 42 Drawing Sheets

(51) Int. Cl.
*B01F 13/00* (2006.01)
*B01L 3/00* (2006.01)
*B01L 7/00* (2006.01)

(52) U.S. Cl.
CPC ............ *B01L7/525* (2013.01); *B01L 2200/027* (2013.01); *B01L 2200/0647* (2013.01); *B01L 2200/0668* (2013.01); *B01L 2200/0673* (2013.01); *B01L 2300/089* (2013.01); *B01L 2300/0816* (2013.01); *B01L 2300/0819* (2013.01); *B01L 2300/0864* (2013.01); *B01L 2300/0867* (2013.01); *B01L 2400/0406* (2013.01); *B01L 2400/0409* (2013.01); *B01L 2400/0415* (2013.01); *B01L 2400/0475* (2013.01); *B01L 2400/0487* (2013.01); *B01L 2400/0633* (2013.01); *B01L 2400/086* (2013.01); *Y10T 436/11* (2015.01); *Y10T 436/119163* (2015.01); *Y10T 436/25* (2015.01); *Y10T 436/2525* (2015.01); *Y10T 436/2575* (2015.01); *Y10T 436/25625* (2015.01)

(56) References Cited

U.S. PATENT DOCUMENTS

| | | | |
|---|---|---|---|
| 5,408,306 A * | 4/1995 | Anderson | 356/36 |
| 5,505,877 A | 4/1996 | Krivohlavek | |
| 5,639,426 A * | 6/1997 | Kerr et al. | 422/501 |
| 5,980,936 A | 11/1999 | Krafft et al. | |
| 6,136,609 A * | 10/2000 | Sato et al. | 436/180 |
| 6,284,546 B1 * | 9/2001 | Bryning et al. | 436/172 |
| 6,326,211 B1 * | 12/2001 | Anderson et al. | 436/177 |
| 7,129,091 B2 | 10/2006 | Ismagilov et al. | |
| 7,138,233 B2 | 11/2006 | Griffiths et al. | |
| 7,238,323 B2 | 7/2007 | Knapp et al. | |
| 7,244,396 B2 * | 7/2007 | Chait et al. | 422/501 |
| 7,244,567 B2 | 7/2007 | Chen et al. | |
| 7,252,943 B2 | 8/2007 | Griffiths et al. | |
| 7,323,305 B2 | 1/2008 | Leamon et al. | |
| 7,329,545 B2 * | 2/2008 | Pamula et al. | 436/53 |
| 7,439,014 B2 | 10/2008 | Pamula et al. | |
| 7,582,446 B2 | 9/2009 | Griffiths et al. | |
| 7,638,276 B2 | 12/2009 | Griffiths et al. | |
| 7,759,132 B2 * | 7/2010 | Pollack et al. | 436/180 |
| 7,776,927 B2 | 8/2010 | Chu et al. | |
| 7,842,457 B2 | 11/2010 | Berka et al. | |
| 7,901,939 B2 | 3/2011 | Ismagliov et al. | |
| 7,915,013 B2 | 3/2011 | Cho et al. | |
| 7,943,348 B2 | 5/2011 | Cho et al. | |
| 8,029,744 B2 * | 10/2011 | Noda et al. | 422/504 |
| 8,128,798 B2 * | 3/2012 | Adachi et al. | 204/600 |
| 8,158,359 B2 | 4/2012 | Leamon et al. | |
| 8,252,539 B2 * | 8/2012 | Quake et al. | 435/6.12 |
| 8,263,023 B2 * | 9/2012 | Le Vot et al. | 422/503 |
| 8,273,573 B2 | 9/2012 | Ismagilov et al. | |
| 8,304,193 B2 | 11/2012 | Ismagilov et al. | |
| 8,329,407 B2 | 12/2012 | Ismagilov et al. | |
| 8,367,326 B2 | 2/2013 | Griffiths et al. | |
| 8,709,762 B2 | 4/2014 | Hindson | |
| 8,748,102 B2 | 6/2014 | Berka et al. | |
| 8,765,380 B2 | 7/2014 | Berka et al. | |
| 8,790,876 B2 | 7/2014 | Leamon et al. | |
| 2005/0087122 A1 | 4/2005 | Ismagliov et al. | |
| 2006/0246224 A1 | 11/2006 | Neitzel | |
| 2007/0037294 A1 * | 2/2007 | Pamula et al. | 436/180 |
| 2007/0042367 A1 | 2/2007 | Tao et al. | |
| 2007/0243634 A1 | 10/2007 | Pamula et al. | |
| 2007/0275415 A1 | 11/2007 | Srinivasan et al. | |
| 2009/0023189 A1 | 1/2009 | Lau et al. | |
| 2009/0131543 A1 | 5/2009 | Weitz et al. | |
| 2010/0015614 A1 | 1/2010 | Beer et al. | |
| 2010/0022414 A1 | 1/2010 | Link et al. | |
| 2010/0105112 A1 | 4/2010 | Holtze et al. | |
| 2010/0173394 A1 | 7/2010 | Colston, Jr. et al. | |
| 2011/0171748 A1 * | 7/2011 | Cox et al. | 436/180 |
| 2012/0028342 A1 * | 2/2012 | Ismagilov et al. | 435/283.1 |
| 2012/0208241 A1 | 8/2012 | Link | |
| 2012/0276543 A1 * | 11/2012 | Quake et al. | 435/6.12 |
| 2012/0276544 A1 * | 11/2012 | Quake et al. | 435/6.12 |
| 2012/0298205 A1 * | 11/2012 | Schertzer et al. | 137/1 |
| 2013/0109575 A1 | 5/2013 | Kleinschmidt et al. | |
| 2013/0190189 A1 | 7/2013 | Griffiths et al. | |
| 2014/0113300 A1 | 4/2014 | Samuels | |
| 2014/0162885 A1 | 6/2014 | Berka et al. | |
| 2014/0199730 A1 | 7/2014 | Agresti et al. | |
| 2014/0199731 A1 | 7/2014 | Agresti et al. | |

FOREIGN PATENT DOCUMENTS

| | | |
|---|---|---|
| EP | 1053784 A2 | 11/2000 |
| EP | 0892035 B1 | 10/2004 |
| EP | 1485204 B1 | 2/2006 |
| EP | 1496120 B1 | 3/2007 |
| EP | 1482036 B1 | 10/2007 |
| EP | 1508044 B1 | 9/2010 |
| EP | 1801214 B1 | 11/2010 |
| EP | 2258846 A2 | 12/2010 |
| EP | 2277337 A2 | 1/2011 |
| EP | 2248578 B1 | 6/2012 |
| EP | 1908832 B1 | 12/2012 |
| EP | 2703497 A1 | 3/2014 |
| JP | 2008538077 A | 10/2008 |
| JP | 2009534653 A | 9/2009 |
| JP | 2010503516 A | 2/2010 |
| WO | 93/03151 A1 | 2/1993 |
| WO | 94/08759 A1 | 4/1994 |
| WO | 2004038363 A2 | 5/2004 |
| WO | 2005002730 A1 | 1/2005 |
| WO | 2007/120240 A2 | 10/2007 |
| WO | 2008/130623 A1 | 10/2008 |
| WO | 2008144288 A1 | 11/2008 |
| WO | 2009/061372 A1 | 5/2009 |
| WO | 2009/134395 A2 | 11/2009 |
| WO | 2009/149257 A1 | 12/2009 |
| WO | 2010/104604 A1 | 9/2010 |
| WO | 2010/121307 A1 | 10/2010 |
| WO | 2013192351 A1 | 12/2013 |
| WO | 2014039587 A1 | 3/2014 |
| WO | 2014093714 A1 | 6/2014 |

OTHER PUBLICATIONS

Utada et al., "Monodisperse Double Emulsions Generated from a Microcapillary Device," Science 308:537-541, Apr. 2005.
Wu et al., "A double-emulsion microfluidic platform for in vitro green fluorescent protein expression," J. Micromech. Microeng. 21:054032 (1-7), 2011.
International Search Report and Written Opinion for PCT/IE2011/000040, dated Apr. 3, 2012.
Examination Report for Australian Application No. 2011281183 dated Feb. 28, 2014.
Lee et al. "On-Chip Procedures for Magnetic Particle-Based Assay in Droplets", 16th International Conference on Miniaturized Systems for Chemistry and Life Sciences, Oct. 28-Nov. 1, 2012, Okinawa, Japan, pp. 347-349.
Lehmann et al. "A Lab-on-a-Chip using magnetic droplets", NSTI-Nanotech 2006, vol. 2, 2006, pp. 477-480.
Tawfik et al. "Man-made cell-like compartments for molecular evolution", Nature Biotechnology, vol. 16, Jul. 1998 652-656.

* cited by examiner

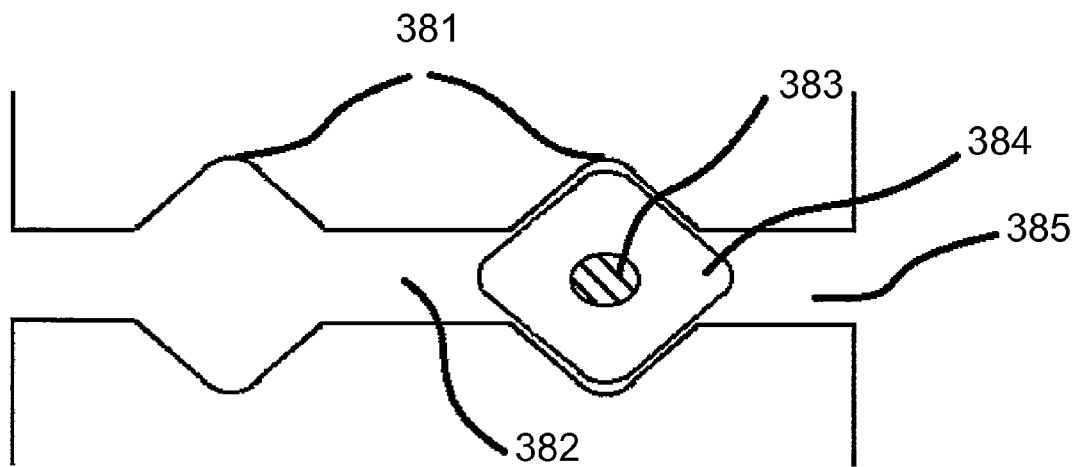
FIG. 31
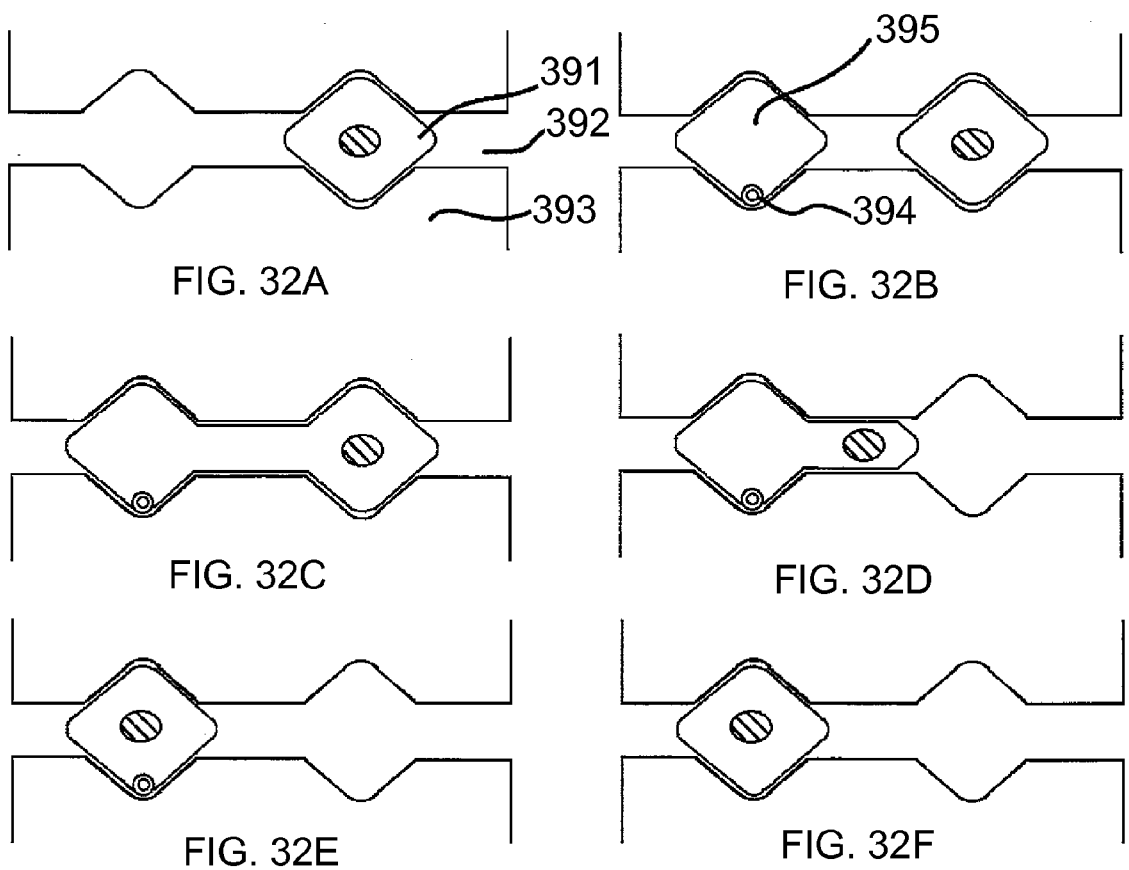
FIG. 32A  FIG. 32B
FIG. 32C  FIG. 32D
FIG. 32E  FIG. 32F

COMPOSITE LIQUID CELLS

CROSS-REFERENCE TO RELATED APPLICATIONS

This is a continuation application of U.S. patent application Ser. No. 13/147,679 filed on Aug. 3, 2011, which claims the benefit of the national stage of International application Ser. No. PCT/IE2011/000040, filed Jul. 22, 2011, which claims the benefit of U.S. provisional application Ser. Nos. 61/344,434, filed Jul. 22, 2010, 61/470,515, filed Apr. 1, 2011, and 61/470,520, filed Apr. 1, 2011, each of which is hereby incorporated herein by reference.

BACKGROUND

Currently the processing of biochemistry samples has a number of key drawbacks. These include the volume size—resulting in high reagent costs; high consumable costs; and labour-intensive protocols and processes which are highly susceptible to cross-contamination. For these reasons complete control and isolation of each individual sample within the biochemistry process cannot currently be ensured.

For a number of biochemistry process applications—sequence bead preparation, pyrosequencing, nucleic acid ligation, and polymerase chain reaction—and not limited to these, the limitations of volume size, chemistry cost, labour cost, and the reaction efficiency are evident.

Sequence bead preparation is a process by which small beads are coated in an application-specific chemistry. For example in DNA replication, the beads are coated initially with DNA primers in advance of the amplification process. Even for today's state-of-the-art sequencers a relatively high local concentration of the target molecule is required to sequence accurately. Current estimates for a typical protocol estimate that only 80% of the beads processed are sufficiently coated to ensure accurate sequencing. Therefore to ensure a relatively high concentration of the target sample a large number of beads must be used for statistical accuracy. Furthermore, the transferral of even coated beads from one well to another inevitably leads to losses of both the beads and the suspended fluid. This is a result of dead volumes and inefficiencies inherent in today's pipetting and liquid handling systems. This biochemistry process is generally performed in 96 or 384 static well plates with typical volumes ranging from 10 microliters to 200 microliters.

Another biochemistry process, pyrosequencing, mixes a relatively high concentration of nucleic acid with primer-coated beads. The nucleic acids attach and form a clonal colony on the beads. This is then amplified using emulsion-based PCR. The sequencing machine contains a large number of picoliter-volume wells that are large enough for a single bead along with the relevant enzymes required for sequencing. Pyrosequencing uses the luciferase enzyme to generate light as read-out, and the sequencing machine takes a picture of the wells for every added nucleotide. One of the key difficulties in this process is the efficient coating of the beads with primers. A percentage of beads using current technologies are not properly coated with primer chemistry, resulting in poorer reaction efficiencies. Using today's technologies to improve the coating efficiencies of the beads would require an unsustainable increase in reagent cost.

Within nucleic acid ligation similar biochemistry processing issues arise. Nucleic acid ligation has become an important tool in modem molecular biology research for generating recombinant nucleic acid sequences. For example, nucleic acid ligases are used with restriction enzymes to insert nucleic acid fragments, often genes, into plasmids for use in genetic engineering. Nucleic acid ligation is a relatively common technique in molecular biology wherein short strands of DNA may be joined together by the action of an enzyme called ligase at a specific temperature, commonly 16-25° C. depending on the protocol used. To join more than two sequences of short DNA strands together, for example in the construction of a synthetic genetic sequence, it is impossible to combine all the DNA strands and then perform the ligation. This would result in random sequences in which the end of one strand would be joined to the start of an incorrect strand. This incorrect sequence, or orientation, would not be desirable in a synthetically-constructed gene where the order of the genetic code is crucial. To perform the technique correctly pairwise combinations of neighbouring sequences must first be ligatated to yield the correct orientation. These paired synthetic constructs may then be ligated in the correct orientation to yield even longer synthetic constructs. The process involves a large and intricate amount of chemistry processing and manipulation. This can be quite a labour intensive process or if performed using today's liquid handling and results in large consumable costs and suffers from the known dead volume losses of the static well plates and pipette aspirations. Also using today's liquid handling technologies the mixing and control of small volumes is limited by the ability to aspirate and manipulate relatively small volumes. Typical volumes used in nucleic acid ligation are 10-200 microliters with nucleic acid strand lengths between 50-200 base pairs.

Polymerase Chain Reaction (PCR) has been used extensively to amplify targeted DNA and cDNA for many applications in molecular biology. The PCR technique amplifies a single or a few copies of a piece of DNA, generating thousands to billions of copies of a particular DNA sequence. Modem PCR instruments carry out the PCR process in reaction volumes ranging from 10-200 micro-liters. One of the largest obstacles to carrying out PCR in small volumes is the difficulty in manipulating small volumes of the constituent reagents with manual pipettes. The large volume size is a direct result of the poor capability of existing technologies to dispense and mix sub-nanoliter volumes. Furthermore, for the next generation microfluidic technologies based on flowing systems, these are still limited by the starting volume dispensed versus the actual amount of sample required for the biochemistry process. These microfluidic systems are also limited during the biochemistry process to a defined protocol control of the samples. These systems typically rely on microscale fluid channel networks to transport and mix sub-microliter volumes. Some of the major drawbacks of these technologies are: the single use of the microfluidic cards—to prevent contamination—the lack of dynamic control of the each individual sample—transporting and mixing any individual sample at any point in the biochemistry process—and the closed architecture of the system.

In particular, current methods of Digital Polymerase Chain Reaction (dPCR) are performed through the division of an initial sample into multiple smaller volumes samples until one DNA template remains in each subvolume. Counting the number of positive subvolumes which contain DNA, the starting copy number in the original volume can be calculated. Typically, this involves multiple serial dilution steps to generate a sample volume with statistically one DNA target per reaction volume. Statistically a subset of the total volume may be tested to determine the initial copy number, allowing for a reduction in the total number of PCR reactions. However for rare target detection a larger subset of volumes need to be tested to improve the statistical accuracy. This results in a larger number of blank volumes and a larger test volume— resulting in the use of more chemistry, time, instrumentation, sample handling, and processing steps.

Another method of dPCR is whereby an emulsion of the test volume is generated in an oil-based carrier. This method is an effort to reduce the number of instruments required and time required for a result. First, the target sample is diluted and emulsified into small enough volumes with a statistical distribution of less than one copy per droplet, within the carrier oil. This larger volume can then be treated as a single sample volume and processed using PCR protocols. However this method is generally limited to end point detection. Further instrumentation is required in the form of a flow cytometer, thereby being able to detect the target presence per droplet flowing past a sensor. Flow cytometers are low speed; expensive; can require specific fluid mediums and only allow for endpoint detection. The limitations of endpoint detection include the requirement of a post processing step; lower sensitivity; longer time to result; specificity and more instrumentation. A further challenge for emulsion based PCR methods is the stability required and control of each droplet. Droplet merging or splitting introduces further statistical errors into the processing.

Today's pipetting and liquid handling systems are unable to process 100% of the given starting volume. For pipettes both the liquid storage system—static well plates—and the mechanical actuation within the system prevent complete aspiration of the sample. This loss or dead volume in static plates can be accounted for by the surface wetting characteristics and the geometry, neither of which current technologies can account for.

In flowing systems the collection of individual biological samples during or at the end of the biochemistry process is proving to be very challenging for existing technologies. The typical continuous flowing systems comprise of pumps and reservoirs which generally make the easy retrieval of critical fluids, particularly at the microscale, technically difficult. Also, within flowing systems initial priming of the system is time consuming, costly and if done incorrectly leads to a catastrophic failure of the test requiring a retest of the biological sample.

Another drawback to existing biochemistry processing is the inability to automate the biochemistry process for nano-liter and sub-nano-liter volumes. The transport, mixing or retrieval of each individual sample cannot be performed by existing automated technologies.

In more general chemistry processing, such as generic microchemistry, where the manipulation of small amounts of fluid is necessary, one can clearly see the limitations of current technology in the volume waste fluid remaining in the static well plates or within the system. This is a result of current technology's lack of capability to dispense and control smaller volumes demanded by evermore sophisticated molecular biology techniques, and the call for improved efficiencies.

The invention is therefore directed towards providing improved sample handling to overcome at least some of the above problems.

SUMMARY

Devices, systems and methods for making and handling composite liquid cells are disclosed.

BRIEF DESCRIPTION OF THE DRAWINGS

FIG. 31 is a diagram illustrating a simple composite liquid cell network.

FIGS. 32A-32F are diagrams illustrating a transportation method for a composite liquid cell within a composite fluid network.

DETAILED DESCRIPTION

The invention provides in some embodiments systems and methods for the generation of a biological sample within an immiscible fluid cell and positioned on a free surface of a mutually immiscible carrier fluid. This involves generation, and/or location control, and/or movement control, and/or mixing, and/or processing of biological samples within such composite liquid cells (synonymous with "composite fluid cell") and positioned on an immiscible carrier fluid.

The biological sample typically has a density between that of the carrier fluid and the outer fluid of the composite liquid cell. The carrier fluid typically has a density higher than that of the outer fluid of the composite liquid cell.

Typical values of densities for the fluids involved range within the values 1,300 to 2,000 kg/m3 for the carrier fluid, 700 to 990 kg/m3 for the immiscible fluid cell and 900 to 1200 kg/m3 for the biological sample. An example of one such set of operating fluids and densities is outlined herein but is not limited to these; carrier fluid is Fluorinert FC-40 (fluorocarbonated oil) density of approximately 1,900 kg/m3; outer fluid of the composite liquid cell is phenylmethylpolysiloxane (silicone oil) density of approximately 920 kg/m3; and the biological sample is an aqueous based solution of PCR reagents with a density of approximately 1000 kg/m3.

In another embodiment the carrier fluid is a perfluorinated amine oil.

In another embodiment, the encapsulating fluid is a solution of a Phenylmethylpolysiloxane-based oil and a polysorbate additive. The additives have a hydrophilic-lipophilic balance number in the range of 2 to 8. The combined total hydrophilic-lipophilic balance number of the additives is in the range of 2 to 8. Examples of polysorbate additives are SPAN 80, SPAN 65 and Tween 20 but are not limited to these. These additives within the buffer encapsulating fluid range between 0.001% and 10%.

In another embodiment, the target sample is a solid particle suspension in aqueous media and the encapsulating fluid is a Phenylmethylpolysiloxane-based oil, on a carrier fluid which is a fluorocarbon-based oil.

In another embodiment the target sample is an aqueous media-in-Phenylmethylpolysiloxane-based oil and the encapsulating fluid is a Phenylmethylpolysiloxane-based oil, on a carrier fluid which is a fluorocarbon-based oil.

In some embodiments the control surfaces are a hydrophobic material.

A system used for making and manipulating composite liquid cells will typically include a liquid handling system under the control of a controller (such as a programmable computer). The controller is typically programmed to cause the liquid handling system to carry out various steps, with the program steps stored in a nontransitory computer-readable medium.

Generating Composite Liquid Cells

Figure 1A:
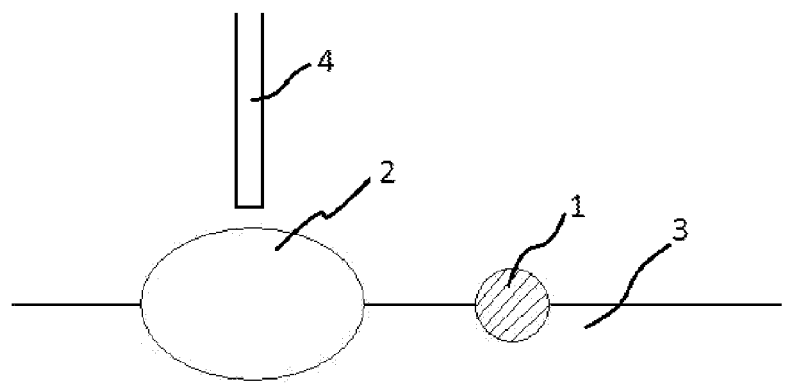
FIGS. 1A and 1B schematically illustrate composite liquid cell generation using electrostatic forces.
Figure 1B:
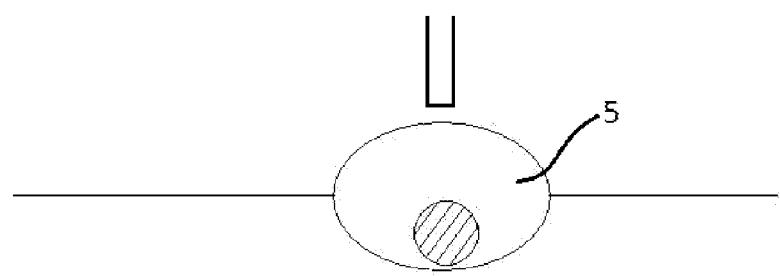

Referring to FIG. 1A, a biological sample 1 and a mutually immiscible fluid cell 2 positioned on a free surface of a mutually immiscible carrier fluid 3 can be combined using a control surface 4. In one embodiment, the control surface 4 uses electrostatic forces to control the location of the immiscible fluid cell 2. The control surface is charged and is brought in close proximity to the immiscible fluid cell, a charge separation will occur. For example the control surface is given a highly positive charge, negatively charged ions within the immiscible fluid cell will separate towards the charged body. The result is a polar charge separation and an attractive force towards the charged body. Referring to FIG. 1B a composite liquid cell 5 is generated.

Figure 2A:
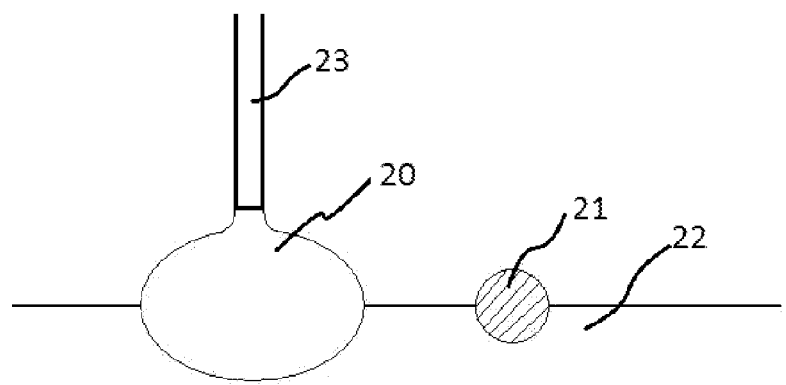
FIGS. 2A and 2B schematically illustrate composite liquid cell generation using the hydrophobic effect.
Figure 2B:
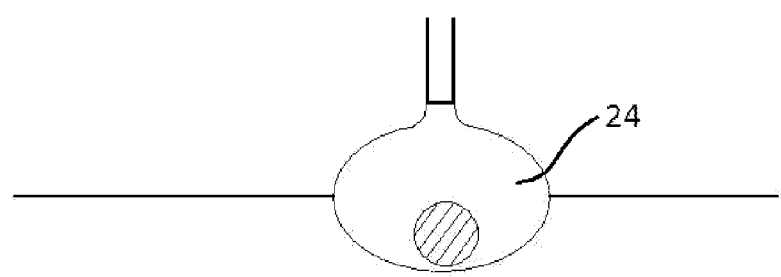

In another embodiment, referring to FIG. 2A a biological sample 21 and a mutually immiscible fluid cell 20 positioned on a free surface of a mutually immiscible carrier fluid 22 can be combined using a control surface 23. The control surface 23 uses the hydrophobic effect to control the location of the immiscible fluid cell 20. Hydrophobic surfaces repel aqueous based media but silicon-based oils readily wet the surfaces permitting control using capillary tension. Bringing the control surface 23 into contact with the immiscible fluid cell 20 will result in a wetting of the surface of the body by the immiscible fluid cell 20. The fluid cell can then be transported to a location on the carrier fluid 22 by translating the control surface 23. Referring to FIG. 2B a composite cell 24 is generated.

Figure 3A:
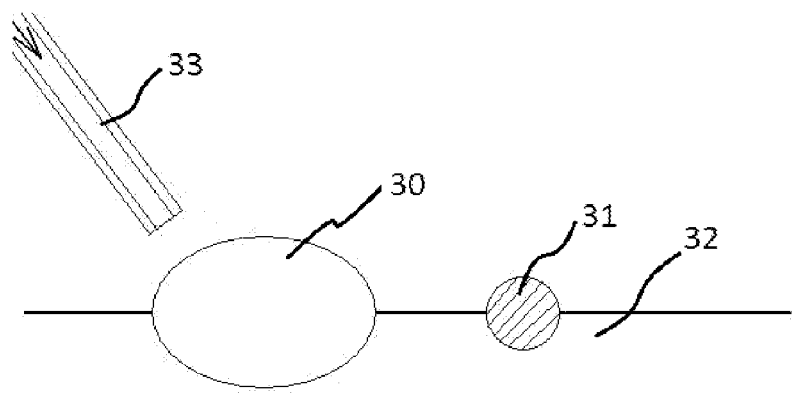
FIGS. 3A and 3B schematically illustrate composite liquid cell generation using directional air control.
Figure 3B:
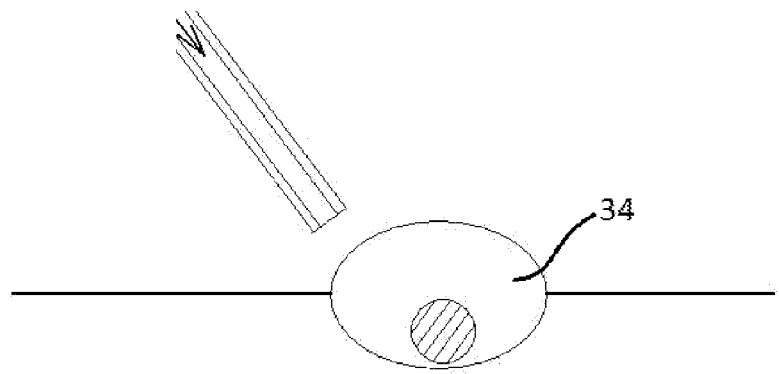

In another embodiment, referring to FIG. 3A a biological sample 31 and a mutually immiscible fluid cell 30 positioned on a free surface of a mutually immiscible carrier fluid 32 can be combined using a directional control tube 33. The directional control tube 33 provides an air jet which when directed to impinge on the immiscible fluid cell 30 generates a drag force larger than the translational resistance, thereby transporting the cell fluid in a controlled manner. Referring to FIG. 3B a composite liquid cell 34 is generated.

Figure 4A:
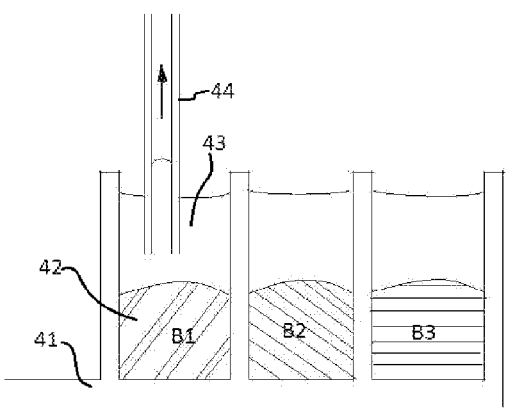
FIGS. 4A-4F schematically illustrate generation of a composite liquid cell using a control tube and variable flow direction.
Figure 4B:
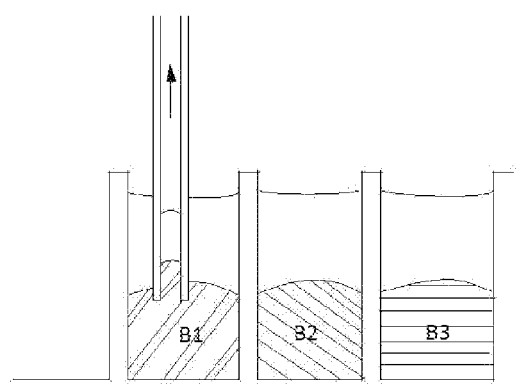
Figure 4C:
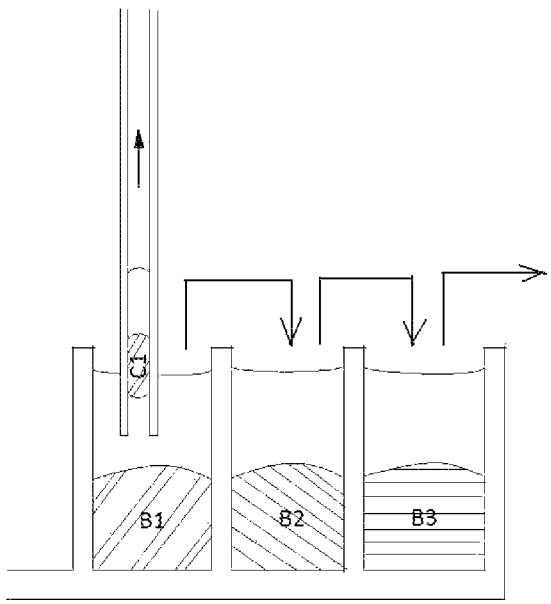
Figure 4D:
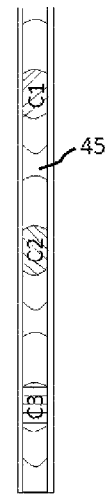
Figure 4E:
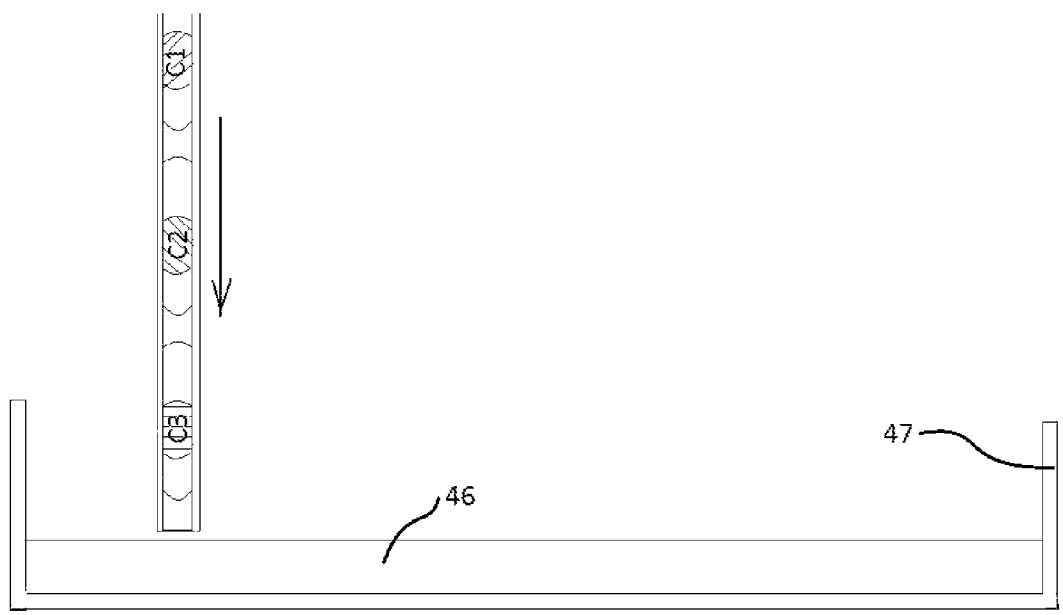
Figure 4F:
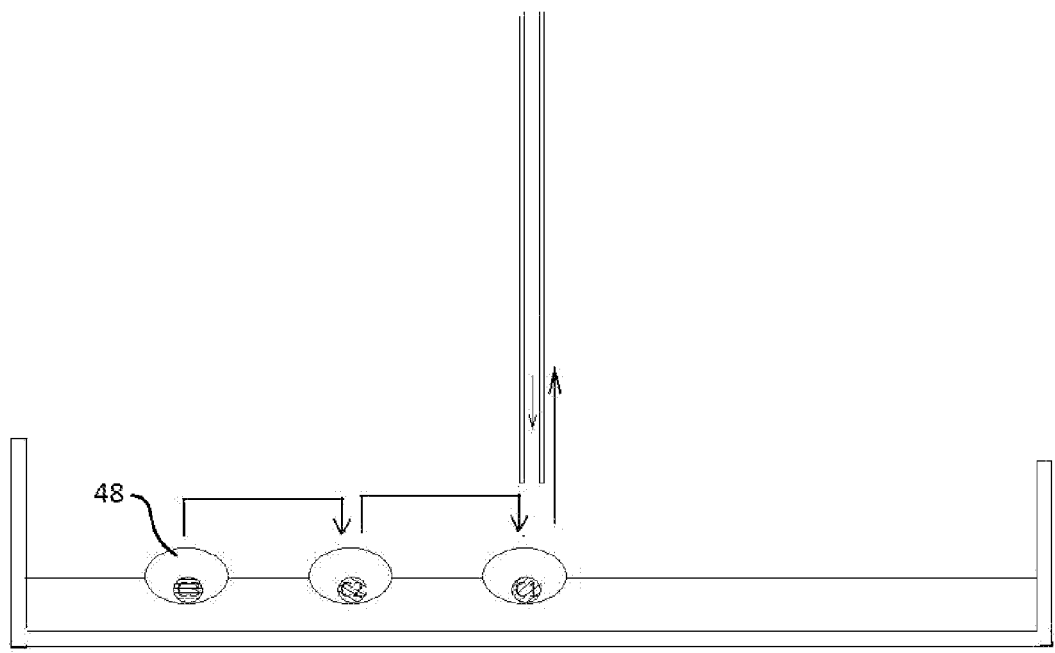

In another embodiment, referring to FIG. 4A composite liquid cells can be generated using the method and system shown. Referring to FIG. 4A a well plate 41 contains biological sample 42 in one or more locations (B1, B2, B3) and is covered by an immiscible fluid 43. A control tube 44 has a controllable pressure across the tube. In this mode of operation a continuous pressure drop is held within the tube, thereby withdrawing the immiscible fluid 43 into the tube when the tube is translated into contact with the immiscible fluid 43. A volume of immiscible fluid 43 is withdrawn into the tube. Referring to FIG. 4B the control tube 44 translates into the biological sample 41 and withdraws a volume of biological sample C1. Referring to FIG. 4C the control tube returns to the immiscible fluid layer withdrawing a volume of immiscible fluid. Following this, the control tube then exits the fluid overlay and withdraws air prior to repeating the procedure at either the same biological sample location or at a new biological sample location. Referring to FIG. 4D the control tube is loaded with biological samples C1, C2, C3, immiscible fluid and an air gap 45 separating the immiscible fluids and biological samples. Referring to FIG. 4E the control tube is positioned over the carrier oil layer 46 housed in a biocompatible container 47. The control tube may either be in contact with or positioned between 0-3 mm above the free surface of the carrier oil 46. The flow direction is reversed in the control tube and immiscible fluid, sample and immiscible fluid are deposited on the free surface of the carrier oil, generating a composite liquid cell. Referring to FIG. 4F upon depositing a complete composite liquid cell 48 the control tube translates to a new position to deposit the next composite liquid cell.

Transporting Composite Liquid Cells

Figure 5:
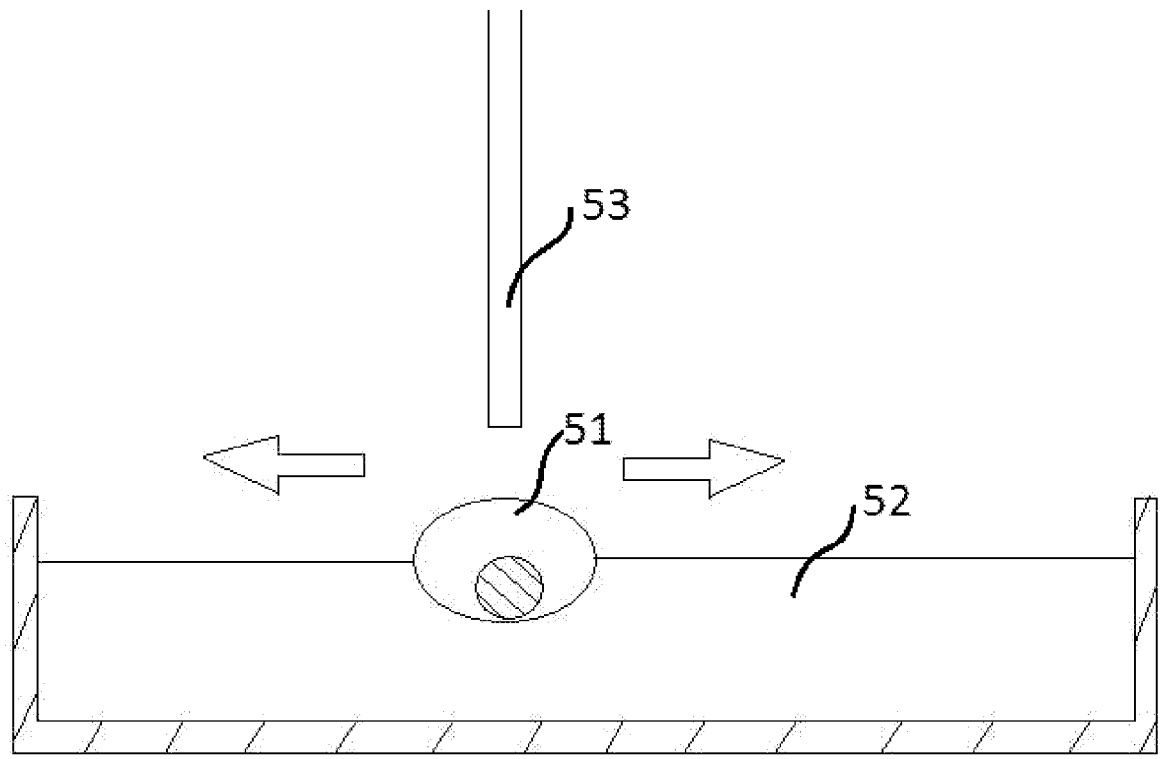
FIG. 5 schematically illustrates control of a composite liquid cell using electrostatic forces.

In another embodiment, referring to FIG. 5 the composite liquid cell 51 is transported on an immiscible carrier fluid 52 using control surface 53. The control surface 53 uses electrostatic forces to control the location of the composite liquid cell 52. The control surface is charged and is brought in close proximity to the outer fluid of the composite liquid cell, a charge separation will occur. For example the control surface is given a highly positive charge, negatively charged ions within the immiscible fluid cell will separate towards the charged body. The result is a polar charge separation and an attractive force towards the charged body. Using this transport motion one or more composite liquid cells can be merged or additional biological samples can be added to a composite liquid cell.

Figures 6A, 6B, 6C:
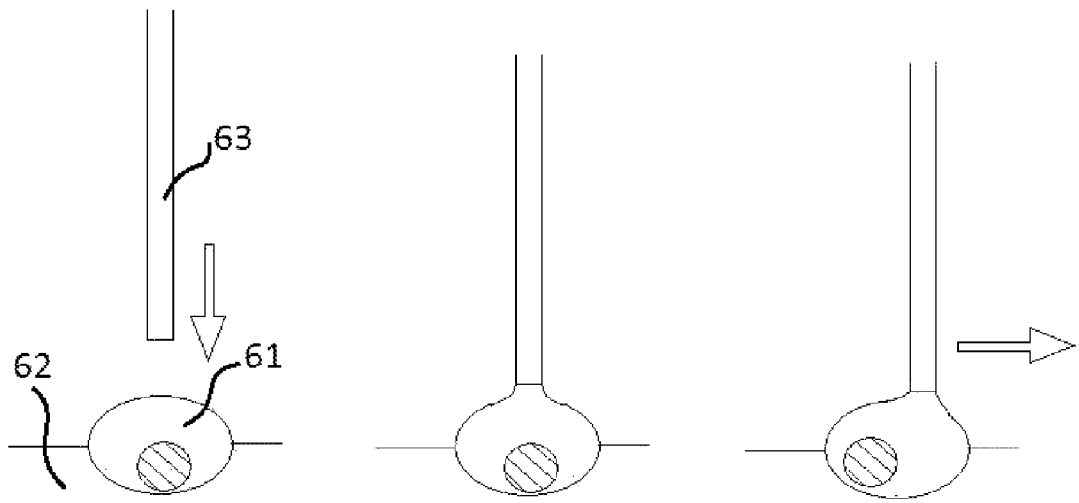
FIGS. 6A-6C schematically illustrate control of a composite liquid cell using the hydrophobic effect.

In another embodiment, referring to FIG. 6A a composite liquid cell 61 positioned on a free surface of a mutually immiscible carrier fluid 62 can be transported using a control surface 63. The control surface 63 uses the hydrophobic effect to control the location of the composite liquid cell 61. Hydrophobic surfaces repel aqueous based media but silicon-based oils readily wet the surfaces permitting control using capillary tension. Bringing the control surface 63 into contact with the composite liquid cell 61 will result in a wetting of the surface of the body by the outer fluid of the composite liquid cell 61. The composite liquid cell can then be transported to a location on the carrier fluid 62 by translating the control surface 63. Using this transport motion one or more composite liquid cells can be merged or additional biological samples can be added to a composite liquid cell.

Figure 7:
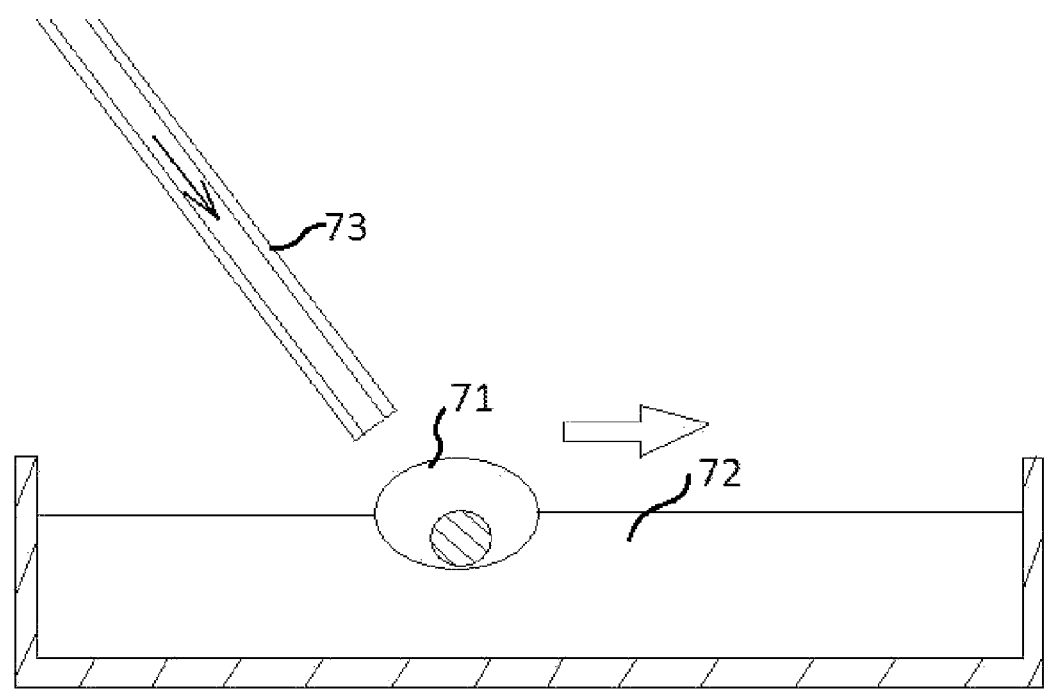
FIG. 7 schematically illustrates control of a composite liquid cell using directional air control.

In another embodiment, referring to FIG. 7 a composite liquid cell 71 positioned on an immiscible carrier fluid 72 can be position controlled using a directional control tube 73. The directional control tube 73 provides an air jet which when directed to impinge on the composite liquid cell 71 generates a drag force larger than the translational resistance, thereby transporting the cell fluid in a controlled manner. Using this transport motion one or more composite liquid cells can be merged or additional biological samples can be added to a composite liquid cell.

In another embodiment, referring to FIG. 8A a composite liquid cell 81 positioned on an immiscible carrier fluid 82 can be temporarily anchored using a hydrophobic spur 83 attached to a base 84. Using this transport motion one or more composite liquid cells can be merged or additional biological samples can be added to a composite liquid cell.

Figure 9A:
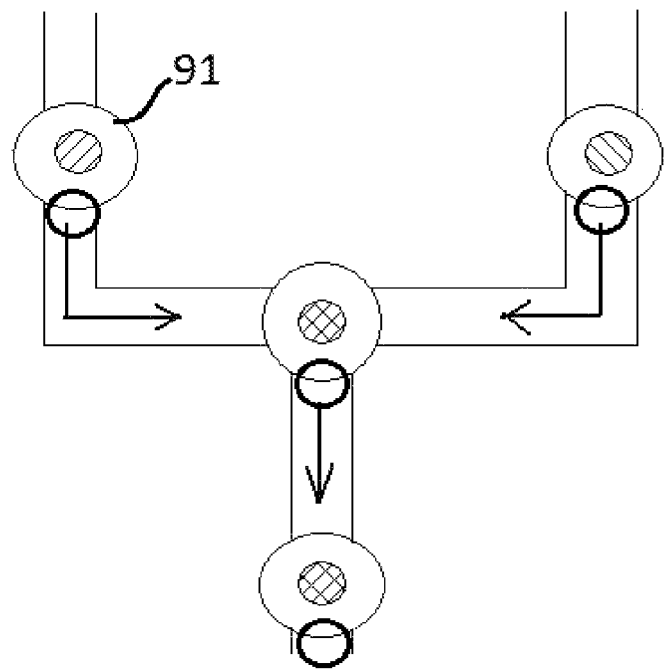
FIGS. 9A and 9B schematically illustrate a transport mechanism for continuous flowing processing of biochemistry along a static hydrophobic control surface using electrostatic forces.
Figure 9B:
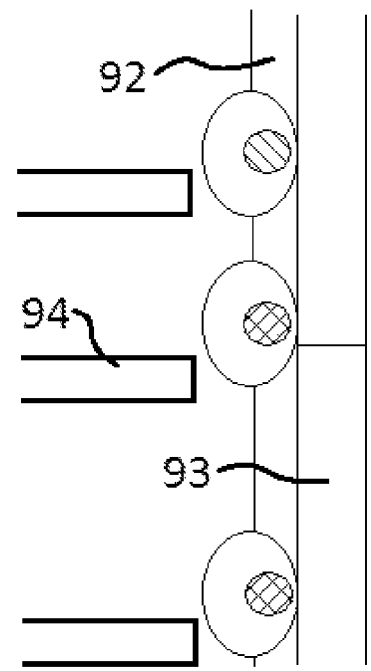

In another embodiment, a composite liquid cell can be moved using a combination of electrostatic forces and the hydrophobic effect. Referring to FIGS. 9A and 9B, a composite liquid cell 91 is positioned on an immiscible carrier fluid 92, and located in contact with a hydrophobic track 93. A dynamic controlling surface 94 uses hydrostatic forces to move the composite liquid cell along the defined hydrophobic track. The controlling surface 94 can also be used to separate the composite liquid cell from the hydrophobic spar and move the composite liquid cell independently or to another hydrophobic location. Using this transport motion one or more composite liquid cells can be merged or additional biological samples can be added to a composite liquid cell.

In another embodiment the hydrophobic spars are partially submerged in the carrier fluid.

In another embodiment there are multiple controlling surfaces, allowing for independent motion of discrete composite liquid cells.

In another embodiment, the transport motion is a combination of dynamic control using the hydrophobic effect. A composite liquid cell is positioned on an immiscible carrier fluid and located in contact with a hydrophobic track. A dynamic controlling surface using the hydrophobic effect moves the composite liquid cell along the defined hydrophobic track. The controlling surface can also be used to separate the composite liquid cell from the hydrophobic spar and move the composite liquid cell independently or to another hydrophobic location. Using this transport motion one or more composite liquid cells can be merged or additional biological samples can be added to a composite liquid cell.

In another embodiment, the carrier fluid is a continuously flowing fluid and with it's resulting momentum transporting the composite liquid cells along its streamlines. In another embodiment the carrier fluid momentum is assisted by static hydrophobic surfaces along which the composite liquid cells can progress. In another embodiment the carrier fluid momentum is assisted by dynamic hydrophobic surfaces by which the composite liquid cells can be transported.

Unless otherwise stated, any of the disclosure herein related to composite liquid cells generally, also applies to multi-sample composite liquid cells in particular.

Generating Composite Liquid Cells with Multiple Samples

Figure 10A:
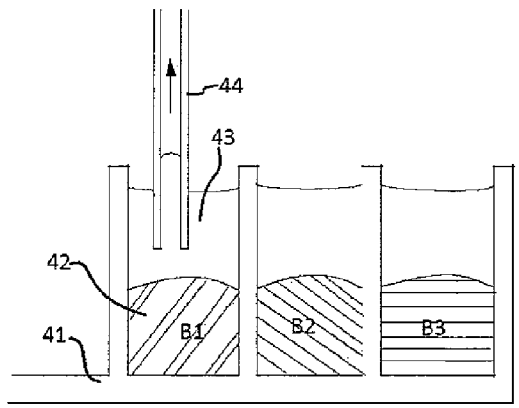
FIGS. 10A-10F schematically illustrate multi-sample composite liquid cell generation of the invention using a control tube and a variable flow direction.
Figure 10B:
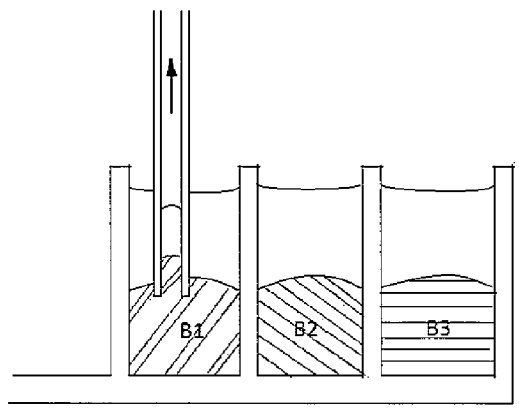
Figure 10C:
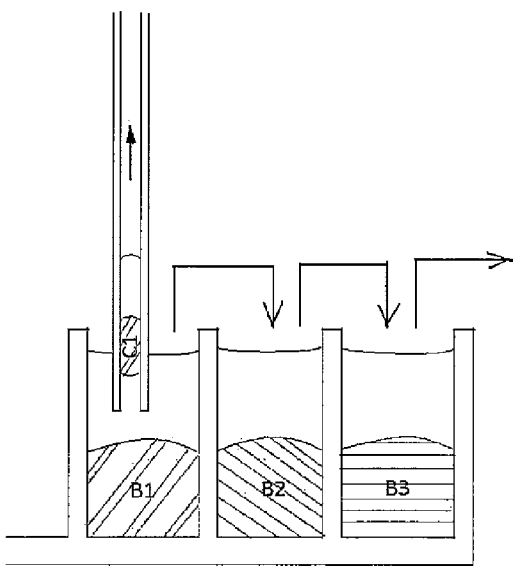
Figure 10D:
Figure 10E:
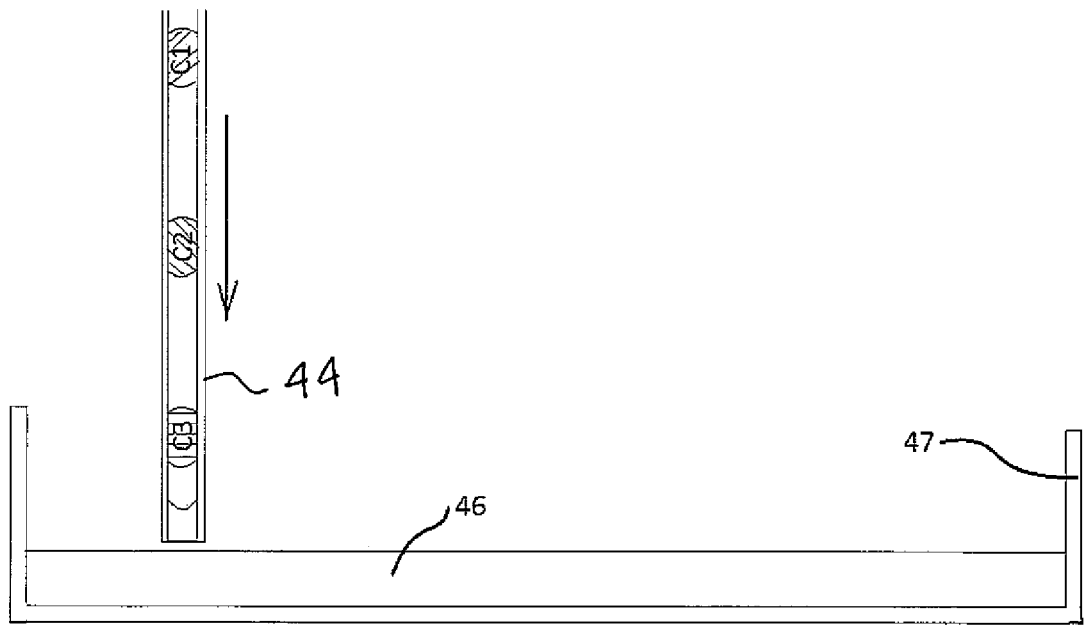
Figure 10F:
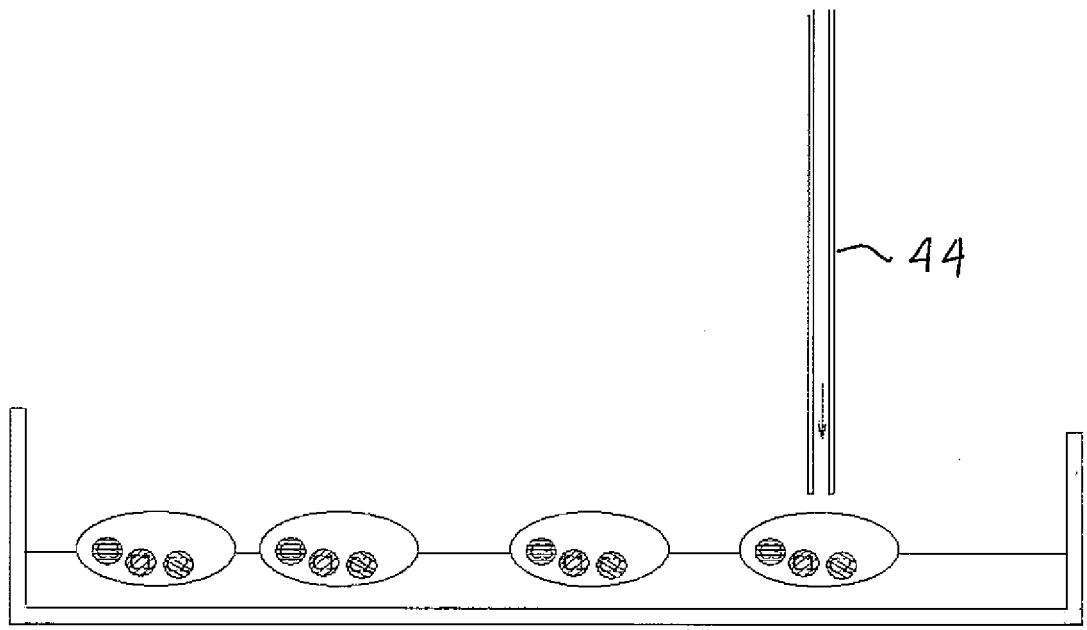

In one embodiment, referring to FIGS. 10A-10F, composite liquid cells can be generated using the method and system shown. Referring to FIG. 10A a well plate 41 contains biological sample 42 in one or more locations (B101, B102, B103) and is covered by an immiscible fluid 43. A control tube 44 has a controllable pressure across the tube. In this mode of operation a continuous pressure drop is held within the tube, thereby withdrawing the immiscible fluid 43 into the control tube 44 when the control tube 44 is translated into contact with the immiscible fluid 43. A volume of immiscible fluid 43 is withdrawn into the tube. Referring to FIG. 10B the control tube 44 translates into the biological sample 41 and withdraws a volume of biological sample C101. Referring to FIG. 10C the control tube returns to the immiscible fluid layer withdrawing a volume of immiscible fluid. Following this, the control tube then repeats the procedure at the same biological sample or translates while still within the fluid overlay prior to repeating the procedure at a new biological sample location. Following the withdrawal of the immiscible fluid and biological samples for a multi-sample composite liquid cell the control tube then exits the immiscible oil and withdraws air prior to repeating the procedure for a new composite liquid cell. Referring to FIG. 10D the control tube is loaded with biological samples C101, C102, C103 and immiscible fluid for the multi-sample composite liquid cells. Referring to FIG. 10E the control tube is positioned over the carrier oil layer 46 housed in a biocompatible container 47. The control tube may either be in contact with or positioned between 0-3 mm above the free surface of the carrier oil 46. The flow direction is reversed in the control tube and immiscible fluid, sample and immiscible fluid are deposited on the free surface of the carrier oil, generating a multi-sample composite liquid cell. Referring to FIG. 10F upon depositing a complete multi-sample composite liquid cell 48 the control tube translates to a new position to deposit the next multi-sample composite liquid cell.

Figure 11A:
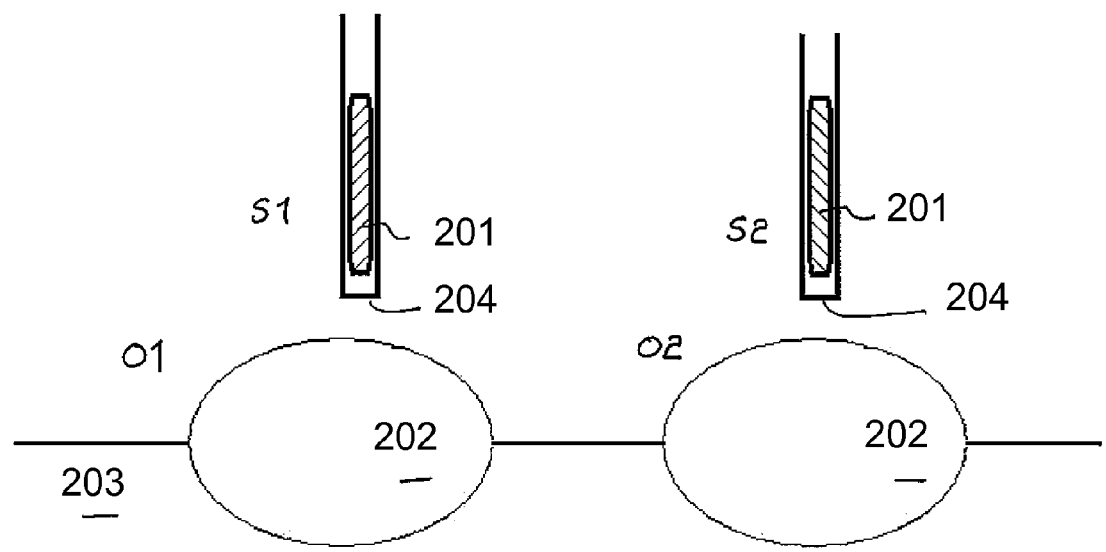
FIGS. 11A-11C schematically illustrate multi-sample composite liquid cell generation using electrostatic forces.
Figure 11B:
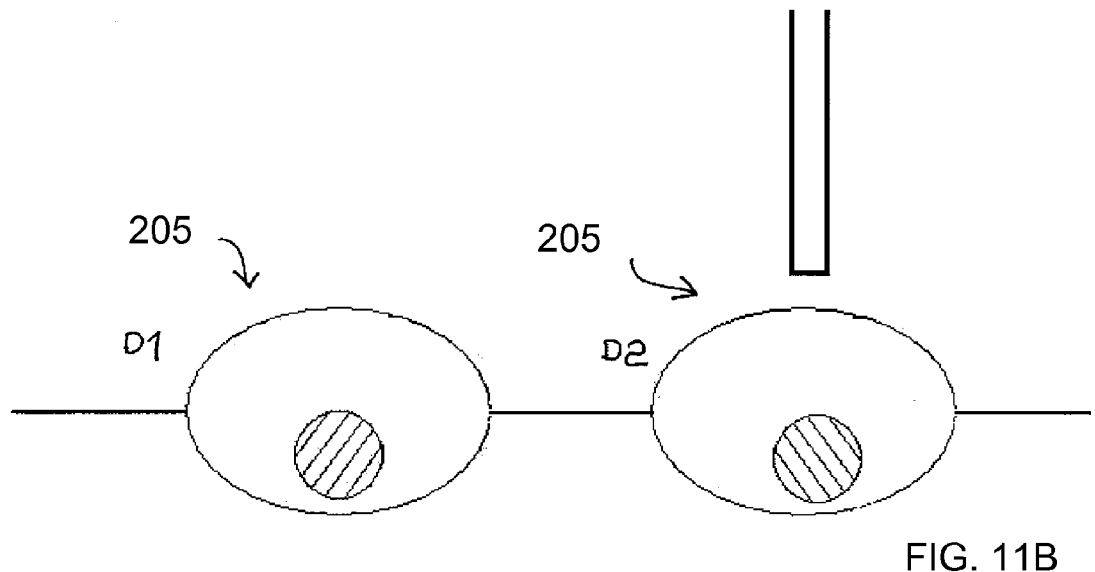
Figure 11C:
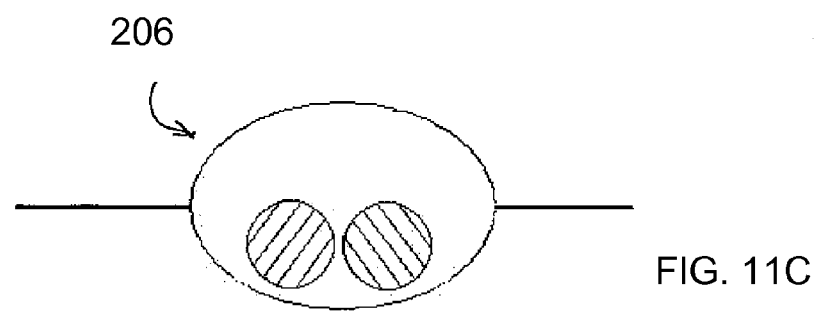

Referring to FIGS. 11A-11C, a biological sample 201 at one or more locations (S1, S2) and a mutually immiscible fluid cell 202 at one or more locations (O1, O2) positioned on a free surface of a mutually immiscible carrier fluid 203 can be combined using a control surface 204. The control surface 204 uses electrostatic forces to control the location of the immiscible fluid cell 202. The control surface is charged and is brought in close proximity to the immiscible fluid cell 202, a charge separation will occur. For example the control surface 204 is given a highly positive charge, negatively charged ions within the immiscible fluid cell 202 will separate towards the charged body. The result is a polar charge separation and an attractive force towards the charged body. Referring to FIG. 11B a composite liquid cell 205 at one or more locations (D1, D2) is generated. The control surface 204 uses electrostatic forces to control the location of the composite liquid cell 205. Referring to FIG. 11C a multi-sample composite liquid cell 206 is generated by merging two or more composite liquid cells.

Figure 12A:
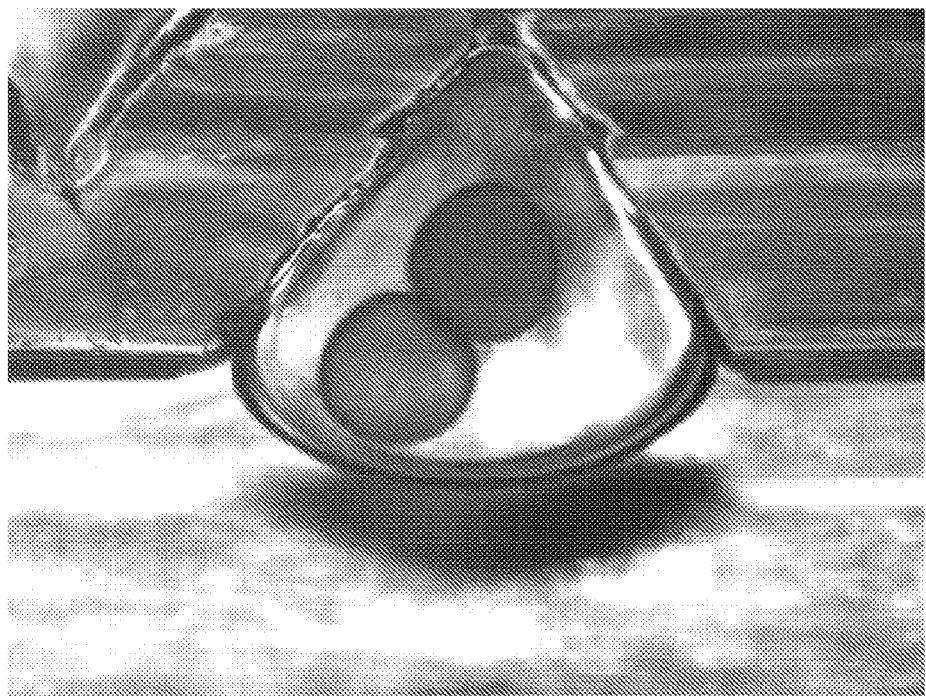
FIGS. 12A and 12B are photographs showing a multi-sample composite liquid cell.
Figure 12B:
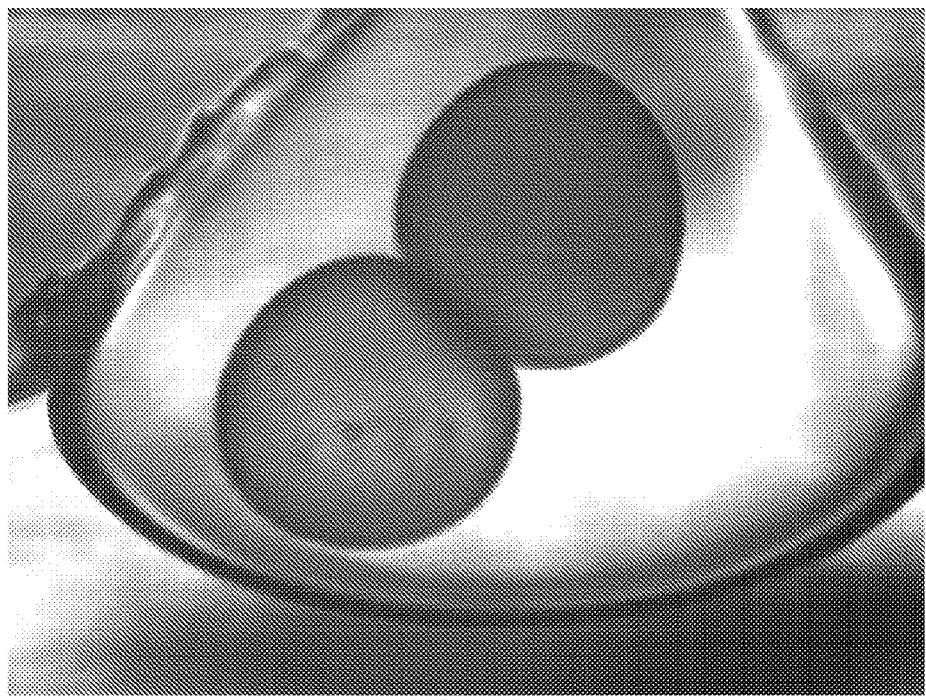

FIGS. 12A and 12B are images showing a multi-sample composite liquid cell resulting from this method. In this example, a composite liquid cell comprising of a 2.5 micro-liter volume of distilled water with 2% green dye and 15 micro-liter of immiscible fluid Phenylmethylpolysiloxane—PD5 oil with 5% polysorbate additive—SPAN 80 (v/v) was generated. A second composite liquid cell was generated with the same reagents however a 2% red dye was used in the distilled water instead of the green dye. The colours are discernable as distinct shades of grey in the figures. The two composite liquid cells were merged using hydrophobic surfaces (the inverted V-shape visible in these images) and located within a stabilisation feature on a hydrophobic spar.

Figure 13A:
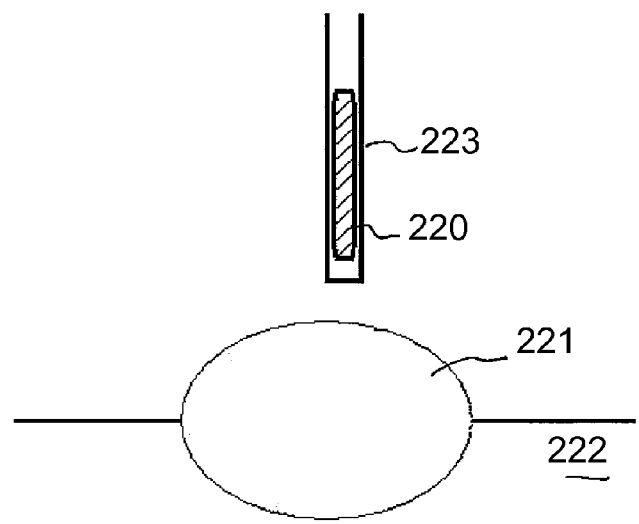
FIGS. 13A-13C schematically illustrate multi-sample composite liquid cell generation using surface tension.
Figure 13B:
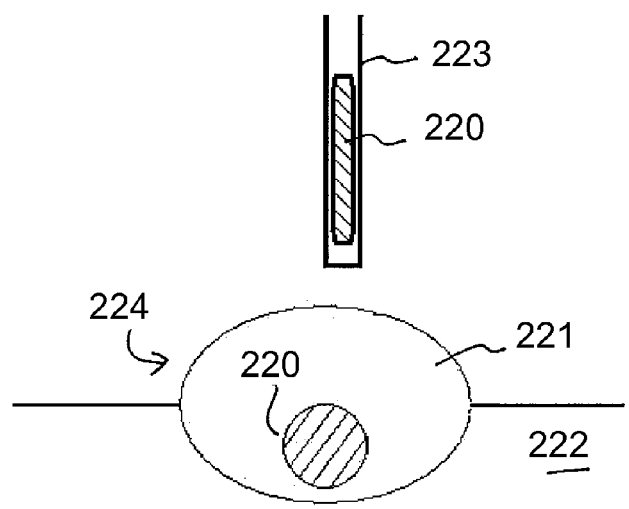
Figure 13C:
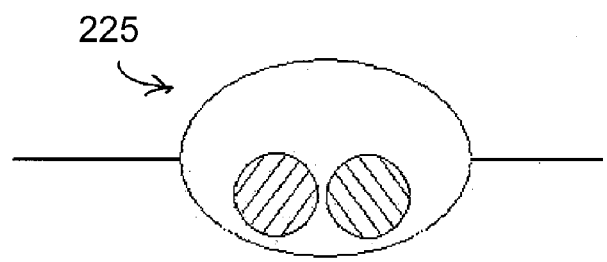

In another embodiment, referring to FIGS. 13A-13C, a biological sample 220 within a control tube 223 and a mutually immiscible fluid cell 221 positioned on a free surface of a mutually immiscible carrier fluid 222 can be combined using the hydrophobic effect of a tubular control surface 223. The control tube 223 uses the hydrophobic effect to control the location of the immiscible fluid cell 221. Hydrophobic surfaces repel aqueous-based media but silicon-based oils readily wet the surfaces, permitting control using capillary tension. Referring to FIG. 13B, by bringing the control tube 223 into contact with the immiscible fluid cell 221 will result in a wetting of the surface of the body by the immiscible fluid cell 221. The biological sample 220 can then be released to make contact with the immiscible fluid cell 221 on the carrier fluid 222. As shown in FIG. 13B a composite liquid cell 224 is generated. Referring to FIG. 13C, by repeating the procedure with another biological sample volume, a multi-sample composite liquid cell 225 is generated.

Figure 14A:
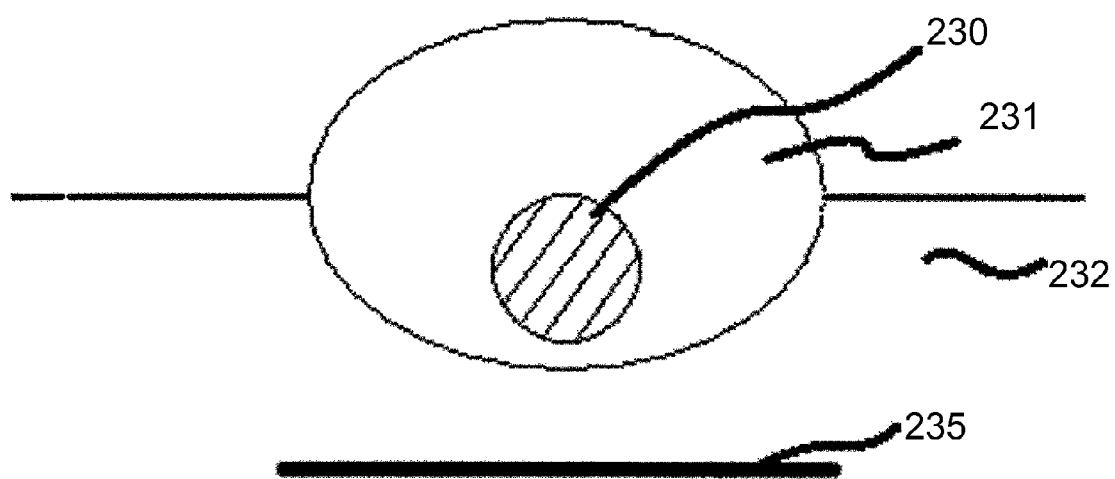
FIGS. 14A and 14B schematically illustrate multi-sample composite liquid cell generation using mechanical agitation.
Figure 14B:
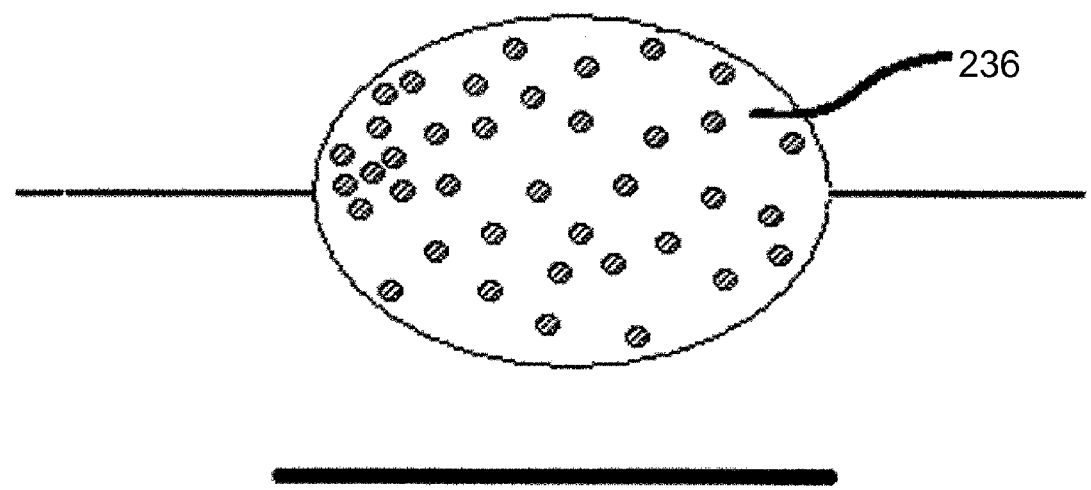

In another embodiment, referring to FIGS. 14A and 14B, a biological sample 230 within a mutually immiscible fluid cell 231 positioned on a free surface of a mutually immiscible carrier fluid 232 can be subdivided using an ultrasonic surface 235. Referring to FIG. 14B a multi-sample composite liquid cell 236 is generated.

Figure 15A:
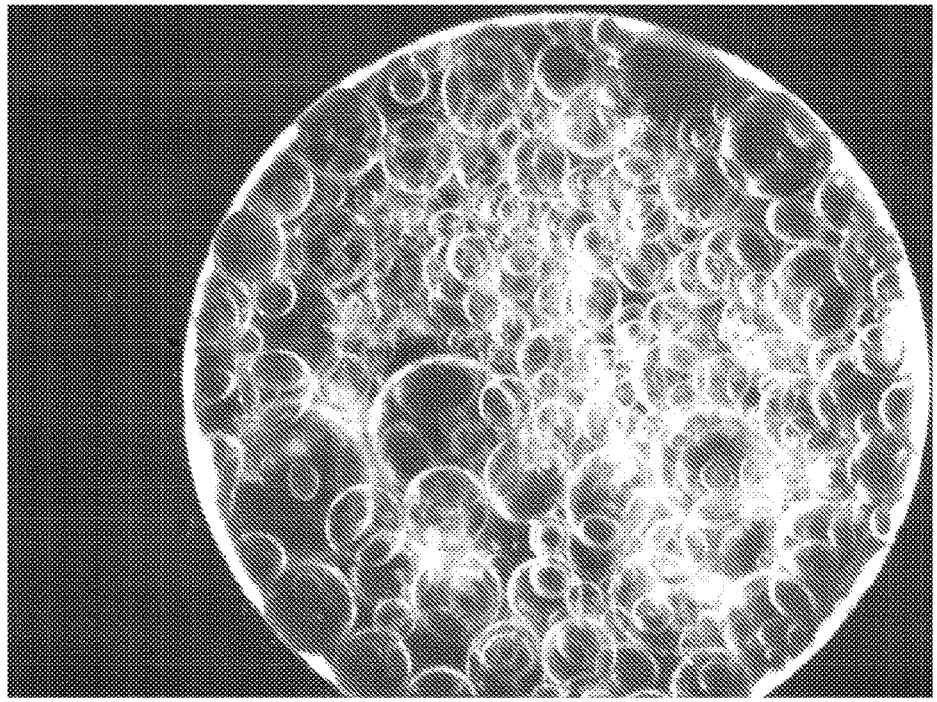
FIGS. 15A and 15B are photographs of an emulsion-based multi-sample composite liquid cell.
Figure 15B:
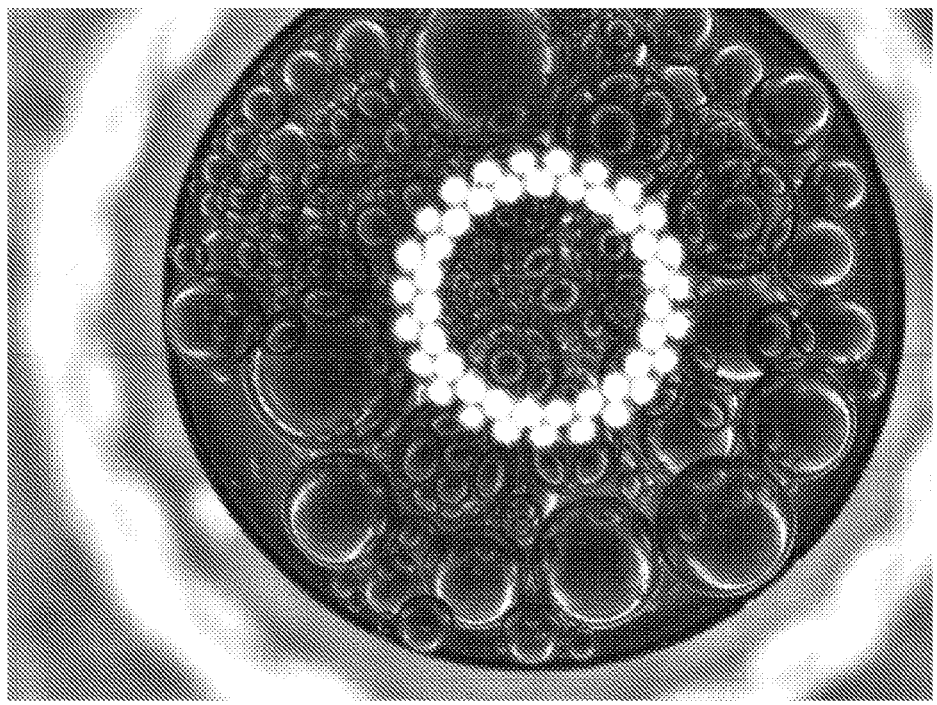

FIGS. 15A and 15B are images showing such a multi-sample composite liquid cell like the cell 236 of FIG. 14B. In this example, a 100 micro-liter volume of distilled water was vortexed in a 500 micro-liter immiscible fluid cell composed of Phenylmethylpolysiloxane based oil—PD5 with 5% polysorbate additive—SPAN 80 (v/v). FIG. 15B used distilled water with a 2% green dye for the biological sample. FIGS. 15A and 15B are a 20 micro-liter representative sample.

Figure 16:
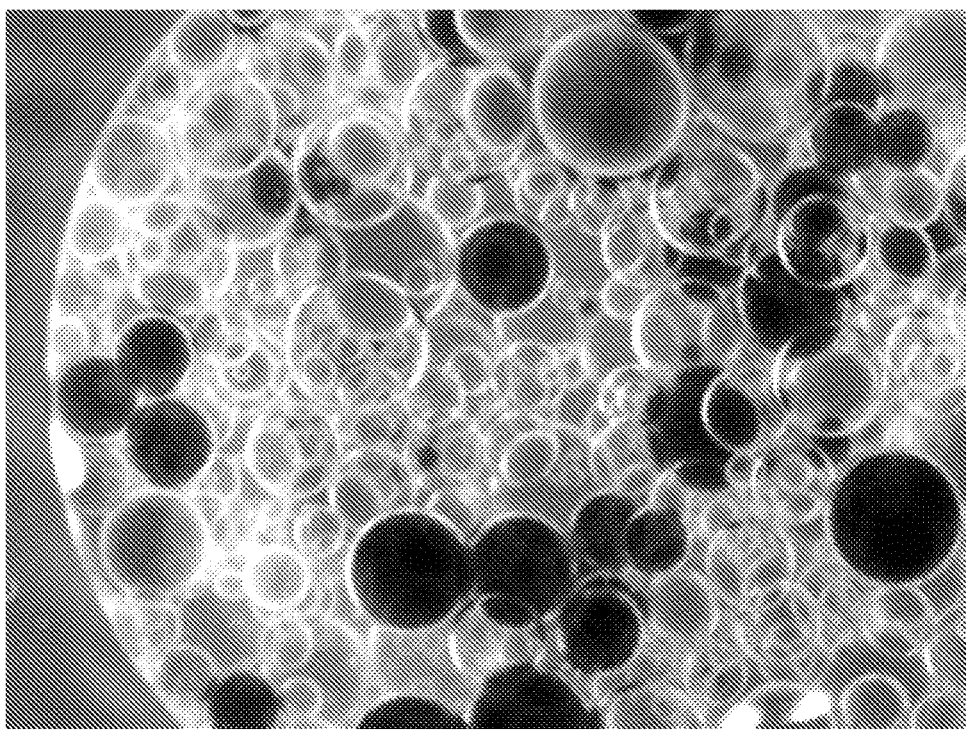
FIG. 16 is a photograph of a multi-sample composite liquid cell with multiple internal sample targets.

In another embodiment, a composite liquid cell with multiple samples of multiple distinct sample targets is generated. Referring to FIG. 16, four distinct sample targets are emulsified and combined together stably as a single multi-sample composite liquid cell with multiple internal sample targets. Four individual composite liquid cells were generated with 10 micro-liters of distilled water with green dye 2%, blue dye 2%, yellow dye 5%, and no dye in a 500 micro-liter immiscible fluid cell composed of Phenylmethylpolysiloxane based oil—PD5 with 5% polysorbate additive—SPAN 80 (v/v). Following emulsification the composite liquid cells were merged, see FIG. 16. Evident from FIG. 16 is that the dye-free water samples do not become contaminated by the dyed water samples, showing that there is no transfer between the samples within the multi-sample composite liquid cell. The various colours are discernable as distinct shades of grey.

Figure 17A:
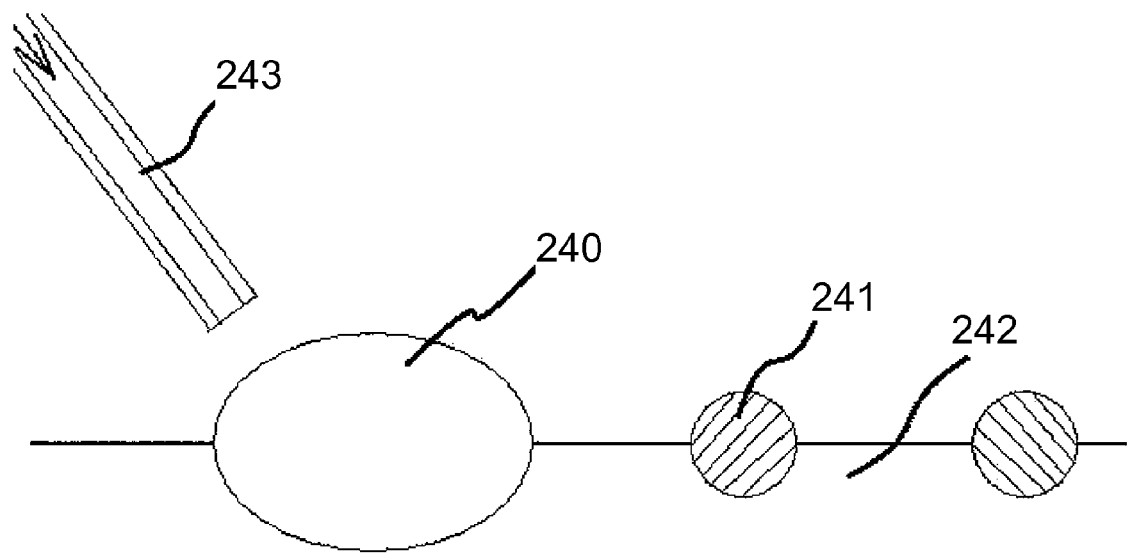
FIGS. 17A and 17B schematically illustrate multi-sample composite cell generating using directional air control.
Figure 17B:
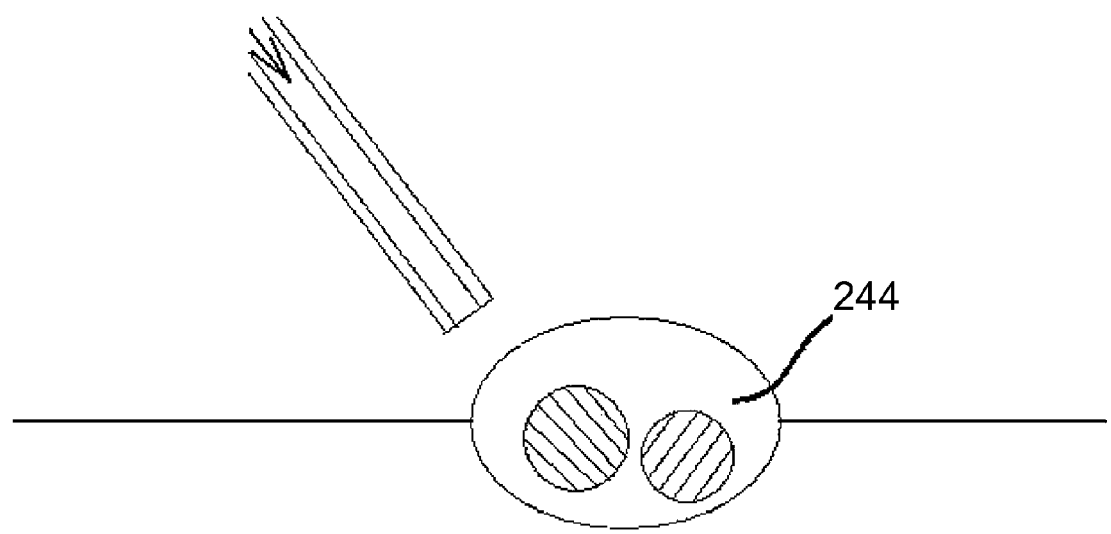

In another embodiment, referring to FIGS. 17A and 17B, a mutually immiscible fluid cell 240 and two or more biological samples 241, positioned on a free surface of a mutually immiscible carrier fluid 242 are combined using a directional control tube 243. The directional control tube 243 provides an air jet which when directed to impinge on the samples 241 generates a drag force larger than the translational resistance, thereby transporting the buffer fluid 240 and the samples 241 in a controlled manner. Referring to FIG. 17B a resulting multi-sample composite liquid cell 244 is generated.

Transporting the Composite Liquid Cells with Multiple Samples

All general methods of transporting composite liquid cells, for example those discussed above, are also applicable to multi-sample composite liquid cells.

Figure 18A:
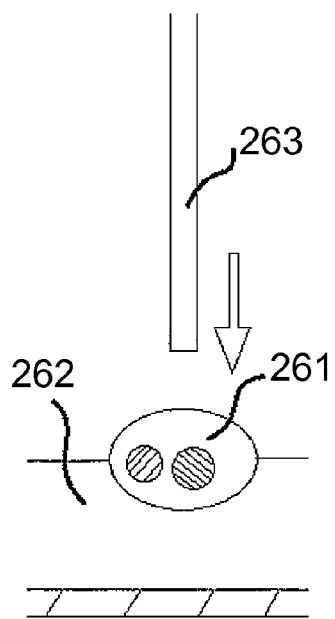
FIGS. 18A-18C schematically illustrate control of a multi-sample composite liquid cell using the hydrophobic effect.
Figure 18B:
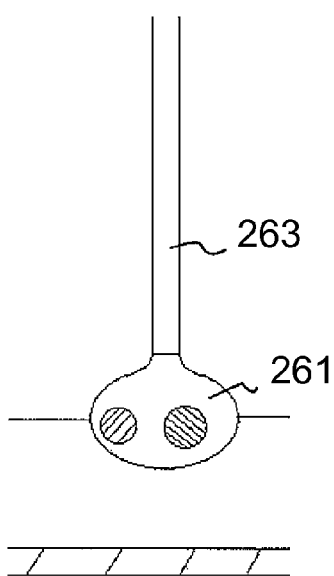
Figure 18C:
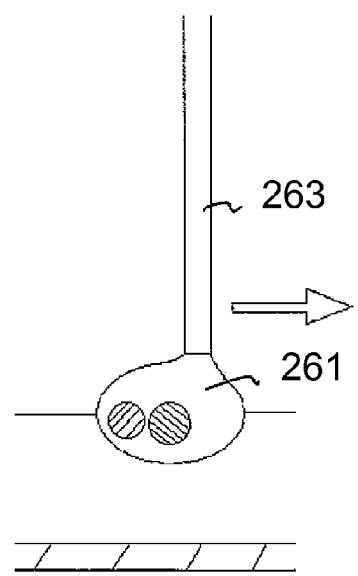

Referring to FIGS. 18A-18C, and as explained in reference to FIGS. 6A-6C, a multi-sample composite liquid cell 261 positioned on a free surface of a mutually immiscible carrier fluid 262 can be transported using a device having a hydrophobic control surface 263.

Figure 19A:
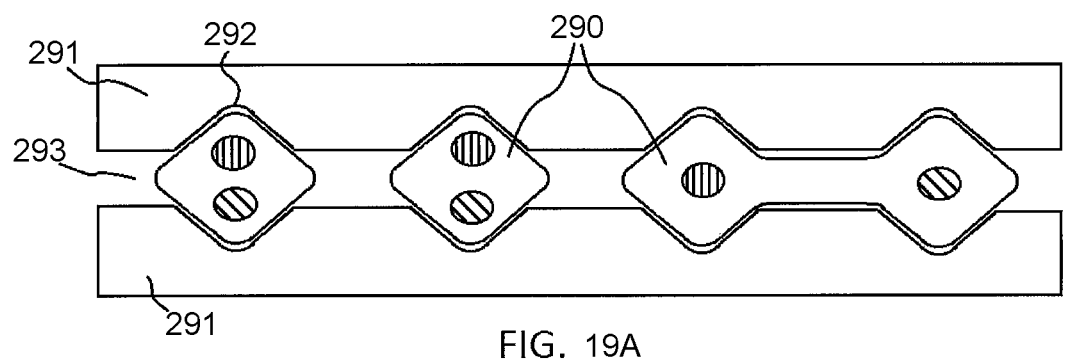
FIGS. 19A and 19B schematically illustrate multi-sample composite cell transportation using a hydrophobic control surface with stabilisation features.
Figure 19B:
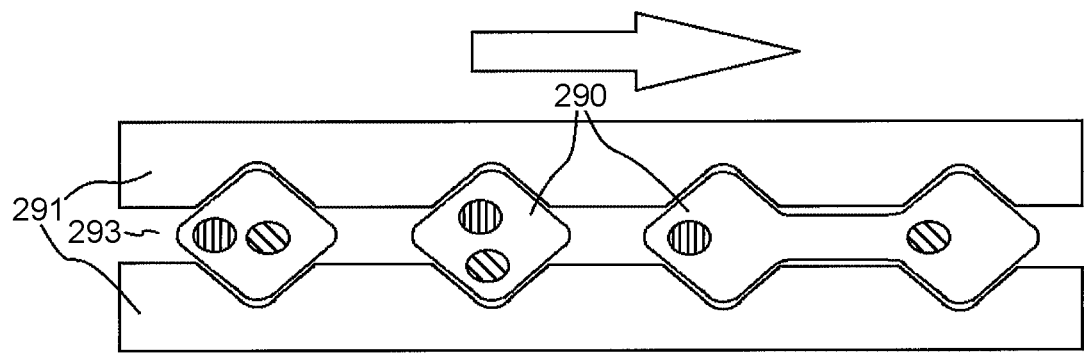

In another embodiment the control surface is partially submerged in the carrier fluid. Referring to FIGS. 19A and 19B, the multi-sample composite liquid cell 290 positioned on a free surface of immiscible carrier 293 is confined between two hydrophobic spars 291. The hydrophobic spars 291 have stabilisation features 292 within them. As shown in FIG. 19A these features are used to control the samples within the composite liquid cell, and as shown in FIG. 19B the hydrophobic spars can be moved along the carrier fluid 293 stably transporting the multi-sample composite liquid cells 290.

Figure 20:
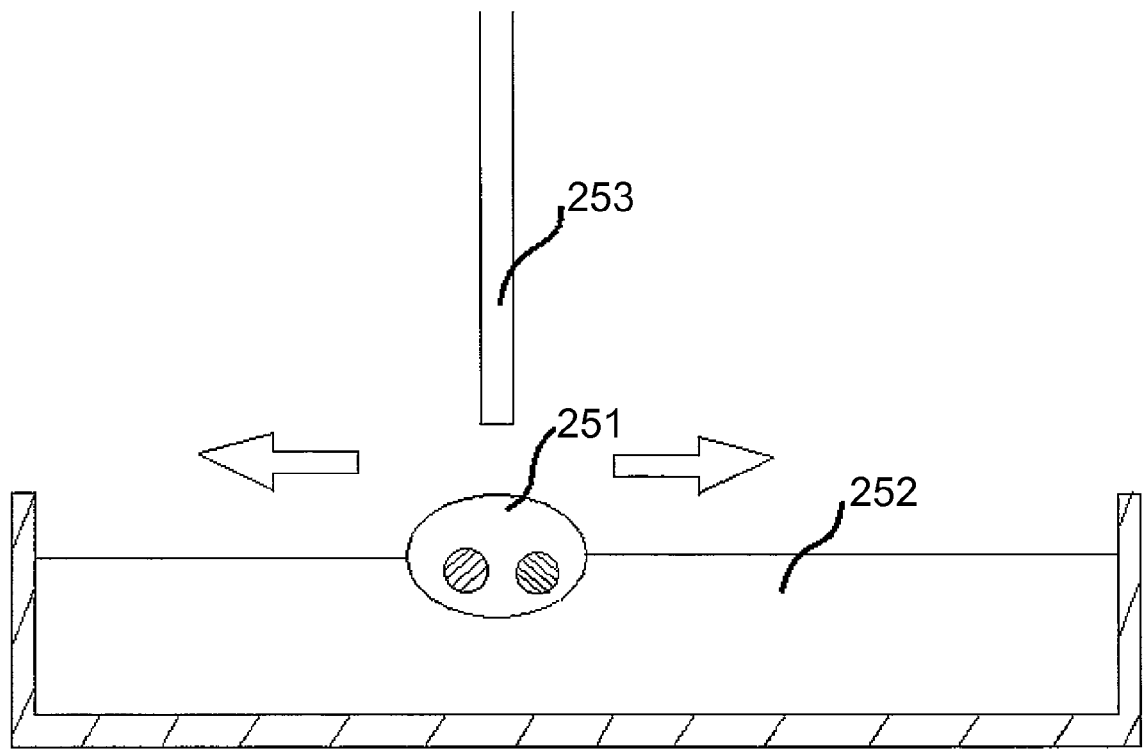
FIG. 20 schematically illustrates control of a multi-sample composite liquid cell using electrostatic forces.

In another embodiment, referring to FIG. 20, and as explained in reference to FIG. 5, the multi-sample composite liquid cell 251 is transported on an immiscible carrier fluid 252 by a device control surface 253 using electrostatic forces.

Figure 21:
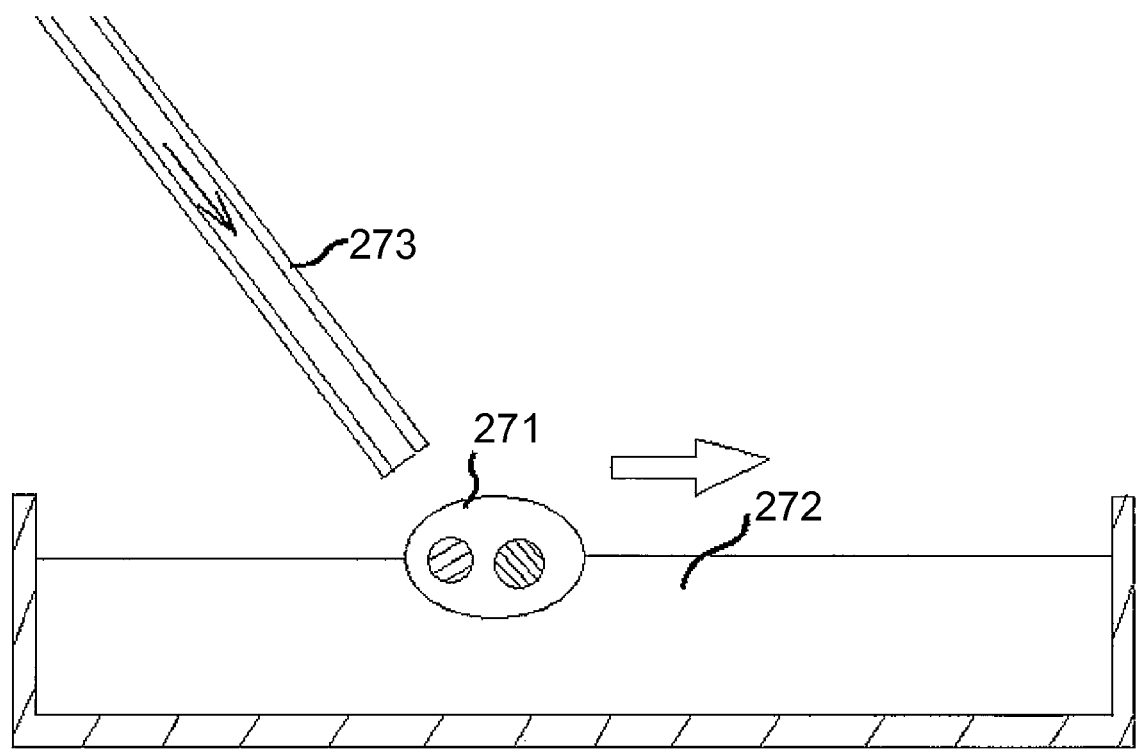
FIG. 21 schematically illustrates control of a multi-sample composite liquid cell using directional air control/

In another embodiment, referring to FIG. 21, and as explained in reference to FIG. 7, a composite liquid cell 271 positioned on an immiscible carrier fluid 272 can be position controlled using a directional control tube 273 that provides an air jet.

Figure 8:
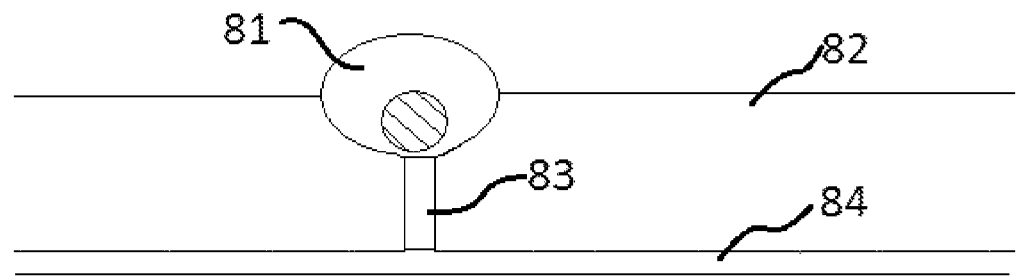
FIG. 8 schematically illustrates a static control spur anchoring a composite liquid cell.
Figure 22:
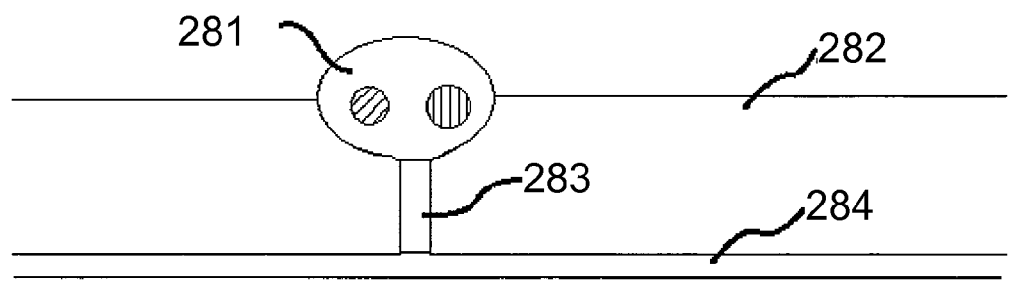
FIG. 22 schematically illustrates static control spur anchoring a multi-sample composite liquid cell.

In another embodiment, referring to FIG. 22, and as explained in reference to FIG. 8, a multi-sample composite liquid cell 281 positioned on an immiscible carrier fluid 282 can be temporarily anchored using a hydrophobic spur 283 attached to a base 284.

Internal Control of Multiple Sample Volumes with a Composite Liquid Cell

Figure 23:
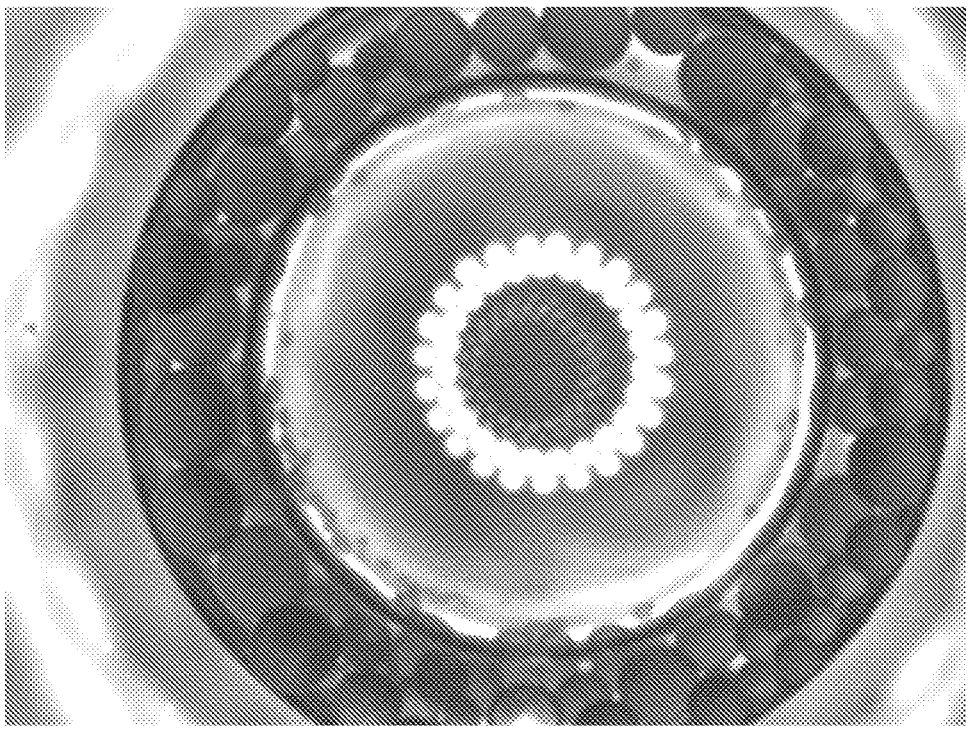
FIG. 23 is a photograph of a multi-sample composite liquid cell with a central control volume used to array the original samples of the composite liquid cell.

In one embodiment the internal sample volumes with a multi-sample composite liquid cell can be arrayed for 2D analysis. Referring to FIG. 23 a large sample volume can be added to the composite liquid cell and positioned centrally resulting in the original composite liquid cell samples being arrayed in the annulus for analysis. A 100 micro-liter volume of distilled water with 2% green dye was vortexed in a 500 micro-liter immiscible fluid cell composed of Phenylmethylpolysiloxane based oil—PD5 with 5% polysorbate additive—SPAN 80 (v/v). A 20 micro-liter representative sample was segmented and a large un-dyed water sample, in the order of 10 micro-liters was pipetted into the centre of the composite liquid cell. The resulting structure is shown in FIG. 23.

In one embodiment the internal samples of a multi-sample composite liquid cell are recombined using a sorbate additive. Examples of polysorbate additives are SPAN 80 and Tween 20 but are not limited to these. These additives within the buffer encapsulating fluid range between 0.001% and 10%.

Mechanical Features for Stabilisation

Referring to FIGS. 24A-24D, a composite liquid cell comprising of a target sample 311 encapsulated in an immiscible buffer fluid 312 positioned on a free surface of a mutually immiscible carrier fluid 313 is stably positioned at a hydrophobic surface 314. The hydrophobic surface 314 is positioned on or in the mutually immiscible carrier fluid 313. The hydrophobic surface 314 with localised stabilisation features 315 control the position of the composite liquid cell. The stabilisation features allow for generation, and/or location control, and/or movement control, and/or mixing, and/or splitting, and/or processing of biological samples within a composite liquid cell and positioned on an immiscible carrier fluid.

Figure 24A:
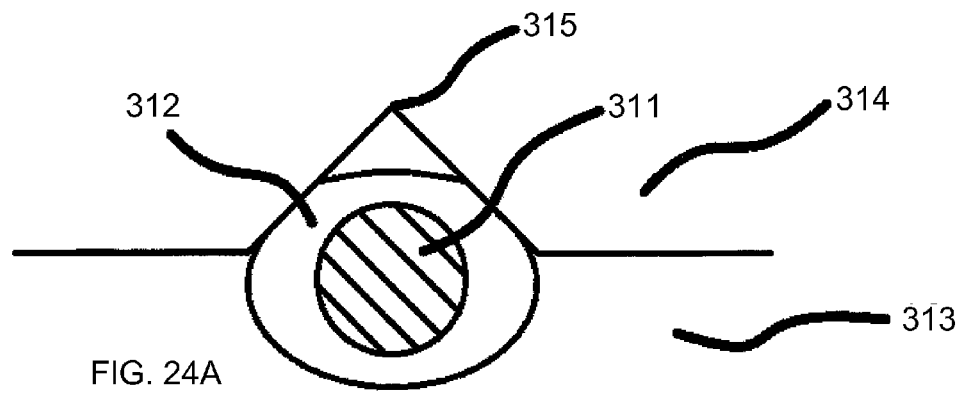
FIGS. 24A-24D schematically illustrate a unit hydrophobic stabilisation feature for a composite liquid cell.
Figure 24B:
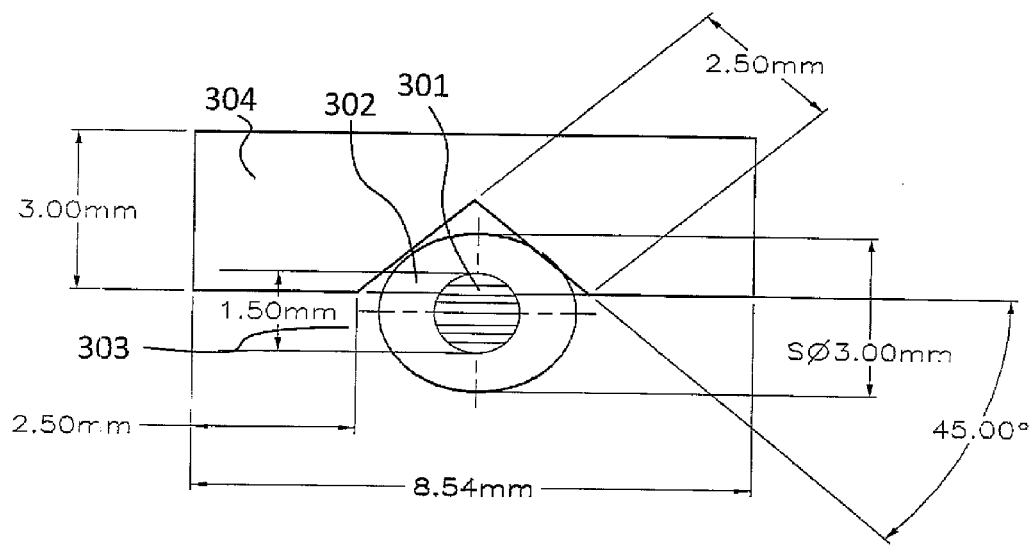
Figure 24C:
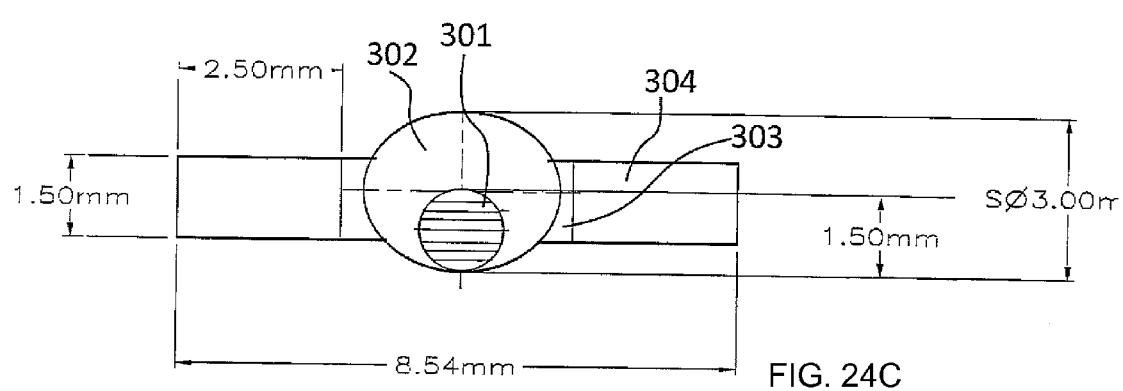
Figure 24D:
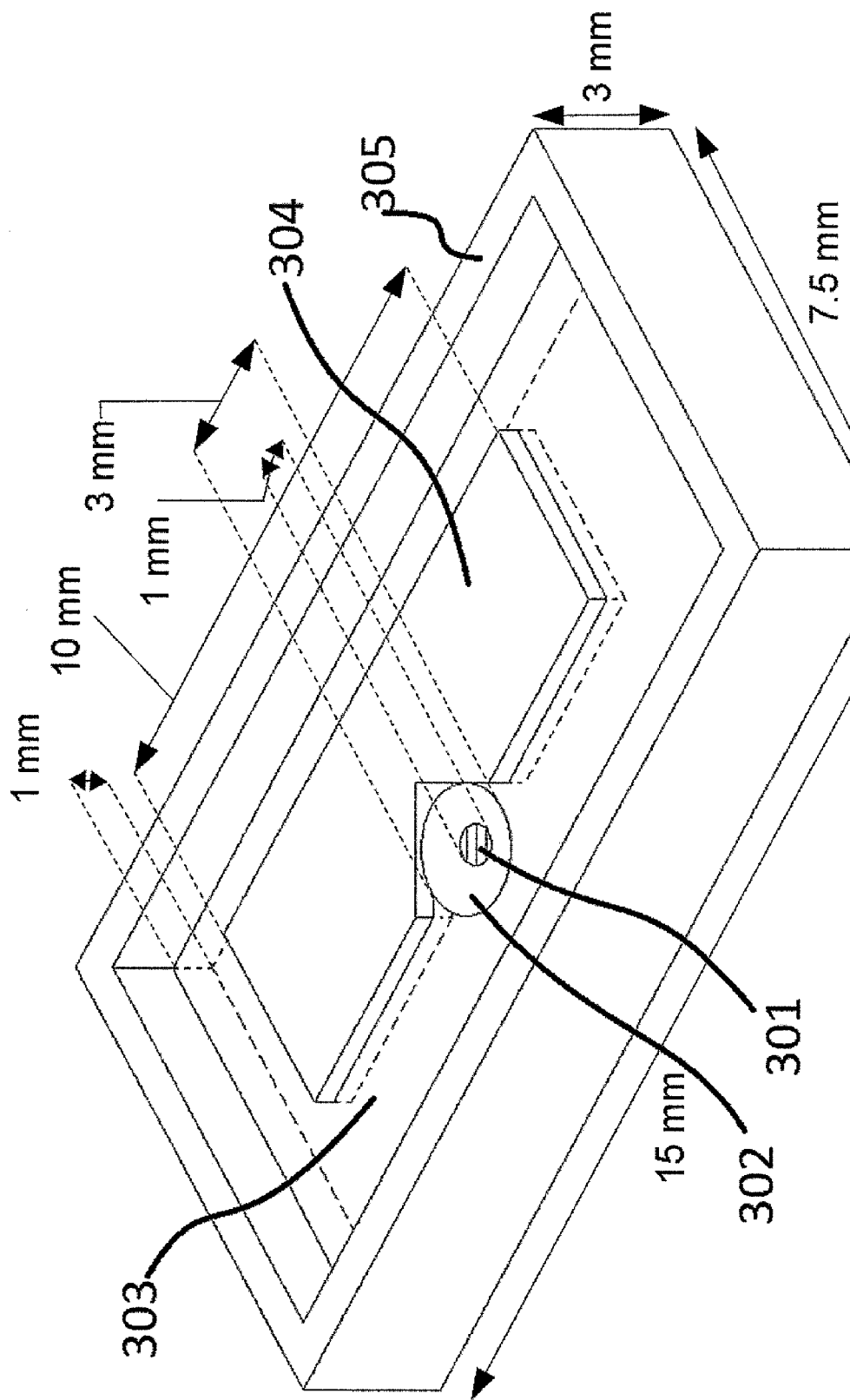

Referring to FIG. 24B in one embodiment the composite liquid cell comprises of approximately 1.7 micro-liter target sample 301 encapsulated in approximately 12 micro-liters immiscible buffer 302 positioned on a free surface of a mutually immiscible carrier fluid 303 is stably positioned at a hydrophobic feature 404 having an inverted V-shaped surface 304. The hydrophobic surface is positioned on or in the mutually immiscible carrier fluid 303. The hydrophobic device or feature 304 with localised stabilisation features controls the position of the composite liquid cell. In one embodiment the stabilisation feature is a notch of 45 degrees with an face depth of 2.5 mm and a thickness of 1.5 mm. This is used to control micro-liter size composite liquid cell. Referring to FIG. 24C an underneath plan of the embodiment is shown. Referring to FIG. 24D the previously described embodiment is shown with a housing 305 having a surrounding wall for retaining the carrier liquid.

Figure 25A:
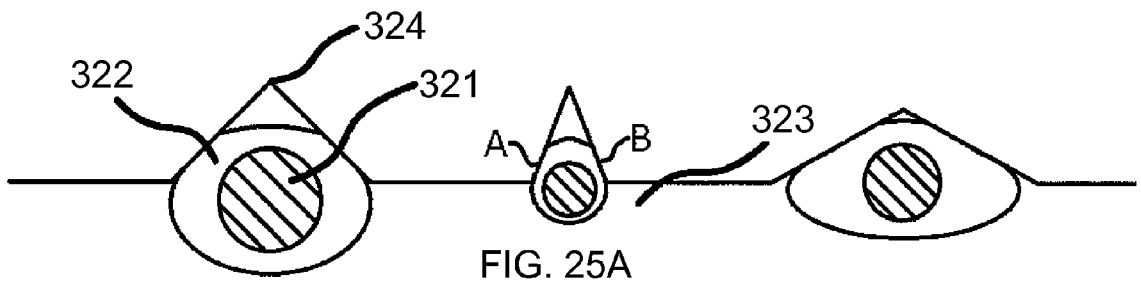
FIGS. 25A-25D schematically illustrate a number of different hydrophobic stabilisation feature shapes for a composite liquid cell.
Figure 25B:
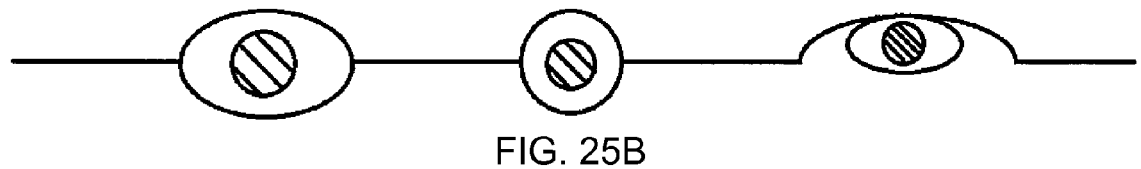
Figure 25C:
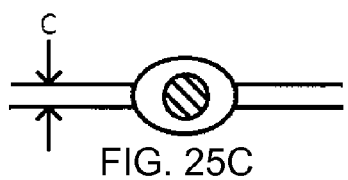
Figure 25D:

Referring to FIGS. 25A-25D, a stabilisation feature has a number of parameters which are adjusted for a given application. Two of these parameters are the feature shape and the feature thickness. The shape of the feature has an impact on the overall size and location control of an internal sample 321. Referring to FIG. 25A an inverted 'V' shaped stabilisation feature 324 controls the internal sample 321 location with the tangent points A & B as illustrated. Referring to FIG. 25B a curved shape stabilisation feature 325 has less control over the internal position of the sample. The variation in shape allows for customisation of the composite liquid cell ratios of an internal sample 321 to encapsulating buffer fluid 322. Typically, a circular shape can achieve a greater sample volume to encapsulating fluid ratio and maintain contamination-free samples. Referring to FIG. 25C the stabilisation feature thickness C has an impact on the stabilisation of the composite liquid cell, allowing for customisation of applications. For a larger thickness, typically greater than 50% of the composite liquid cell diameter the stabilisation properties do not improve. For stationary control or processing of a composite liquid cell, a thickness in the range of 5-50% is sufficient for stabilisation of the composite liquid cell on the free carrier surface 323. The stabilisation feature is positioned on or in the carrier fluid. Referring to FIG. 25D the stabilisation feature can be tapered for composite liquid cell generation, and/or location control, and/or movement control, and/or mixing, and/or splitting, and/or processing of biological samples within a composite liquid cell and positioned on an immiscible carrier fluid.

Figure 26:
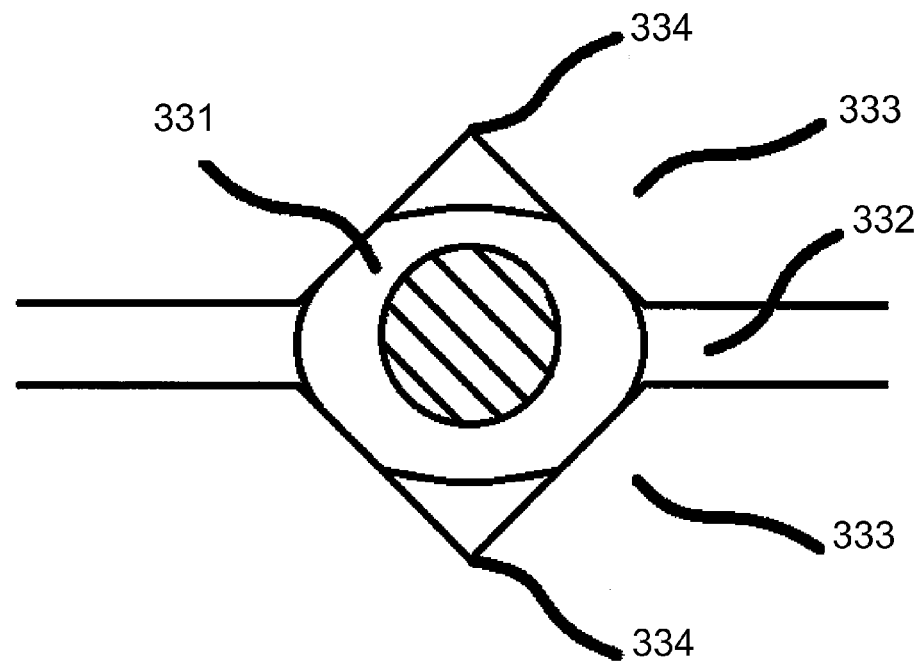
FIG. 26 schematically illustrates two hydrophobic stabilisation features for a single composite liquid cell.

Referring to FIG. 26 a composite liquid cell 331 positioned on an immiscible carrier fluid 332 is positioned between two hydrophobic surfaces 333 with location features 334. The stabilisation features allow for generation, and/or location control, and/or movement control, and/or mixing, and/or splitting, and/or processing of biological samples within a composite liquid cell and positioned on an immiscible carrier fluid.

Figure 28:
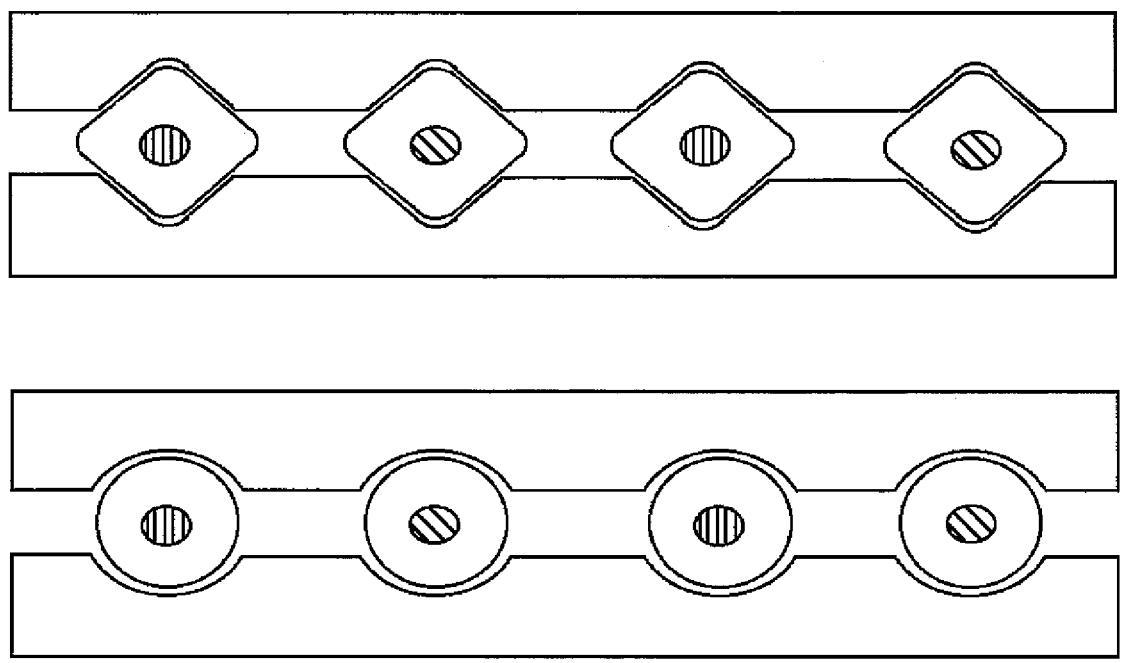
FIG. 28 schematically illustrate an array of hydrophobic stabilisation features.

Referring to FIG. 28 a network of discrete composite liquid cells can be generated.

Generating Composite Liquid Cell with Mechanical Features

Figure 27A:
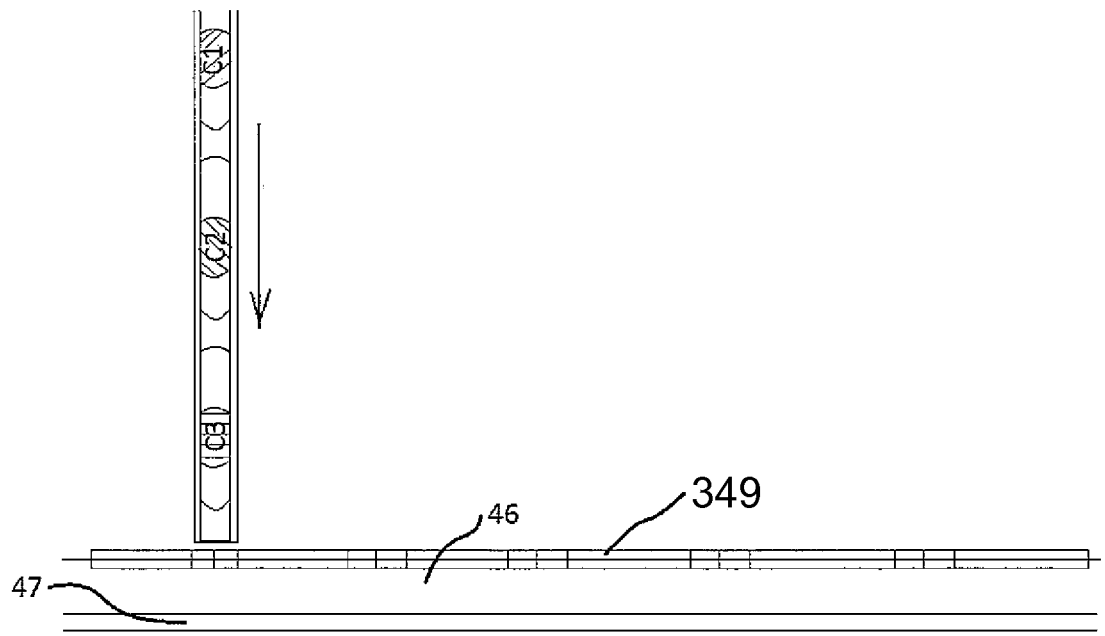
FIGS. 27A-27B schematically illustrate positioning of composite liquid cells at discrete locations along a hydrophobic spar with stabilisation features using a control tube and variable flow direction.
Figure 27B:
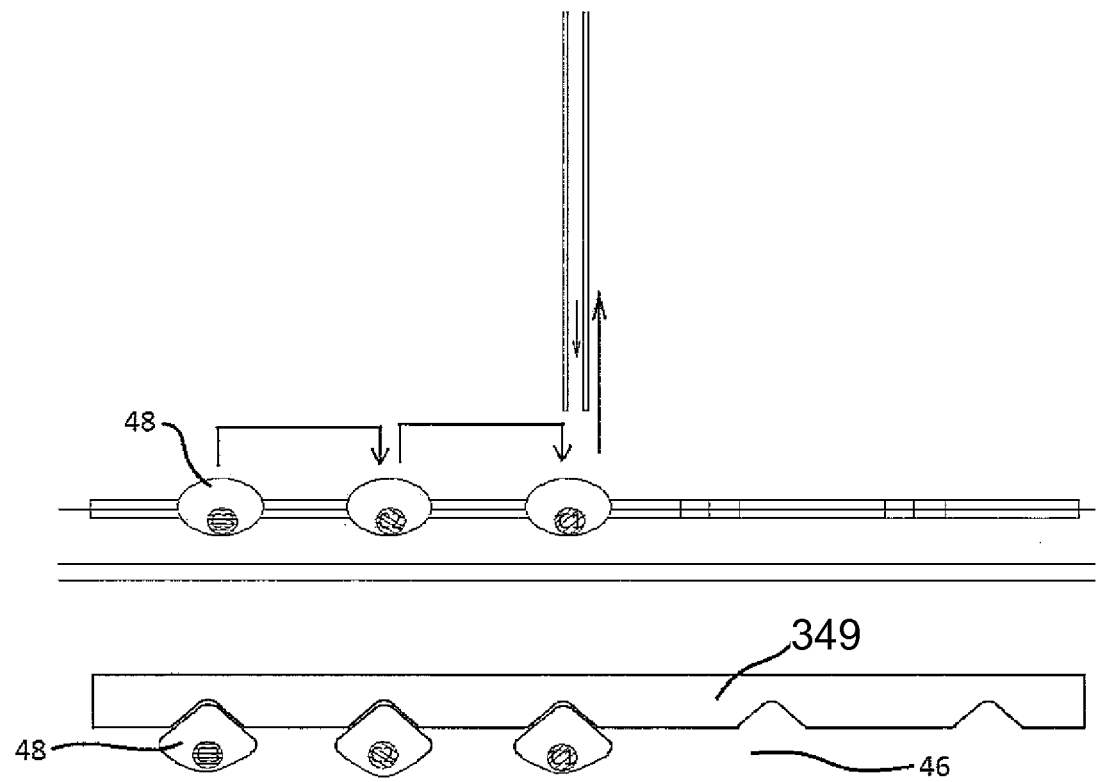

Composite liquid cells may be generated as described earlier, for example, FIGS. 4A-D. Referring to FIG. 27A the control tube is positioned over the carrier oil layer 46 housed in a biocompatible container 47. The control tube may either be in contact with or positioned between 0-3 mm above the free surface of the carrier oil 46. The flow direction is reversed in the control tube and immiscible fluid, sample and immiscible fluid are deposited on the free surface of the carrier oil, at a stabilisation feature on a hydrophobic spar 349, generating a composite liquid cell. Referring to FIG. 27B, upon depositing a complete composite liquid cell 48 the control tube translates to a new position along the hydrophobic spar 349 to deposit the next composite liquid cell at the stabilisation feature.

In another embodiment two or more hydrophobic surfaces with stabilisation features are used to control the composite liquid cell location. The use of stabilisation features on a hydrophobic spar allow for the generation of composite liquid cells at controlled and discrete locations, therefore improving sample tracking and/or automation and/or process control.

Transporting Composite Liquid Cells with Mechanical Features

Figure 29:
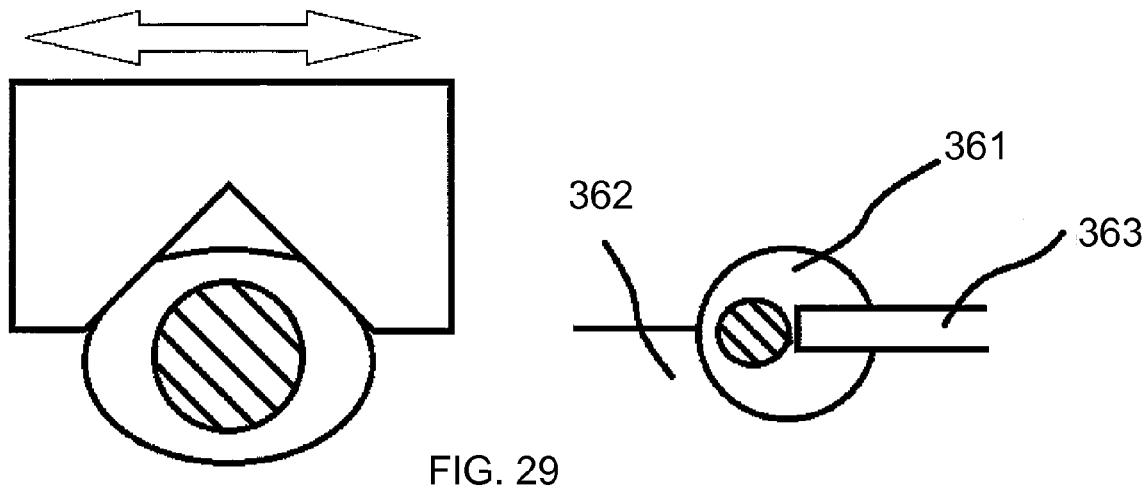
FIG. 29 schematically illustrate a transportation mechanism of a composite liquid cell using a hydrophobic control surface with a stabilisation feature.

In some embodiments, referring to FIG. 29 a composite liquid cell 361 positioned on a free surface of a mutually immiscible carrier fluid 362 can be transported using a control surface 363. The control surface 363 uses the hydrophobic effect to control the location of the composite liquid cell 361. Hydrophobic surfaces repel aqueous based media but silicon-based oils readily wet the surfaces permitting control using capillary tension. Bringing the control surface 363 into contact with the composite liquid cell 361 will result in a wetting of the surface of the body by the outer fluid of the composite liquid cell 361. The composite liquid cell can then be transported to a location on the carrier fluid 362 by translating the control surface 363. Using this transport motion, one or more composite liquid cells can be merged or additional biological samples can be added to a composite liquid cell.

Figure 30A:
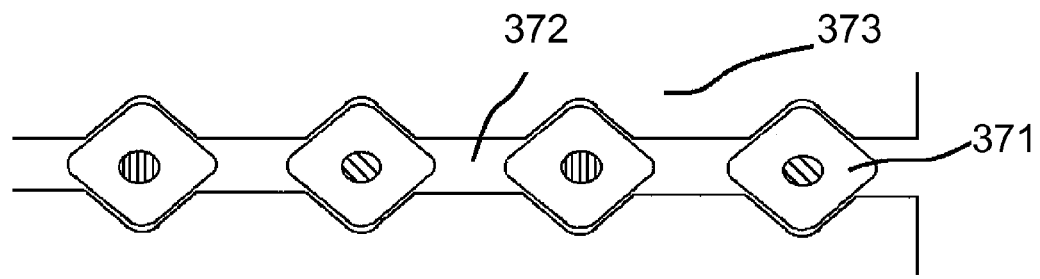
FIGS. 30A and 30B schematically illustrate a transportation mechanism for an array of composite liquid cells using hydrophobic stabilisation features.
Figure 30B:
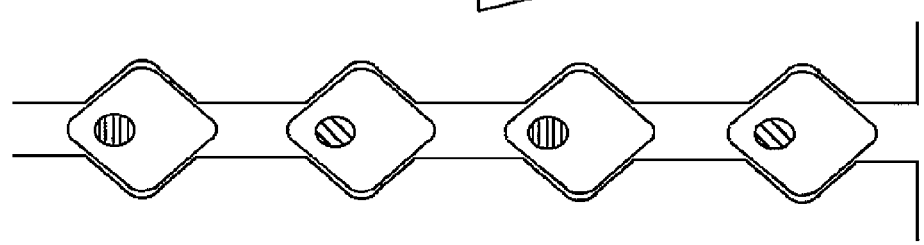

In some embodiments referring to FIGS. 30A and 30B, an array of composite liquid cells 371 positioned on a free surface of a mutually immiscible carrier fluid 372 can be transported using the control surface 373. The control surface 373 uses the hydrophobic effect to control the location of the composite liquid cells 371. Hydrophobic surfaces repel aqueous based media but silicon-based oils readily wet the surfaces permitting control using capillary tension. The control surfaces 373 are separated by no more than 0.5 times the sample diameter to ensure sample location confinement. The composite liquid cell array 371 is transported to a location on the carrier fluid 372 by translating the control surface 373. Using this transport motion with the stabilisation features the composite liquid cells can be processed individually, ensuring accuracy in the sample throughout discrete locations and/or referencing of the stabilisation feature location. This embodiment prevents uncontrolled merging and/or loss of sample.

Composite Liquid Cell Network

Referring to FIG. 31 a composite liquid cell network consists of at least two stabilisation regions 381 with a connection region 382. Each stabilisation region allows for the generation, and/or location control, and/or movement control, and/or mixing, and/or splitting, and/or processing of biological samples 383 within a composite liquid cell 384 and positioned on an immiscible carrier fluid 385.

In some embodiments referring to FIGS. 32A-32F a composite liquid cell network is used to transport a composite liquid cell. Referring to FIG. 32A a composite liquid cell 391 on a carrier oil 392 is located with a set of hydrophobic spars with stabilisation features 393. Referring to FIG. 32B a control tube 394 is positioned at/or in the region of the location to which the composite liquid cell 391 is to be moved. The control tube 394 is positioned above the free surface of the carrier fluid 392 and begins infusing immiscible encapsulating buffer fluid 395. Referring to FIG. 32C the encapsulating fluid 395 moves through the network and merges with the composite liquid cell 391. The control tube 394 is stopped and the flow direction reversed. Referring to FIG. 32D the composite liquid cell moves from the original stabilisation feature location to the new prescribed location. Referring to FIG. 32E when the composite liquid cell is at the new location the flow in the control tube 394 is stopped and removed. Referring to FIG. 32F the composite liquid cell has been transported to a new location for processing.

In another embodiment, two or more composite liquid cells can be transported simultaneously using a controlled injection and withdrawal of encapsulating buffer fluid.

Figures 33A, 33B, 33C, 33D, 33E:
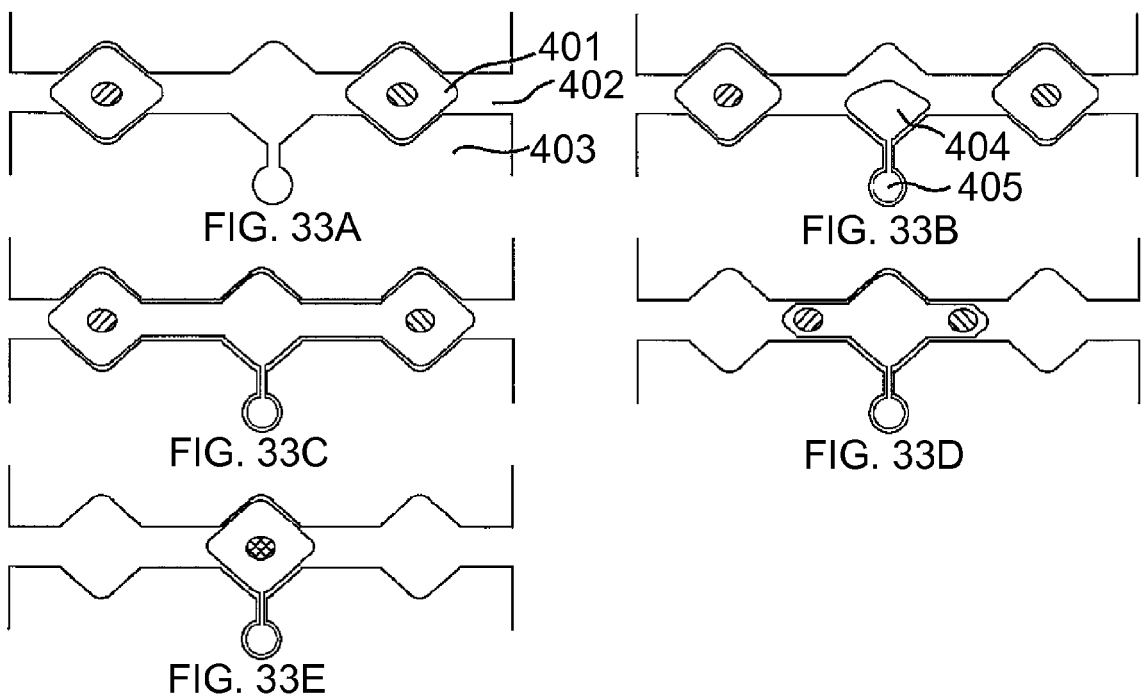
FIGS. 33A-33E are diagrams illustrating a mixing process of composite liquid cells within a composite fluid network.

In another embodiment, referring to FIGS. 33A-33E, a composite fluid network is used to transport and merge two composite liquid cells. Referring to FIG. 33A a composite liquid cell 401 on a carrier fluid 402 is located within a hydrophobic structure 403. Referring to FIG. 33B an immiscible encapsulating buffer fluid 404 is injected onto the carrier fluid 402 at control location 405. Referring to FIG. 33C the immiscible encapsulating buffer fluid 404 moves through the network and merges with the composite liquid cells 401. The infusion of immiscible encapsulating buffer fluid 404 is stopped. Referring to FIG. 33D the immiscible encapsulating buffer fluid 404 is withdrawn from control location 405 with the internal samples moving from their original locations to a new location. Referring to FIG. 33E when the samples are in the new location the immiscible encapsulating buffer fluid 404 flow at control location 405 is stopped. The samples merge resulting in a single sample composite liquid cell. The formation of complex encapsulating oil interfaces, bounded by control surfaces, carrier oil and an air interface, is governed by free surface energy which is proportional to the surface area of the encapsulating oil/air interface. Controlled withdrawal of encapsulating oil will cause the system to minimize surface area resulting in encapsulating oil being removed from the network extremities equally. This interfacial contraction from the network's extremities also transports aqueous droplets contained within.

Figure 34A:
FIGS. 34A and 34B are photographs showing merging of two composite liquid cells within a composite fluid network.

FIG. 34A is a picture of a composite fluid network with two composite liquid cells. The composite liquid cells in this picture contain 2.5 micro-liters sample volumes of distilled water, one sample dyed red and the second dyed blue. The encapsulate buffer fluid was an immiscible fluid Phenylmethylpolysiloxane—PD5 oil on an immiscible fluorocarbonated carrier—FC40. The hydrophobic spar was a PTFE based material which was located on the interface of the carrier fluid and air. The stabilisation features have a dimension of approximately 2 mm at the widest and an angle of approximately 45 degrees.

Figure 34B:
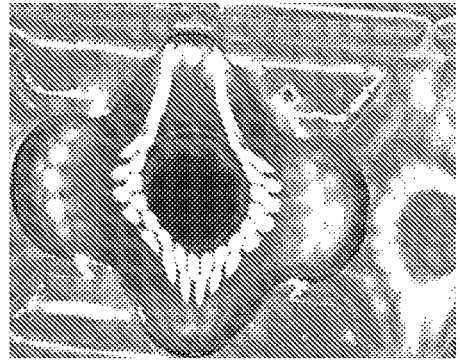
Figure 35A:
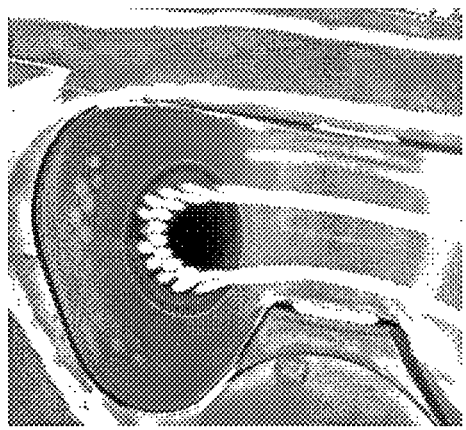
FIGS. 35A-35C are photographs showing merging of two composite liquid cells to generate a multi-sample composite liquid cell within a composite fluid network.
Figure 35B:
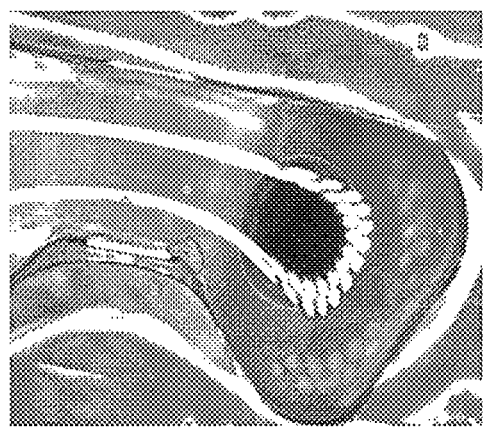
Figure 35C:
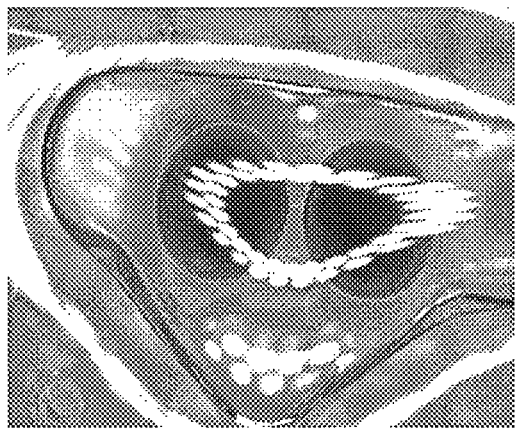
Figure 36A:
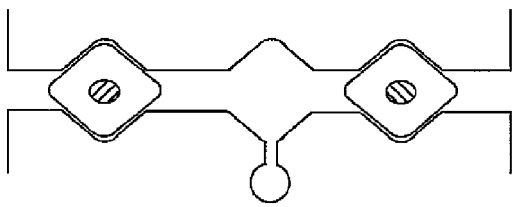
FIGS. 36A-36E schematically illustrate a mixing process of composite liquid cells to generate a multi-sample composite liquid cell within a composite fluid network.
Figure 36B:
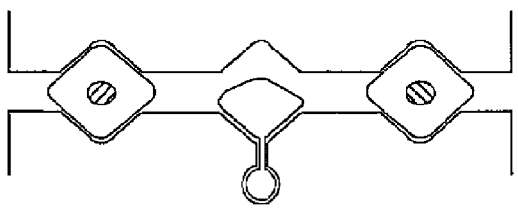
Figure 36C:
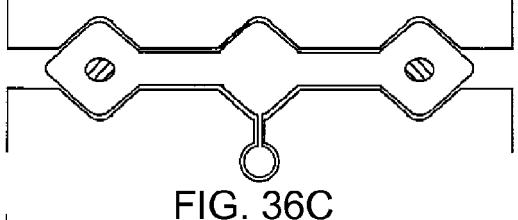
Figure 36D:
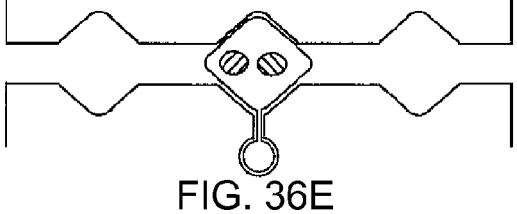
Figure 36E:
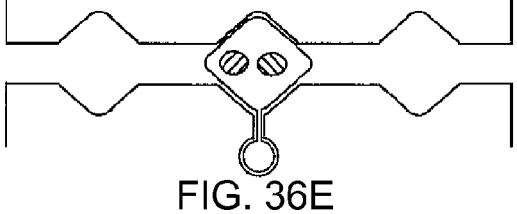

FIG. 34B shows a single composite liquid cell with a single internal sample, which is a result of the merging of the previous two composite liquid cell sample volumes by the method described previously.

Referring to FIGS. 35A-35C and 36A-36E, the encapsulating fluid has an additive and the merging of composite liquid cells results in a multi-sample composite liquid cell.

Figure 37A:
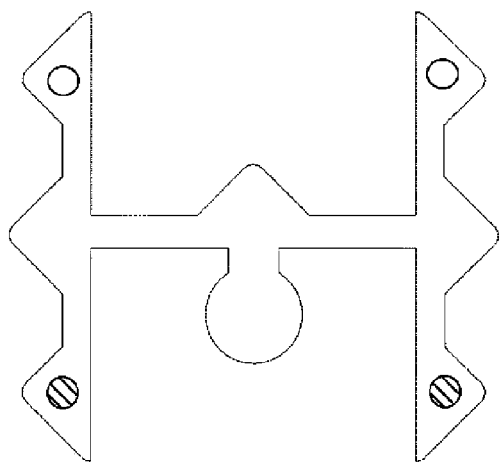
FIGS. 37A-37C schematically illustrate a composite fluid network for four composite liquid cells to be combined in two stages.
Figure 37B:
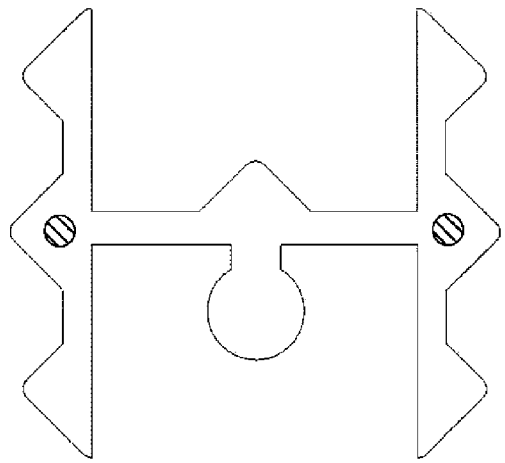
Figure 37C:
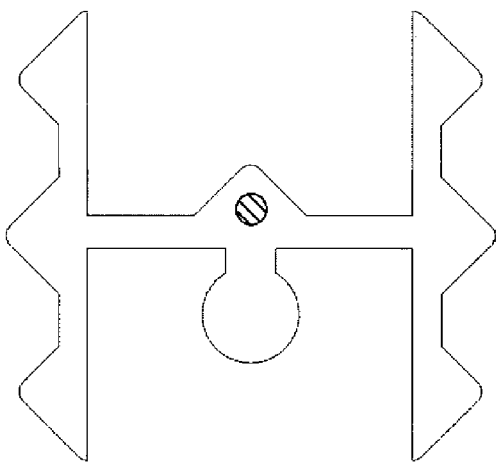

Examples of composite liquid cell networks are outlined herein but are not limited to these; Referring to FIGS. 37A-37C, a composite liquid cell network for merging four composite liquid cells in two stages. Referring to FIG. 37B the composite liquid cells in the adjoining stabilisation features merge first. Referring to FIG. 37C the remaining composite liquid cell samples are merged resulting in a single composite liquid cell.

Figure 38A:
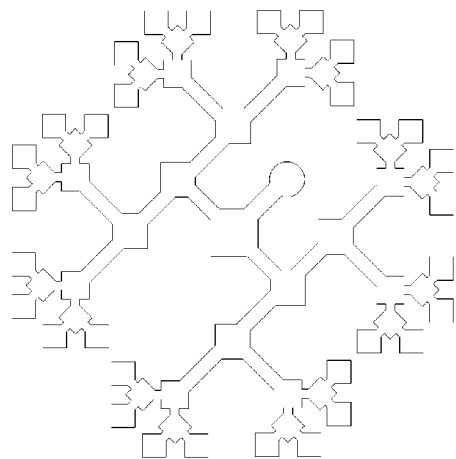
FIGS. 38A-38G schematically illustrate a composite fluid network for 32 composite liquid cells to be combined in five stages.
Figure 38B:
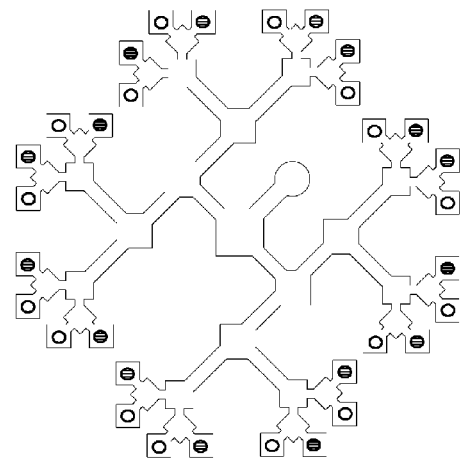
Figure 38C:
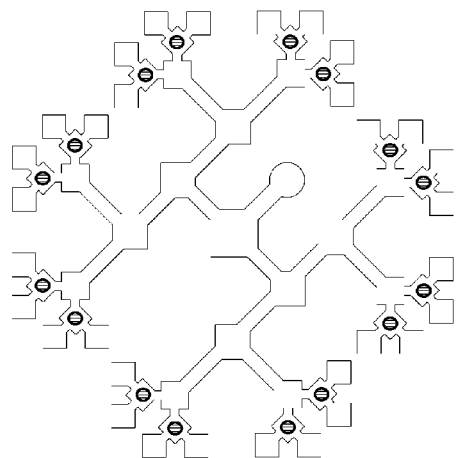
Figure 38D:
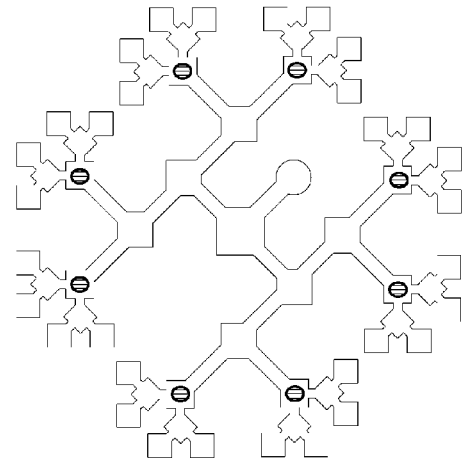
Figure 38E:
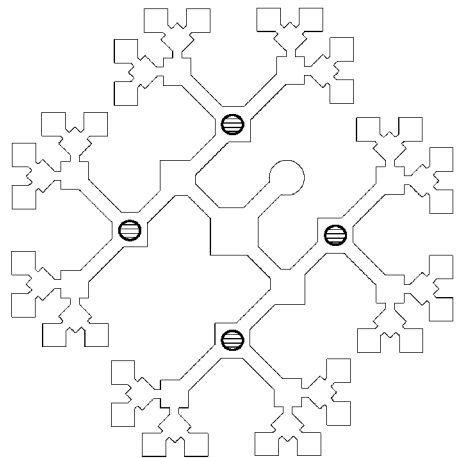
Figure 38F:
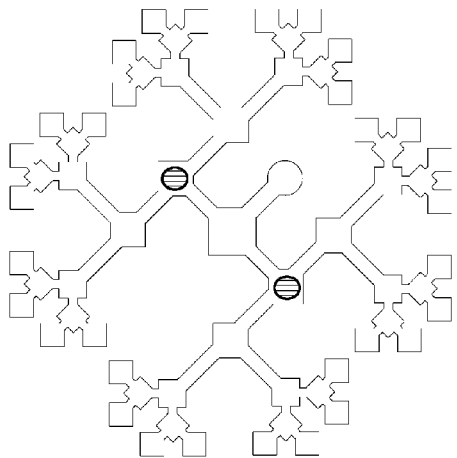
Figure 38G:
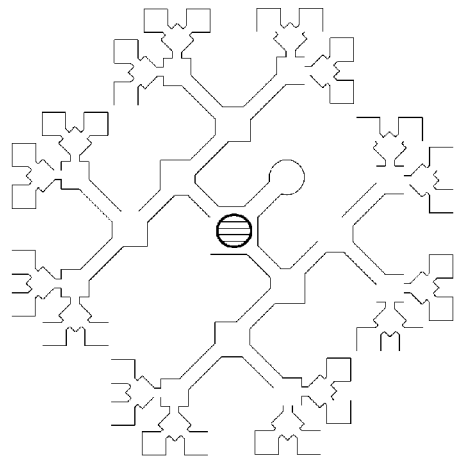

Another example, referring to FIGS. 38A-38G, is a network for merging 32 composite liquid cells in 5 stages. Referring to FIG. 38A a network of hydrophobic spars and carrier oil prior to composite liquid cell loading. Referring to FIG. 38B composite liquid cells are loaded in the outer locations of the composite fluid network. Referring to FIG. 38C the composite liquid cells in the adjoining stabilisation features are merged using an infusion/withdrawing process of the immiscible buffer encapsulating fluid. Referring to FIG. 38D the second stage of the composite liquid cell processing—the composite liquid cells in the adjoining stabilisation features are merged using an infusion/withdrawing process of the immiscible buffer encapsulating fluid. The composite liquid cells now contain four of the originally deposited composite liquid cells. Referring to FIG. 38E the third stage of the composite liquid cell processing—the composite liquid cells in the adjoining stabilisation features are merged using an infusion/withdrawing process of the immiscible buffer encapsulating fluid. The composite liquid cells now contain eight of the originally deposited composite liquid cells. Referring to FIG. 38F the fourth stage of the composite liquid cell processing—the composite liquid cells in the adjoining stabilisation features are merged using an infusion/withdrawing process of the immiscible buffer encapsulating fluid. The composite liquid cells now contain sixteen of the originally deposited composite liquid cells. Referring to FIG. 38G the fifth stage of the composite liquid cell processing—the composite liquid cells in the adjoining stabilisation features are merged using an infusion/withdrawing process of the immiscible buffer encapsulating fluid. The composite liquid cells now contain all thirty two of the originally deposited composite liquid cells. At each of the stages biological processing of the composite liquid cells can be performed. These processes may include but are not limited to; polymerase chain reaction, and/or thermal cycling, and/or isothermal amplification, and/or optical analysis, and/or the addition of further reagents.

Figure 41A:
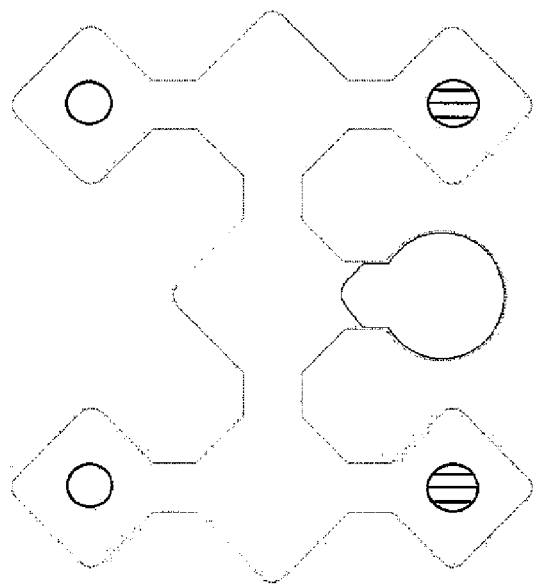
FIGS. 41A-41D are diagrams illustrating generation of a composite fluid network.
Figure 41B:
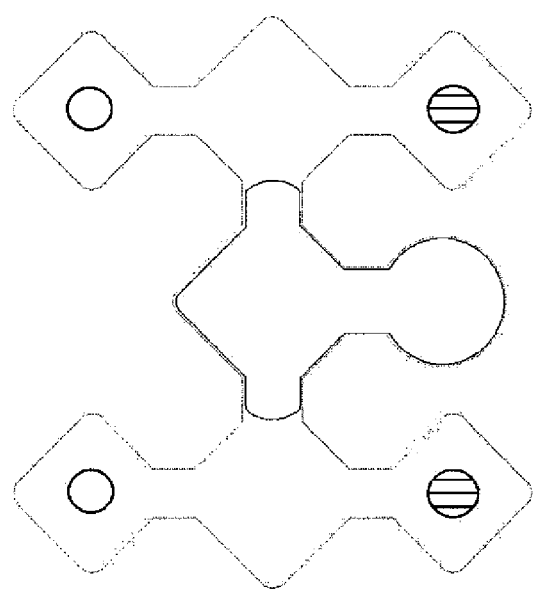
Figure 41C:
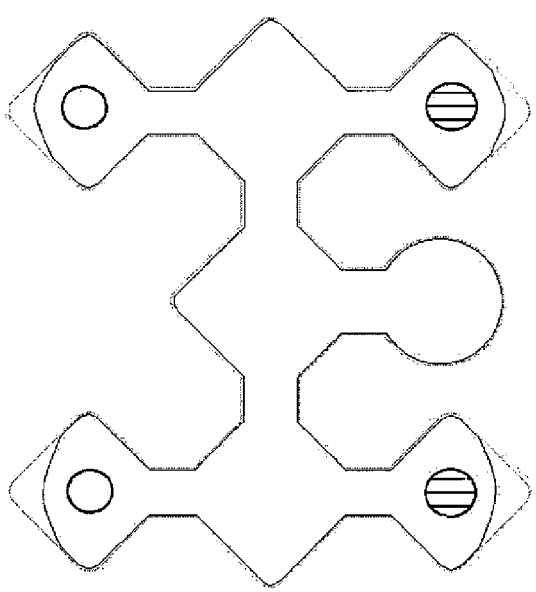
Figure 41D:
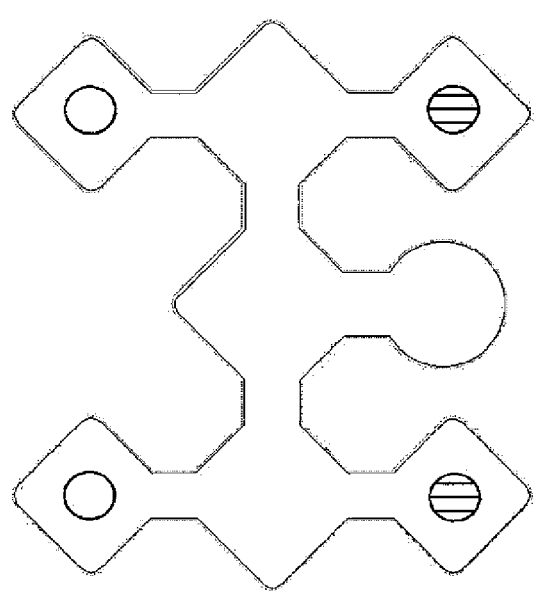

In another embodiment, referring to FIGS. 41A-41D, a composite fluid network is generated using a method of infusing the immiscible encapsulating buffer fluid. Referring to FIG. 41A the target samples are dispensed within the network of hydrophobic spars on the carrier fluid. Referring to FIG. 41B the immiscible encapsulating buffer fluid is infused on the carrier fluid. Referring to FIG. 41C the immiscible encapsulating buffer fluid encapsulated the sample volumes within the stabilisation features of the hydrophobic spars. Referring to FIG. 41D one embodiment of the composite fluid network is shown.

Figure 42A:
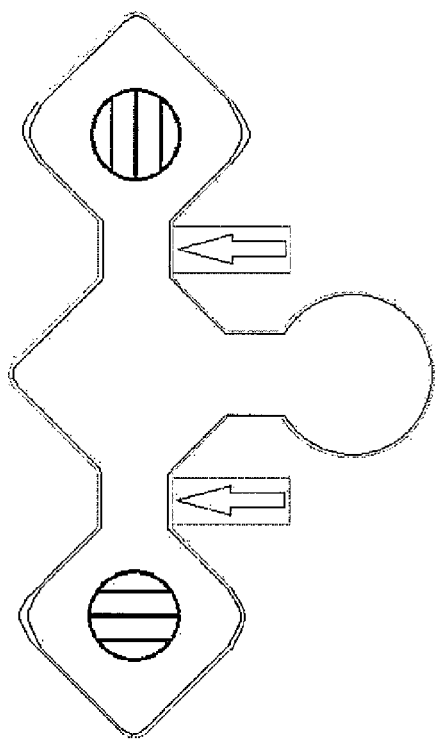
FIGS. 42A-42D is a diagram illustrating a hydrophobic control surface for immiscible buffer encapsulating fluid path control.
Figure 42B:
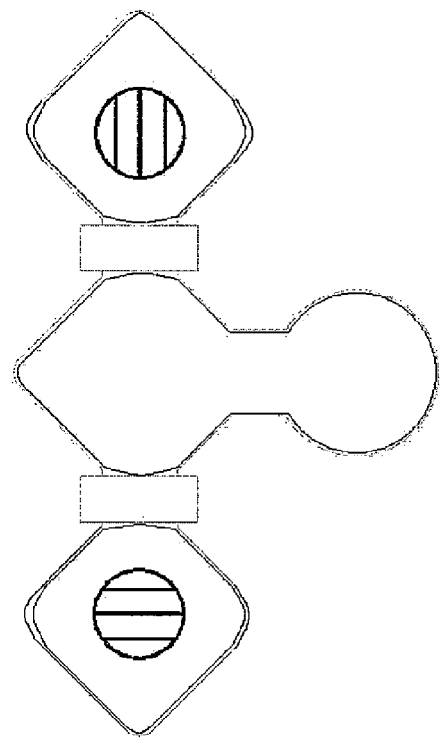
Figure 42C:
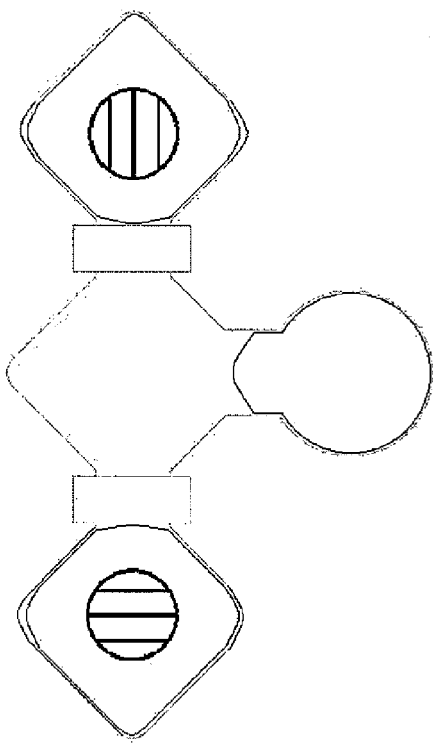
Figure 42D:
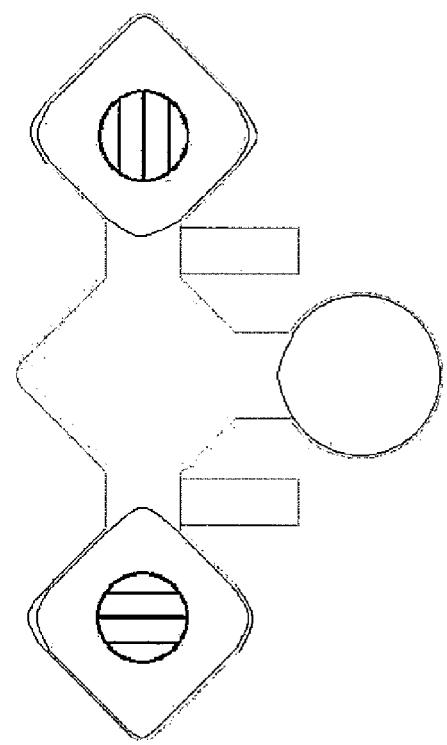
Figure 43:
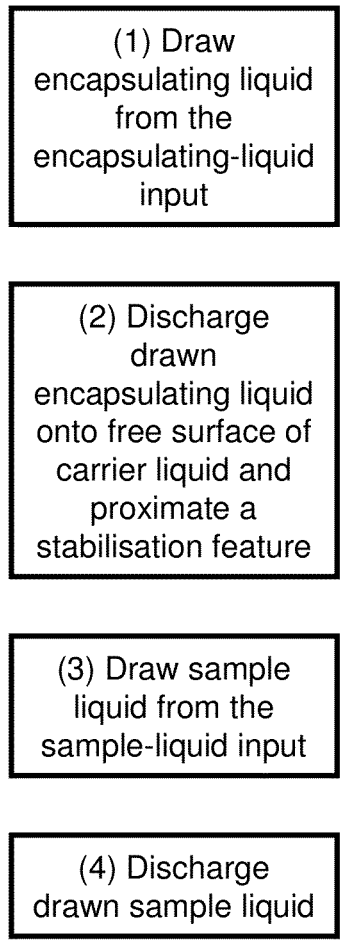
FIGS. 43-47 illustrate various methods that can be implemented as controller programming.

In another embodiment, referring to FIGS. 42A-42D, the composite fluid network has hydrophobic control surfaces to control the immiscible encapsulating buffer fluid network path on the carrier fluid. Referring to FIG. 42A a composite fluid network with two samples at discrete stabilisation features within an immiscible encapsulating buffer fluid. Referring to FIG. 42B hydrophobic control surfaces are used to shear the immiscible encapsulating buffer fluid, while maintaining a carrier fluid path. Referring to FIG. 42C the immiscible encapsulating buffer fluid can be withdrawn. Referring to FIG. 42D two discrete composite liquid cells are generated. This method is also used to progress a composite liquid cell through a composite fluid network and/or to isolate a composite liquid cell from other processes within the composite fluid network.

Processing the Composite Liquid Cells

In certain embodiments, the system may involve one or more of the following steps in any order which achieves the target sample combination at the end of the method: extracting samples for target; processing the samples for loading into the dispensing system; dispensing the target sample; dispensing the immiscible encapsulating fluid cell; dispensing the carrier fluid; combining the biological sample and immiscible encapsulating fluid cell; combining the biological sample and composite liquid cell; combining the biological sample and multi-sample composite liquid cell; controlling the motion of the immiscible encapsulating fluid cell; controlling the motion of the carrier fluid; transporting one or more immiscible fluid cells; transporting one or more immiscible fluid cells to combine with one or more biological samples; transporting one or more composite liquid cells to combine with one or more biological samples; transporting one or more multi-sample composite liquid cells to combine with one or more biological samples; transporting one or more composite liquid cells to combine with one or more composite liquid cells; transporting one or more multi-sample composite liquid cells to combine with one or more composite liquid cells; transporting one or more multi-sample composite liquid cells to combine with one or more multi-sample composite liquid cells; detecting an effect of the biological sample within the composite liquid cell; detecting an effect of the biological sample within the multi-sample composite liquid cell; detecting effects of biological samples within the multi-sample composite liquid cell; providing output information to a user of the detection; analysing the output data of the detection. Examples of the biological protocols are given in the ensuing sections.

PCR

Polymerase Chain Reaction (PCR) has been used extensively to amplify targeted DNA and cDNA for many applications in molecular biology. The PCR technique amplifies a single or a few copies of a piece of DNA, generating thousands to billions of copies of a particular DNA sequence. Modem PCR instruments carry out the PCR process in reaction volumes ranging from 10-200 micro-liters. One of the largest obstacles to carrying out PCR in small volumes is the difficulty in manipulating small volumes of the constituent reagents with manual pipettes. Another obstacle for PCR is the difficulties in multiplexing reactions allowing for increased thought put.

The methods of the invention generally involve combining the necessary fluids to form the resulting multi-sample composite liquid cell. In one embodiment the target sample is an aqueous biological sample, comprising reagents required for nucleic acid amplification, and the outer fluid cell is a silicone oil (Phenylmethylpolysiloxane, PD 5) with a polysorbate additive (SPAN 80), on a carrier fluid which is a fluorocarbon-based oil (Fluorinert FC-40). The individual reagents are arrayed such that all the necessary components for PCR are placed as individual composite liquid cells. This prevents cross-contamination of biological reagents. The individual composite liquid cell components are combined together in the correct sequence. The individual composite liquid cells are then combined together forming a multi-sample composite liquid cell. The multi-sample composite liquid cell is then transported into different thermal zones or optical interrogation zones where quantitative measurement of the products are performed via fluorescent measurement. The placement of PCR target volumes within composite liquid cells prevents evaporation during thermal cycling. Typical thermal cycling temperatures range between 55-95° C.

In a further embodiment the composite liquid cells may have an associated detection mark added as a discrete sample.

In a further embodiment, the combination of post-PCR reactions may be required for further processing that may include genetic sequencing. The use of multi-sample composite liquid cells greatly simplifies the collection and sequencing procedure for these relatively small target volumes. The multi-sample composite liquid cells following individual processing can be combined selectively, removing any unspecific amplification reactions or inefficient reaction from the final collected volume. The amalgamated final target volume, consisting of many differing target molecules, is transferred into a sequencing instrument for detailed analysis. The composite liquid cell facilitates 100% volume retrieval as the biological sample is processing and does not need to touch any solid surface and also has the additional benefit of an anti-wetting characteristic. Additionally, the fluid volume requiring thermal cycling has been greatly reduced—removed the entire mass and thermal resistance of the static well plates—targeted heating strategies can facilitated lower power instruments and faster reaction processing times.

TABLE 1

Fluorescence intensity results showing the ability to detect Single Nucleotide
Polymorphisms in composite liquid cell with no carryover contamination

| | FAM READINGS | | | | | RED READINGS | | | | |
|---|---|---|---|---|---|---|---|---|---|---|
| < > | NTB 1 | Allele 1 | NTB 2 | Allele 2 | NTB 3 | < > | NTB 1 | Allele 1 | NTB 2 | Allele 2 | NTB 3 |
| A | 3776 | 34503 | 3492 | 4579 | 2916 | A | 3489 | 3460 | 3291 | 14928 | 2685 |

Referring to Table 1 the composite liquid cell has successfully performed Single Nucleotide Polymorphism detection. Two positive samples were used, each containing a different allele of the gene, named allele 1 and allele 2. Each allele was labelled with a different dye and reading at the correct intensity allowed detection of each allele. A no template control was added in a composite liquid cell and amplified. This was repeated in the following order for a positive allele 1, a no template control, a positive allele 2 and finally another no template control. Referring to Table 1 the results show that amplification was successfully performed in composite liquid cells with no cross contamination between samples. This is indicated by no rise in fluorescence intensity between the initial no template control and the no template control samples that followed each positive samples.

Figure 39:
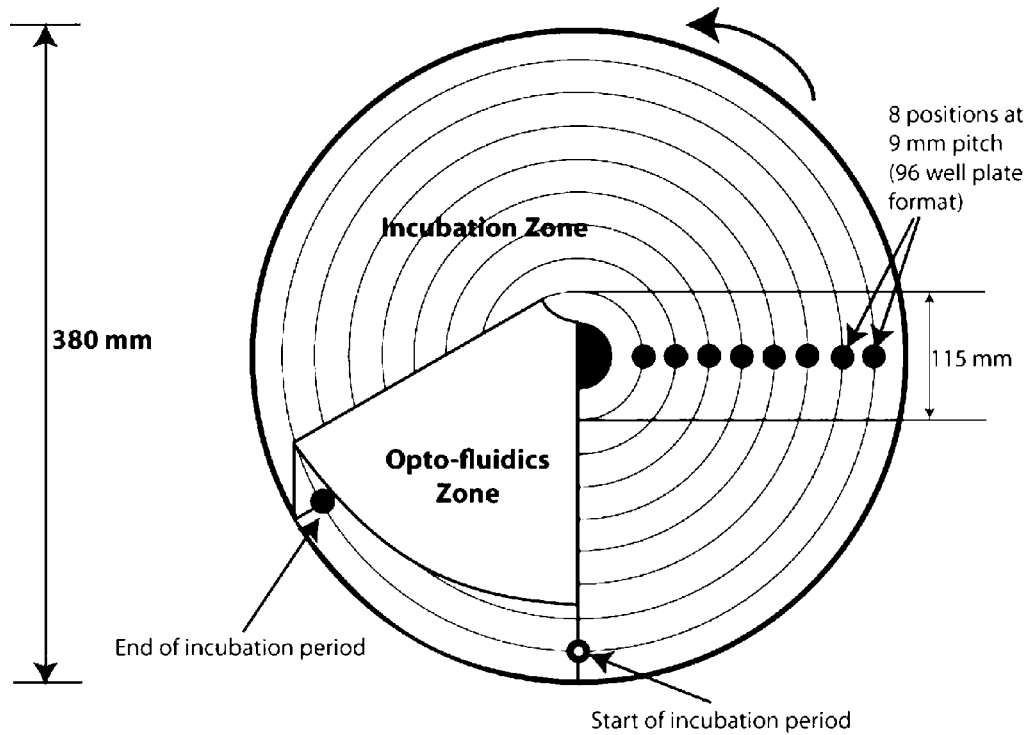
FIG. 39 schematically illustrates a composite liquid cell apparatus for isothermal nucleic acid amplification.
Figure 39:
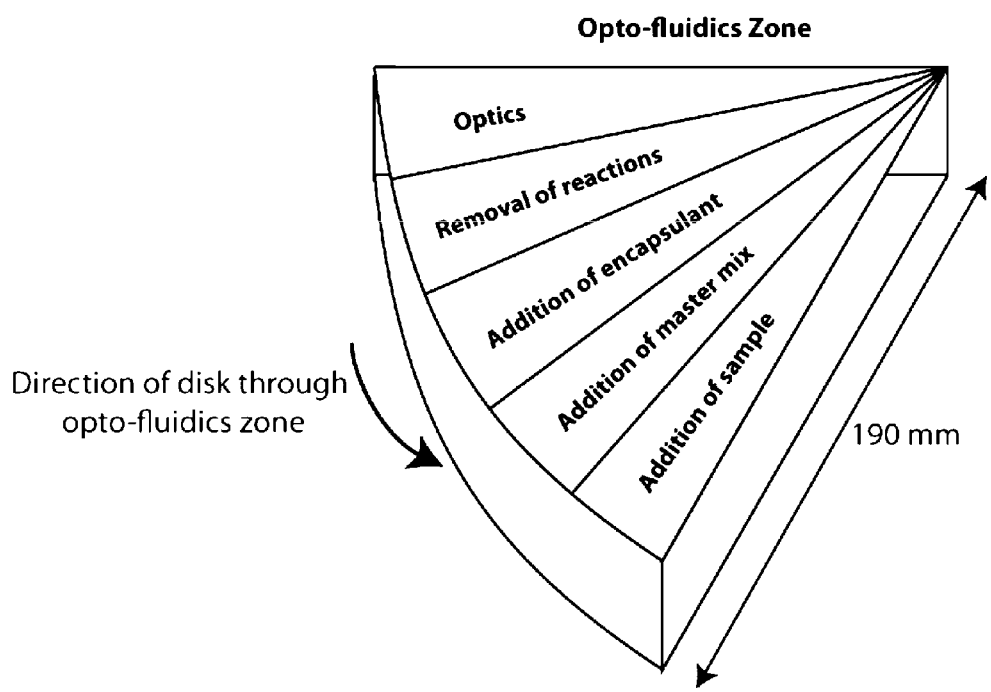

Referring to FIG. 39 an apparatus for an isothermal nucleic acid amplification of multiple composite liquid cells. The composite liquid cells are arrayed on a circular platform which moves through the required stages of composite liquid cell generation, thermal processing, optical detection and removal. The composite liquid cell generation has three stages, the addition of the immiscible encapsulating buffer fluid to the carrier fluid, the addition of the master PCR reagents to the immiscible encapsulating buffer fluid and the addition of the sample to the composite liquid cell. The composite liquid cell is then biologically processed by heating to 65° C. for 10 minutes. To complete the rotation of the hydrophobic plate, the composite liquid cells pass though a fluorescent detection region after which the composite liquid cells are removed from the carrier fluid and the platform returns to the initial composite liquid cell generation stage. The plate continuously rotates with new composite liquid cells generated at a speed dependant on the rotation speed of the platform.

Figure 40:
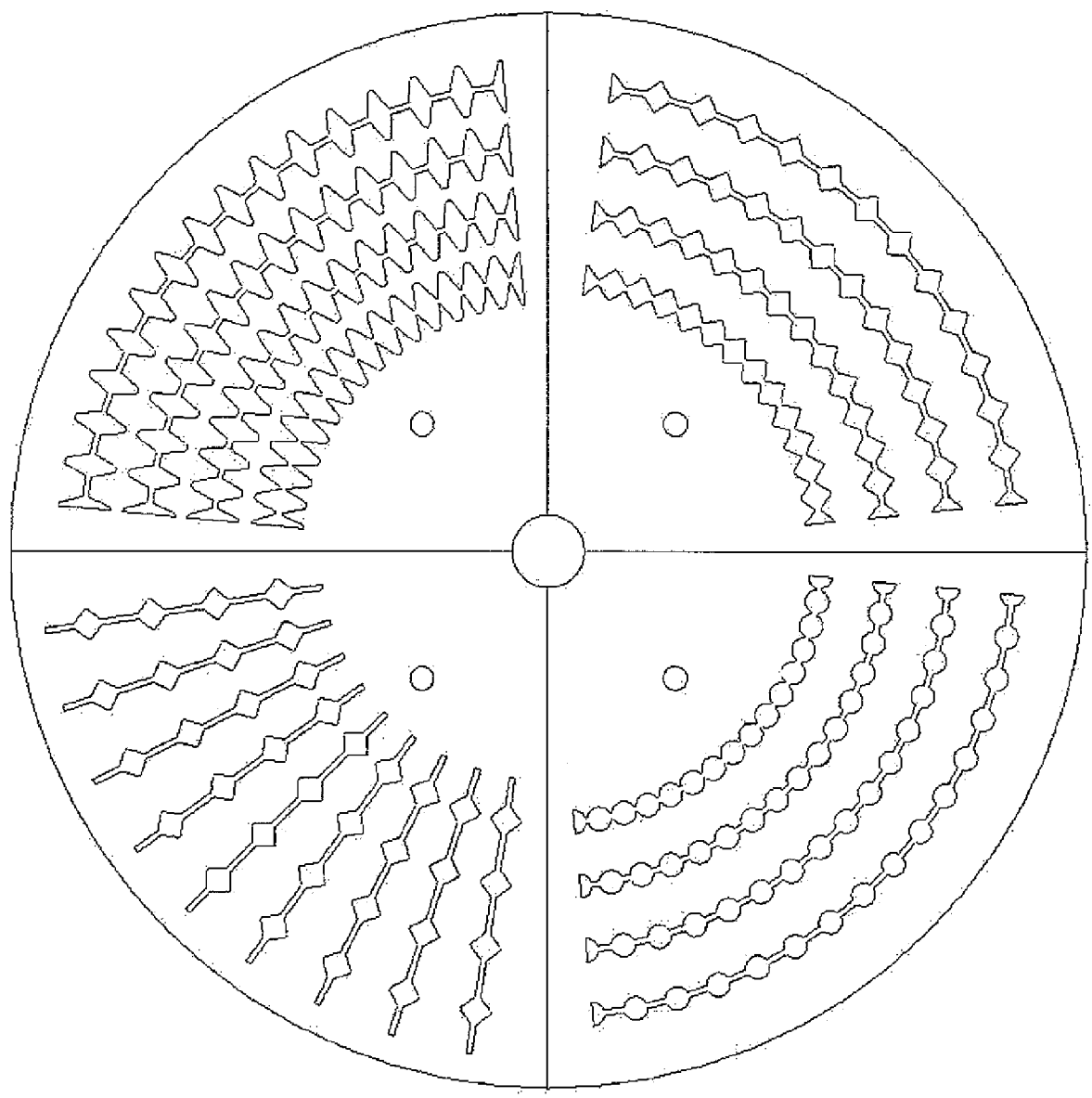
FIG. 40 schematically illustrates a range of stabilisation features on a disc-shaped hydrophobic platform.
Figure 40A:
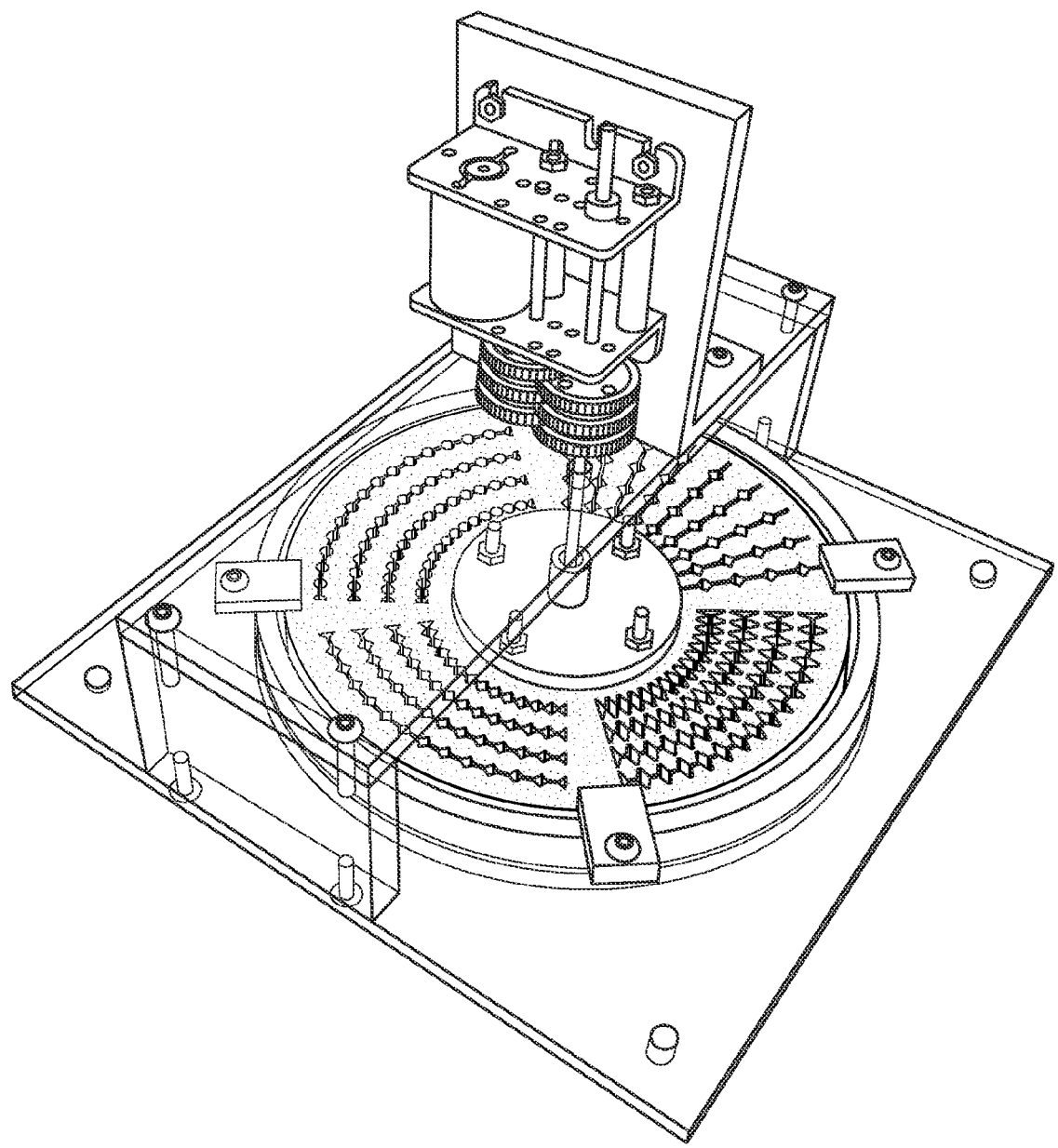
FIG. 40A shows an exemplary system using the disc-shaped platform.

FIG. 40 shows an example of a disc-shaped platform, typically of a hydrophobic material, that provides a network of stabilisation features. FIG. 40A shows the disc incorporated in a system. The system has a stationary circular bath of carrier liquid. Rotating on the surface of this carrier oil bath is a PTFE disk containing stabilization features. The disc may be rotated by a shaft driven by the motor-gearbox assembly shown. Composite liquid cells may be dispensed into the stabilisation features from a fixed dispensing tube (not shown).

Digital PCR

The Polymerase Chain Reaction (PCR) is a widely used molecular amplification technique. The technique has widespread applications in clinical diagnostics, agricultural biotechnology and bioresearch. It is routinely used for the detection of SNP's, diagnosis of hereditary diseases, genetic fingerprinting, forensic analysis, gene expression and other types of nucleic acid analysis. The development of Digital PCR has increased the use of conventional PCR. Digital PCR is a technique that amplifies a single DNA template. For a review of the PCR methodology see Digital PCR (Proc Natl Acad Sci USA 96(16):9236-41 (1999)) by Vogelstein and Kinzler; Principle and application of digital PCR (Expert Review Molecular Diagnostics 4(1):41-47 (2004)) by Pohl and Shih.

The methods of the invention generally involve combining and distributing the necessary fluids to form the resulting multi-sample composite liquid cell. In one embodiment the target sample is an aqueous biological sample, comprising reagents required for nucleic acid amplification, and the outer fluid cell is a silicone oil (Phenylmethylpolysiloxane, PD 5) with a polysorbate additive (SPAN 80), on a carrier fluid which is a fluorocarbon-based oil (Fluorinert FC-40). The individual reagents are arrayed such that all the necessary components for digital PCR are placed as individual composite liquid cells. This prevents cross-contamination of biological reagents. The individual composite liquid cell components are combined together in the correct sequence. The individual composite liquid cells are then ultrasonicated to form a multi-sample composite liquid cell. The multi-sample composite liquid cell is then transported into different thermal zones or optical interrogation zones where quantitative measurement of the products are performed via fluorescent measurement. The placement of digital PCR target volumes within composite liquid cells prevents evaporation during thermal cycling. Typical thermal cycling temperatures range between 55-95° C. The multi-sample composite liquid cell facilitates the use of simpler detection methods as the multi-sample composite liquid cell does not require optics for three dimensional integration for quantification determination.

In another embodiment the individual composite liquid cells are mechanically agitated to form a multi-sample composite liquid cell.

Nucleic Acid/DNA Ligation

Nucleic acid ligation involves the use of nucleic acid ligases, which are enzymes that are used to join fragments of nucleic acid together. In constructing long DNA strands multiple shorter DNA fragments are combined together, it is therefore necessary to perform multiple ligation steps to achieve these results. The product of one ligation reaction becomes the fragment of another. The ligation must be performed in a pairwise fashion to avoid efficiency and orientation problems affecting the reaction.

In one embodiment, the reaction reagents—the DNA fragments to be joined; the ligase enzyme; and the buffer reagents—are pipetted individually into separate wells of a microtitre plate. The outer composite fluid, a silicone oil (Phenylmethylpolysiloxane, PD 5), is pipetted on top of the aqueous reagents within each well, creating an oil-aqueous interface.

A hydrophobic sampling capillary manipulated by an automated robotic platform, aspirates a volume of oil, in the range of 500-2000 nanoliters of silicone oil (Phenylmethylpolysiloxane, PD 5) from the first sampling well, followed by aspirating 100-700 nl of the target volume (aqueous reagents), followed by a similar volume of silicone oil (Phenylmethylpolysiloxane, PD 5) in the range of 500-2000 nanoliters. The sampling capillary then translates through the air, still aspirating, into the next sampling well. The procedure is repeated for the next sampling well, aspirating the covering oil, followed by the aqueous reagents, followed by the covering oil. The hydrophobic sampling capillary tube then translates until a predetermined number of samples have been aspirated. The hydrophobic sampling capillary now has a series of discrete liquids segmented by air, aspirated during translation.

The hydrophobic sampling capillary tube is translated over the processing platform. The direction of flow in the hydrophobic sampling capillary tube is reversed to dispense each fluid sequence as an individual composite liquid cell on to the surface of a carrier oil, a fluorocarbon-based oil (Fluorinert FC-40). The hydrophobic sampling capillary tube is translated between discreet liquid dispensing to a new composite liquid cell initial location. The composite liquid cells are dispensed such that they interface with a hydrophobic spar which secures the composite liquid cells location. The sequence of composite liquid cells combining to give the final DNA synthetic construction is placed on a single hydrophobic spar. The dispensing process generates a series of composite liquid cells separated by a distance in the range of 0.5 mm-10 mm, positioned on hydrophobic spars.

In the case of single-sample composite liquid cells, a control surface manipulated by an automated robotic platform creates a pairwise combinations of composite liquid cells such that the reagents within composite liquid cells combine and mix via the action of capillary tension with the control surface. Or, if a fluid cell network is being used, then the injection/withdraw immiscible encapsulating buffer fluid controls of the composite fluid network make pairwise combinations of composite liquid cells such that the reagents within composite liquid cells combine and mix.

These reagents contain the neighbouring DNA fragments and other reagents necessary for ligation to occur. The composite liquid cells are controlled at specific temperature conditions for a specific time for ligation to occur. Typical conditions are 16° C. for 1 hour to ensure ligation of cohesive-ended fragments. After this ligation step, further pairwise combinations of neighbouring composite liquid cells are formed and processed at the correct temperature generating longer fragments. This process is repeated until the desired final fragment length is reached. The newly constructed synthetic DNA strand is then aspirated and stored for future use.

The creation of composite liquid cells greatly simplifies the method of DNA ligation. The smaller reaction volume, not normally used in this process ensures higher reaction efficiency and faster reaction times. The combination of target DNA strand fragments for each ensuing pairwise ligation is greatly simplified and the number of overall liquid manipulations is greatly reduced, as the entire sequence of target DNA composite liquid cells are co-located on the hydrophobic spar network. Coalescence by this method is easy to achieve by manipulating the position of the composite liquid cells. This method of ligation is particularly useful where the products of one ligation step are necessary for another step.

The use of composite liquid cells greatly simplifies the collection procedure for these relatively small target volumes. The composite liquid cells following individual processing can be combined selectively, removing any non-reactive sample or inefficient reactions from the ligation process. The composite liquid cell facilitates 100% volume retrieval as the biological sample in processing does not need to touch any solid surface and also has the additional benefit of an anti-wetting characteristic.

More particularly, multi-sample composite liquid cells may be used. The multi-sample composite liquid cells are controlled at specific temperature conditions for a specific time for ligation to occur. Typical conditions are 16° C. for 1 hour to ensure ligation of cohesive-ended fragments. Following ligation nucleic acid amplification is performed to selectively amplify the correct region of interest and next ligation step. After this step, internal samples are combined in a pairwise sequence, additional reagents are added if required and processed at the correct temperature generating longer fragments. This process is repeated until the desired final fragment length is reached. The newly constructed synthetic DNA strand is then aspirated and stored for future use.

The creation of multi-sample composite liquid cells greatly simplifies the method of DNA ligation. The smaller reaction volume, not normally used in this process ensures higher reaction efficiency and faster reaction times. The combination of target DNA strand fragments for each ensuing pairwise ligation is greatly simplified and the number of overall liquid manipulations is greatly reduced, as the entire sequence of target DNA samples are co-located within the one multi-sample composite liquid cell. Internal sample coalescence by this method is easy to achieve by manipulating the outer oil surface positions within the location features of the hydrophobic surface. This method of ligation is particularly useful where the products of one ligation step are necessary for another step.

Genetic Sequencing Bead Coating

Genetic sequencing bead preparation is a process by which small beads are coated in an application-specific chemistry. In one embodiment the coating of beads in advance of genetic screening is achieved by generating composite liquid cells with an aqueous solution of beads as the target volumes. The specific primer chemistry, used to coat the beads, is introduced into the fluid cell via a capillary depositing an aqueous droplet directly into the fluid cell, such that the target volumes combine, resulting in mixing and coalescence of the primer chemistry with the aqueous bead solution.

In another embodiment, there is creation of a composite liquid cell for the primer chemistry and then manipulation to coalesce with the composite liquid cell containing the aqueous bead solution, such that the target volumes combine and mix.

These methods provide for a convenient way of manipulating and combining sub-microliter volumes of fluid that is currently not possible to achieve using conventional techniques, thereby reducing the initial sample volumes and improving the bead coating efficiency by reducing the reaction volume. Further processing using PCR and thermal cycling and genetic sequencing is application-specific.

The use of composite liquid cells greatly simplifies the collection procedure for these relatively small target volumes. The composite liquid cells following individual processing can be combined selectively, removing any non-reactivated beads. The composite liquid cell facilitates 100% volume retrieval as the biological sample in processing does not need to touch any solid surface and also has the additional benefit of an anti-wetting characteristic. These features make automation of the biochemistry process easier to facilitate.

The invention is not limited to the embodiments described but may be varied in construction and detail. For example the encapsulating buffer fluid may be any suitable liquid or gas, most commonly a liquid. The carrier fluid may be any suitable liquid or gas, but most commonly a liquid. The choice of encapsulating and carrier fluid may be chosen such that the functional groups of the fluids result in mutual immiscibility that limits diffusion of carrier fluid molecules into the encapsulating fluid and vice versa. This immiscibility constraint must also apply between the encapsulating fluid and the target sample such that molecular diffusion is limited by the differing functional groups of the constituent fluids. For example the phenylmethyl functional groups present in phenylmethylpolysiloxanes (silicone oils) chosen for encapsulating fluids are immiscible with the perfluoro functional groups present in fluorocarbon based carrier oils that are commonly chosen as carrier fluids. These two oils are furthermore immiscible with aqueous based samples that are common in molecular biochemistry. It is also advantageous to choose fluids of differing densities such that the carrier fluid has the highest density and forms the lowest layer of fluid, the encapsulating fluid has the lowest density and the target sample has an intermediate density between that of the carrier fluid and the encapsulating fluid.

Embodiments

Some embodiments of the invention encompasses a sample handling system comprising a sample-liquid input, an encapsulating-liquid input, a carrier-liquid conduit comprising a stabilisation feature, a liquid-handling system, and a controller operably connected to the liquid-handling system. In some embodiments the controller may be programmed to: (1) draw an encapsulating liquid from the encapsulating-liquid input; (2) discharge the drawn encapsulating liquid (a) onto a free surface of a carrier liquid in the carrier-liquid conduit and (b) proximate to the stabilisation feature, the encapsulating liquid being immiscible with the carrier liquid, so that the discharged encapsulating liquid does not mix with the carrier liquid, floats on top of the carrier liquid, and is immobilised by the stabilisation feature; (3) draw a sample liquid from the sample-liquid input; and (4) discharge the drawn sample liquid, the sample liquid being immiscible with the encapsulating liquid and with the carrier liquid, so that the sample liquid does not mix with the encapsulating liquid or with the carrier liquid. Exemplary flowcharts are shown in FIGS. 43-47.

Figure 44:
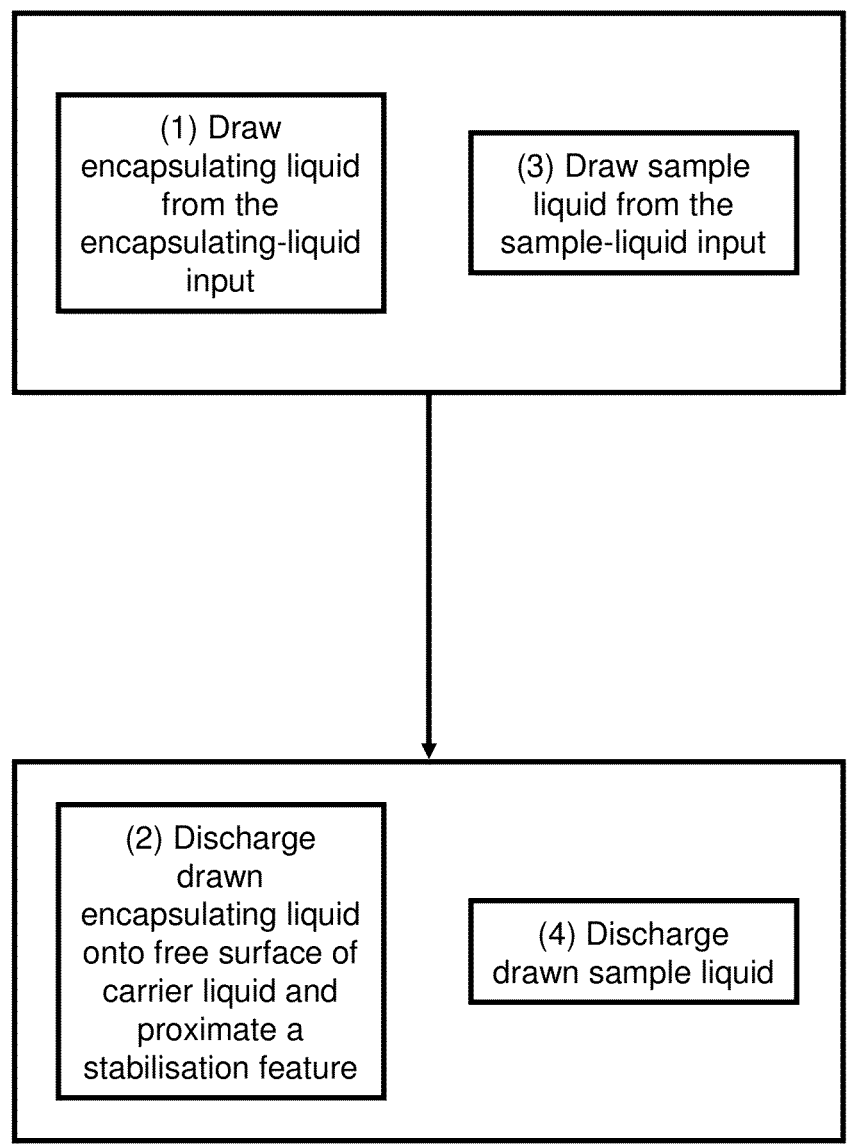
Figure 45:
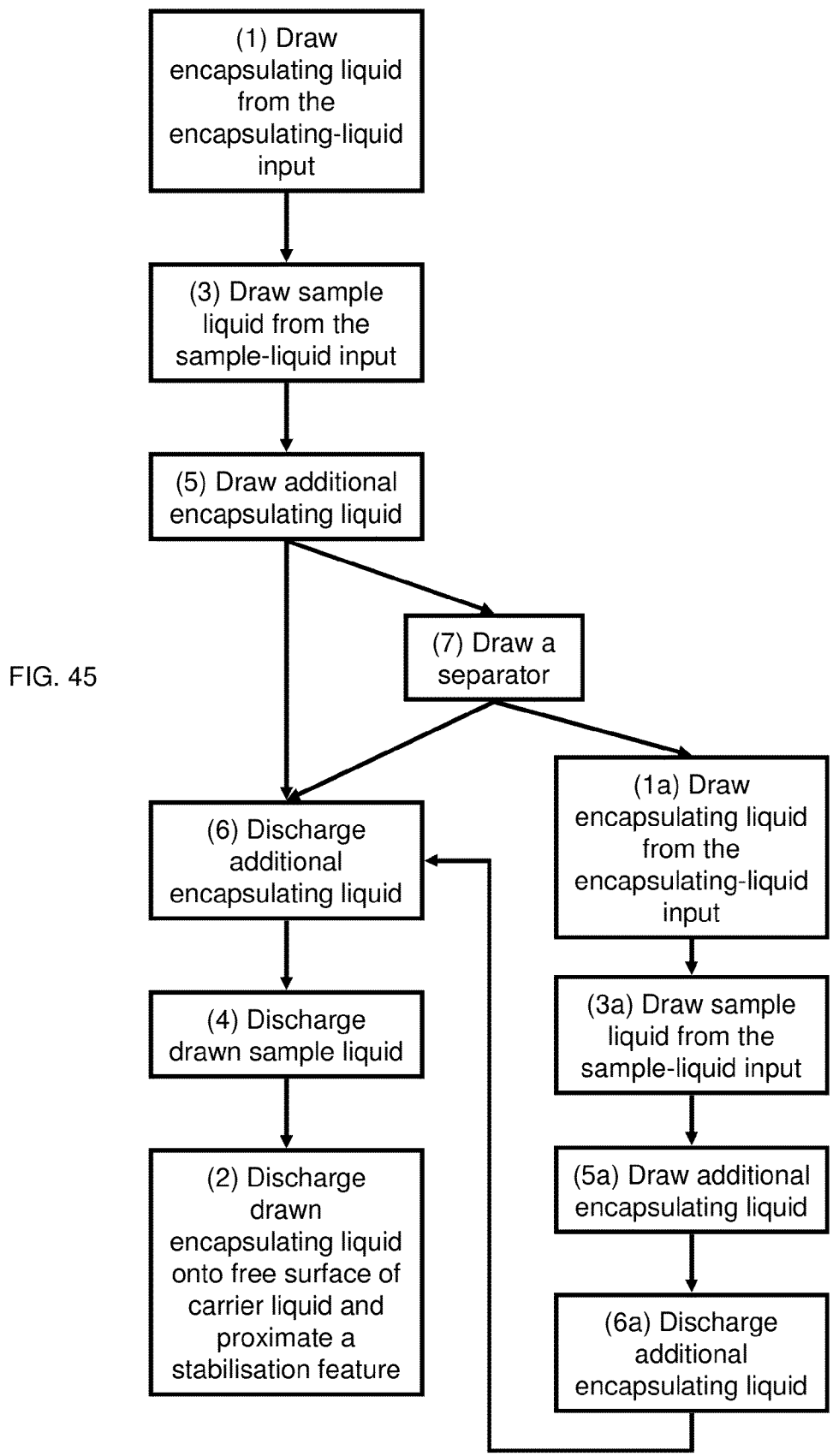

In some embodiments the liquid handling system comprises a control tube and a driver. In some embodiments the controller may be programmed to actuate the driver to cause the control tube to carry out steps (1) and (3) before carrying out steps (2) and (4) (FIG. 44). In some embodiments the controller may be programmed to actuate the driver to cause the control tube to carry out step (1), then step (3), then to (5) draw additional encapsulating liquid, then to (6) discharge the encapsulating liquid, then to carry out step (4), then step (2), so that the encapsulating liquid, the sample liquid, and the additional encapsulating liquid are discharged as a unit from the control tube and onto the free surface of the carrier liquid in the carrier-liquid conduit, the encapsulating liquid and the additional encapsulating liquid thereby merging and surrounding the sample liquid to form a composite liquid cell (FIG. 45). In some embodiments the controller may also be programmed to actuate the driver to cause the control tube, after step (5) and before step (6), to (7) draw a separator (FIG. 45). In some embodiments the separator may comprise air. In some embodiments the controller may be programmed to actuate the driver to cause the control tube, after step (7) and before step (6), to (1a) draw an encapsulating liquid from an encapsulating-liquid input, then (3a) draw a sample liquid from a sample-liquid input, then (5a) draw additional encapsulating liquid, then (6a) discharge the encapsulating liquid of steps (1a) and (5a) with the sample liquid of step (3a) as a second unit from the control tube and onto the free surface of the carrier liquid in the carrier-liquid conduit, the second unit thereby forming a second composite liquid cell (FIG. 45).

Figure 46:
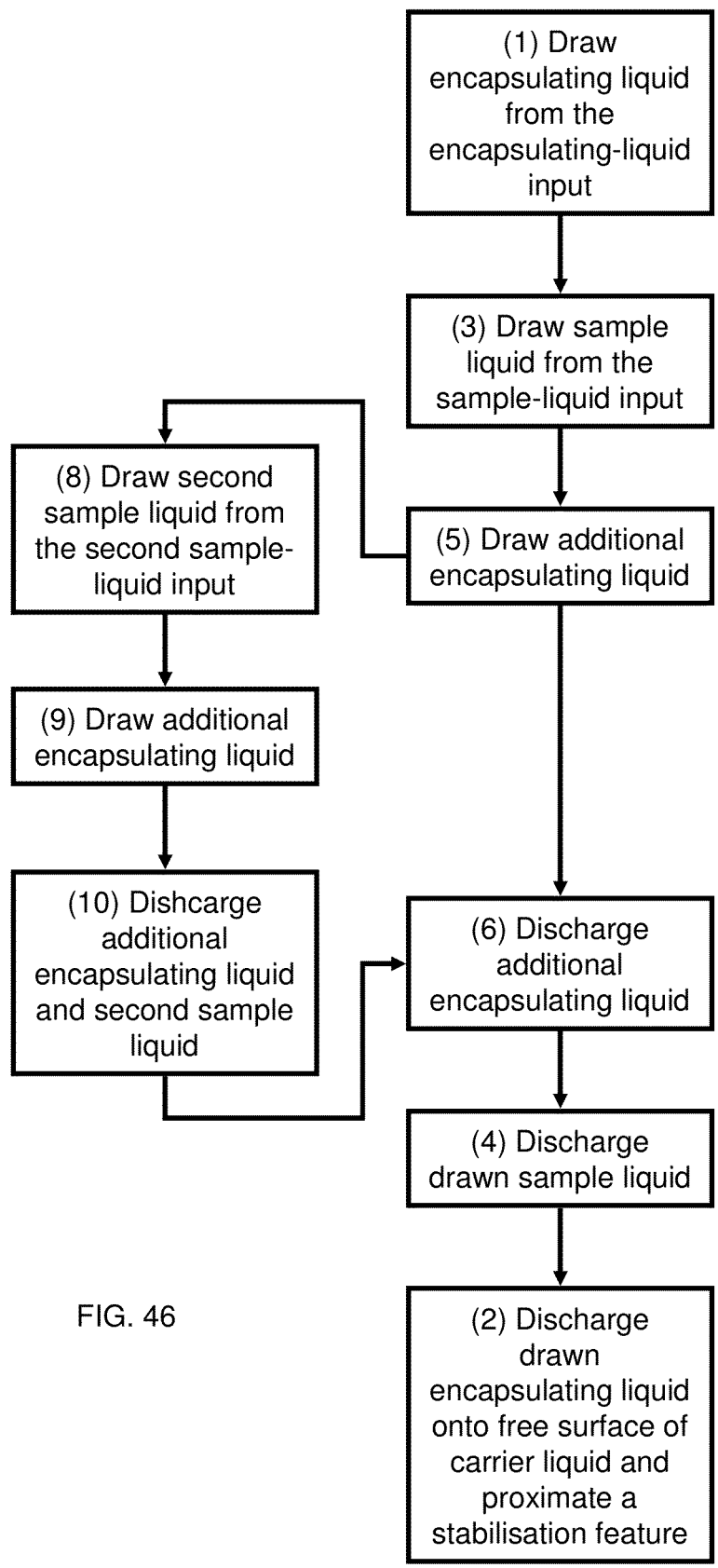

In some embodiments the controller is further programmed to actuate the driver to cause the control tube, after step (5) and before step (6), to (8) draw a second sample liquid from a second sample-liquid input, the second sample liquid being immiscible with the carrier liquid and the encapsulating liquid, then (9) draw additional encapsulating liquid, then (10) discharge the additional encapsulating liquid of step (9) and the second sample liquid into the unit, so that the composite liquid cell thereby formed comprises a droplet of the sample liquid and a droplet of the second sample liquid (FIG. 46).

Figure 47:
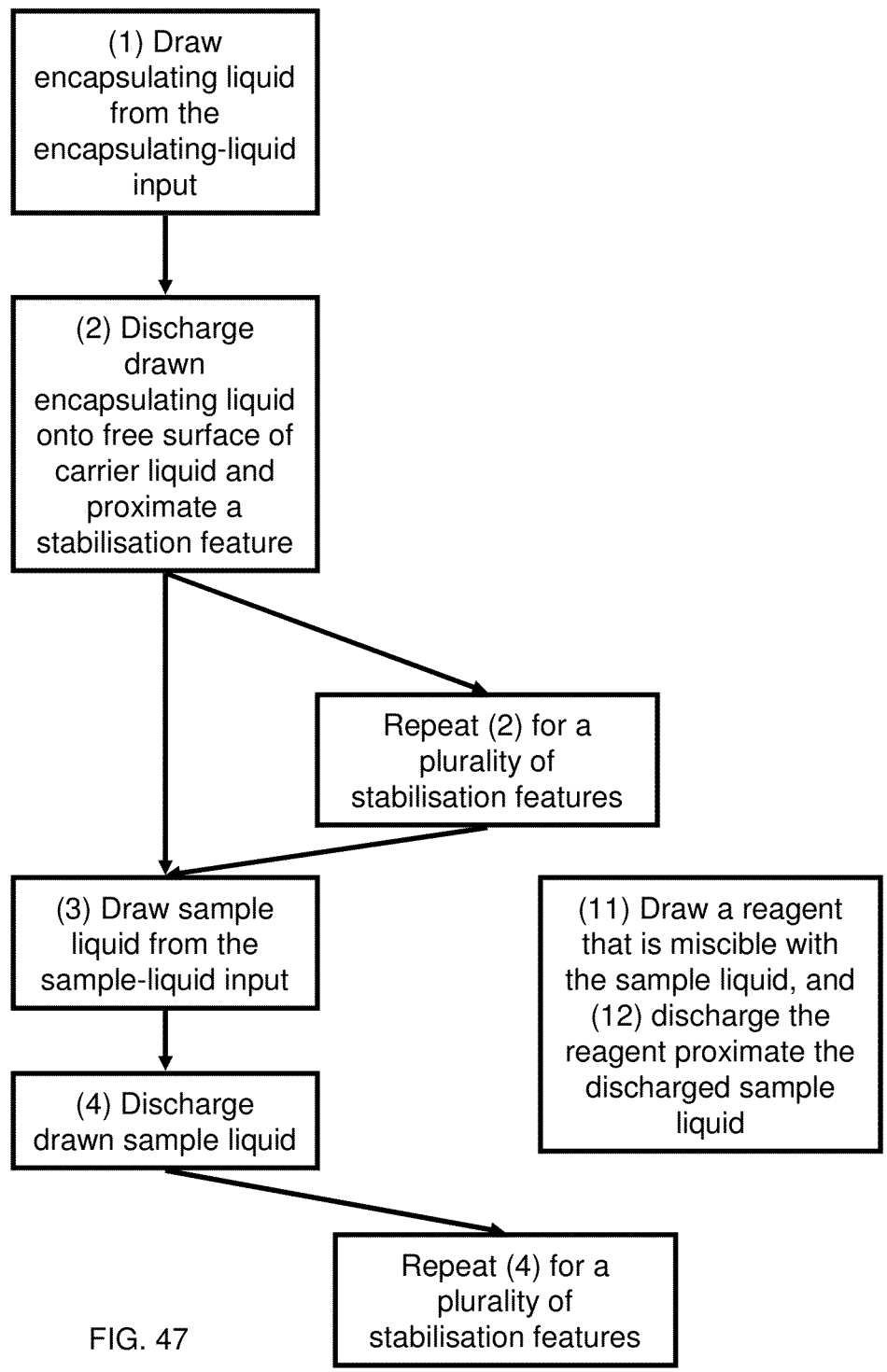

In some embodiments the liquid-handling system comprises a control tube and a driver, and the controller is programmed to actuate the driver to cause the control tube to carry out steps (1) through (4) in the order recited (FIG. 47). In some embodiments the controller may be programmed to perform step (1), then repeat step (2) for a plurality of stabilization features, then perform step (3), then repeat step (4) for the plurality of stabilization features, thereby forming a plurality of composite liquid cells distributed among the stabilization features (FIG. 47). In some embodiments the controller is further programmed to actuate the driver to cause the control tube to (11) draw a reagent that is miscible with the sample liquid, and (12) discharge the reagent proximate to the discharged sample liquid (FIG. 47). In some embodiments the sample handling system further comprises a motion system that translates at least a discharging portion of the liquid-handling system relative to the carrier-liquid conduit. In some embodiments the controller may be programmed to actuate the motion system to cause the control tube to move a composite liquid cell formed on the free surface of the carrier liquid relative to the carrier liquid conduit.

In some embodiments, (a) the carrier-liquid conduit comprises a bath sized to receive a disc rotatable therewithin upon a bath of carrier liquid; (b) the stabilisation feature is formed in the disc; (c) the system further comprises (1) a rotation driver operably coupled to the disc to cause it to rotate in the bath, and (2) a motion system that translates at least a discharging portion of the liquid-handling system vertically relative to the carrier-liquid conduit; and (d) the controller is operably connected to the rotation driver and to the motion system and is programmed to cause the rotation system to rotate the disc and to cause the motion system to translate the discharging portion of the liquid-handling system vertically relative to the disc.

In some embodiments the controller may be programmed to cause the liquid-handling system to discharge sufficient encapsulating liquid between two composite liquid cells, formed on the free surface of the carrier liquid and separated by a gap, liquid to bridge the gap, thereby causing the two composite liquid cells to merge with one another. In some embodiments the controller may be programmed to cause the liquid-handling system to discharge the sample liquid of step (4) proximate to the discharged encapsulating liquid.

In some embodiments the invention encompasses a sample handling method comprising drawing an encapsulating liquid from an encapsulating-liquid input; discharging the drawn encapsulating liquid (a) onto a free surface of a carrier liquid in a carrier-liquid conduit comprising a stabilisation feature and (b) proximate to the stabilisation feature, the encapsulating liquid being immiscible with the carrier liquid, so that the discharged encapsulating liquid does not mix with the carrier liquid, floats on top of the carrier liquid, and is immobilised by the stabilisation feature; drawing a sample liquid from a sample-liquid input; and discharging the drawn sample liquid, the sample liquid being immiscible with the encapsulating liquid and with the carrier liquid, so that the sample liquid does not mix with the encapsulating liquid or with the carrier liquid.

In some embodiments the invention encompasses a method for processing biological samples, the method comprising encapsulating a sample in an immiscible buffer fluid and moving them as a combined unit for sample handling.

In some embodiments, the sample, while encapsulated, is placed on or in a carrier fluid.

In some embodiments, the carrier fluid is a liquid and the sample is placed on the surface of the liquid, the carrier fluid being immiscible with the encapsulating buffer fluid.

In some embodiments, the carrier fluid has a higher density than the encapsulating buffer fluid.

In some embodiments, the encapsulating fluid is non-reactive with the target sample.

In another embodiment, there is a control surface which controls the motion of the encapsulating buffer fluid through electrostatic forces such as for introducing samples into the buffer fluid.

In some embodiments, there is a control surface which controls the motion of the encapsulating buffer fluid through surface tension forces such as for introducing samples into the buffer fluid.

In some embodiments, there are a plurality of controlling surfaces.

In some embodiments, the controlling surfaces include a dynamic surface.

In some embodiments, the controlling surfaces include a static surface.

In some embodiments, the controlling surfaces include a combination of dynamic and static surfaces.

In some embodiments, the controlling surfaces are submerged within the carrier fluid at some times.

In some embodiments, the controlling surfaces are on the carrier fluid interface.

In some embodiments, the controlling surfaces are above the carrier fluid.

In some embodiments, the carrier fluid flows.

In some embodiments, at least one analysis system performs analysis of the biological sample within the encapsulating buffer fluid on the carrier fluid.

In some embodiments, there is a plurality of analysis stages.

In some embodiments, the analysis includes thermal cycling the encapsulating buffer fluid.

In some embodiments, the buffer encapsulating fluid is a silicone-based oil or a fluorocarbon-based oil.

In some embodiments, the carrier fluid is a silicone-based oil or a fluorocarbon-based oil.

In some embodiments, the sample is a biological sample.

In some embodiments, the sample is an aqueous-based biological sample.

In some embodiments, the sample is a solid particle.

In some embodiments, the sample is an aqueous-in-oil emulsion.

In some embodiments, sample amplification is performed, and in some cases quantification of the amplification is performed.

In some embodiments, real time quantification of the amplification is performed.

In some embodiments, the method comprises forming a target sample encapsulated in an immiscible fluid volume and depositing it on a carrier fluid which is immiscible with the encapsulating buffer fluid; and controlling the encapsulated buffer fluid with electrostatic forces.

In some embodiments, the target sample is encapsulated in an immiscible fluid volume dispensed into a flowing carrier fluid.

In some embodiments, the encapsulated sample is dispensed into a static location.

In some embodiments, biological processing of the encapsulated sample is performed, and the encapsulated sample is combined with one or more encapsulated samples.

In some embodiments, genomic amplification is performed.

In some embodiments, the method comprises the step of controlling the encapsulating buffer fluid with surface tension forces.

In some embodiments, nucleic acid ligation is performed.

In another aspect, the invention provides a sample handling system comprising means for performing the steps of any method as defined herein.

In some embodiments, the system comprises: a conduit for continuous flow of the carrier fluid such as oil which carries the encapsulating fluid with the target sample; an analysis stage; and a controller to control the system.

In some embodiments, the system comprises a thermal cycling stage.

In some embodiments, the system is adapted to deposit the encapsulated into or onto a static position on a carrier fluid.

In some embodiments, herein there are a plurality of positions.

In some embodiments, there are a plurality of conduits.

In some embodiments, the system further comprises means for controlling movement of an encapsulated sample by electrostatic forces.

In some embodiments, the system is adapted to move an encapsulated sample onto or on a static carrier fluid.

In some embodiments, the sample is moved to any of a plurality of locations and there may be a plurality of samples on the static carrier fluid.

In some embodiments, a conduit is closed.

In some embodiments, the invention encompasses a method for processing samples, in some cases biological samples, the method comprising encapsulating two or more samples in an buffer fluid immiscibly with the samples and moving them as a combined unit.

In some embodiments the buffer fluid may be a liquid.

In some embodiments, two or more samples, while encapsulated, are placed on or in a carrier fluid.

In some embodiments, the sample is a multiplex reaction.

In some embodiments, two or more samples are encapsulated within the one encapsulant fluid surface.

In some embodiments, the carrier fluid is a liquid and the sample or samples, while encapsulated are placed on the surface of the liquid, the carrier fluid being immiscible with the encapsulating buffer fluid.

In some embodiments, the sample, while encapsulated, is combined with another sample, while encapsulated, resulting in two discrete samples, while encapsulated within one encapsulating surface.

In some embodiments, the sample, while encapsulated, will be processed for one or more targets.

In some embodiments, at least one analysis system performs analysis of one or more biological samples within the encapsulating buffer fluid, in some cases on the carrier fluid.

In some embodiments, the buffer encapsulating fluid has a additive added for sample stability.

In some embodiments, the buffer encapsulating fluid is a silicone-based oil with a polysorbate additive.

In some embodiments, the polysorbate additive is added in the range of 0.001% to 10%.

In some embodiments the buffer fluid includes an additive including a surfactant.

In some embodiments, the total hydrophilic-lipophilic balance number of the added surfactants are in a range of 2 to 8.

In some embodiments, the method comprises forming two or more target samples encapsulated in an immiscible fluid volume and depositing it on a carrier fluid which is immiscible with the encapsulating buffer fluid; and controlling the encapsulated buffer fluid with electrostatic forces.

In some embodiments, two or more target samples are encapsulated in an immiscible fluid volume dispensed into a flowing carrier fluid.

In some embodiments, at least one encapsulated sample is dispensed into a static location.

In some embodiments, biological processing of at least one encapsulated sample is performed, and at least encapsulated sample is combined with one or more other encapsulated samples.

In some embodiments a further sample may be added to the cell thereby arraying samples.

In some embodiments the samples are arrayed for optical detection.

In some embodiments the cell is transported by impingement of a gas from a directional outlet such as a tube.

In some embodiments, the invention provides a sample handling system comprising means for performing the steps of any method as defined above.

In some embodiments, the system comprises: a conduit for continuous flow of the carrier fluid such as oil which carries the encapsulating fluid with two or more target samples; an analysis stage; and a controller to control the system.

In some embodiments the system comprises: a conduit for flow of a buffer fluid such as oil with two or more target samples which is interfaced with a carrier fluid; an analysis stage; and a controller to control the system.

In some embodiments the system comprises: a moving hydrophobic spar on which a carrier fluid such as oil carries buffer fluid with two or more target samples; an analysis stage; and a controller to control the system.

In some embodiments, the carrier oil has a surfactant additive.

In some embodiments the invention is used for processing a sample, the sample being encapsulated in an immiscible buffer fluid and positioned at a hydrophobic control surface for sample handling.

In some embodiments, the hydrophobic control surface is stationary.

In some embodiments, the hydrophobic control surface is dynamic.

In some embodiments, the hydrophobic control surface is a fluoropolymer.

In some embodiments, there are a plurality of hydrophobic controlling surfaces.

In some embodiments, the controlling surface is electrostatically energised.

In some embodiments, the hydrophobic controlling surfaces include a combination of dynamic and static surfaces.

In some embodiments, the composite liquid cell is controlled by one or more hydrophobic controlling surfaces.

In some embodiments, the hydrophobic control surface is temperature controlled.

In some embodiments, the hydrophobic control surface is part of an optical detection system.

In some embodiments, the hydrophobic control surface has a marker for optical detection.

In some embodiments, the hydrophobic control surface has a radio frequency identification circuit.

In some embodiments, the hydrophobic control surface controls a plurality of composite liquid cells.

In some embodiments, the hydrophobic control surface has stabilisation features.

In some embodiments, there are a plurality of stabilisation features.

In some embodiments, the stabilisation features are pockets into the hydrophobic control surface.

In some embodiments, the stabilisation features are v shaped.

In some embodiments, the stabilisation features are circular shaped.

In some embodiments, the stabilisation features are tapered.

In some embodiments, the stabilisation features are used to locate the sample encapsulated in an immiscible buffer fluid on a mutually immiscible carrier fluid.

In some embodiments, the stabilisation features are arrayed to form a network.

In some embodiments, the network is used for mixing composite liquid cells.

In some embodiments, the network is used for transporting a composite liquid cell.

In some embodiments, the network comprises a static hydrophobic control surface.

In some embodiments, the network comprises a dynamic hydrophobic control surface.

In some embodiments, the network comprises a combination of static and dynamic control surfaces.

In some embodiments, real time quantification of proteins is performed.

In some embodiments, the encapsulated sample is dispensed, for example, into a static location.

In some embodiments, biological processing of the encapsulated sample is performed, and/or the encapsulated sample is combined with one or more encapsulated samples.

In some embodiments, the system comprises: a conduit for deposition of encapsulating fluid adjacent to a hydrophobic control surface with periodic target sample depositions; such that the hydrophobic control surface carries the encapsulating fluid with the target sample; an analysis stage; and a controller to control the system. The deposition may be continuous.

In some embodiments the invention provides methods and systems for generating, and/or transporting, and/or mixing, and/or processing biological samples. It achieves this by the formation of an immiscible fluid cell within which the biological sample (solid, liquid, emulsion of aqueous-in-oil or suspension of solid in immiscible liquid) may be manipulated. The method and system can generate, and/or transport, and/or mix, and/or process a range of volumes from microliter to sub-nanoliter volumes.

In some embodiments, the invention provides a method and/or a system for processing biological samples, comprising encapsulating two or more samples in a buffer fluid which is immiscible with the samples, to provide a multi-sample cell, and moving the cell as a combined unit for sample handling.

In some embodiments the method and system may generate non-contaminating microliter or nanoliter or sub-nanoliter volumes which can be controlled by a number of methods.

In some embodiments it generates one or more biological samples within an immiscible fluid cell and this composite liquid cell is then placed on a free surface of a mutually immiscible fluid, referred to as a carrier fluid.

The carrier fluid may provide a manipulation platform for the composite liquid cell. The composite liquid cell may be generated by collecting within a tube the composite components in the following sequence: immiscible fluid, biological sample (fluid, emulsion, solid or suspended particles), immiscible fluid, and in some cases air. This can be repeated for multiple composite liquid cells with the tube, or in some cases for one or more multi-sample composite liquid cells.

The contents of the tube may then be dispensed on the carrier fluid generating the composite liquid cells.

The method and system may generate non-contaminating nanoliter or sub-nanoliter volumes which can be controlled by a number of methods. The invention method provides for the composite liquid cell to be controlled by electrostatic forces.

In some embodiments the invention may have at least one electrically charged control surface which can control the composite liquid cell. The invention may provide an independent method of control through use of the hydrophobic effect.

In some embodiments the invention may have at least one control surface which has a hydrophobicity property which allows adhesion between it and the outer fluid of an immiscible fluid cell while repelling the internal fluid volume, preventing contamination. Using solid structures embedded or partly embedded in the carrier oil, the composite liquid cell can be guided in a controlled manner or anchored, increasing the dynamic control of the composite liquid cell.

In some embodiments the invention may provide transport of composite liquid cells in any of the methods outlined above. Mixing of the composite liquid cells in some embodiments involves transporting the composite liquid cells to contact, promoting fluid coalescence of the encapsulating oil and biological samples. This mixing process facilitates the combination of sub-microliter target volumes with great efficiency, prevents contamination from other sources and ensures no dead volume per chemistry manipulation. In some embodiments, the samples are not mixed, resulting in a multi-sample composite liquid cells.

In some embodiments the transport of composite liquid cells through a biological process is not susceptible to air, which leads to the evaporation of target volumes at elevated temperatures. The independent transport of each composite liquid cell within the system through the carrier oil reduces power consumption of the overall system that would otherwise be required for heating, cooling, or pumping of the carrier fluid, and instead the thermal protocol can be targeted at the composite liquid cell.

In some embodiments the invention allows for easy automation of the biochemistry processes. It allows for the dynamic control of individual samples, thereby allowing for full volume retrieval of samples. It allows for use in both an open or closed architecture manipulation platform. It allows for the analysis and manipulation of biological samples. The samples can be analysed easily by optical, acoustic, or electromagnetic methods.

Individual features of various embodiments disclosed herein may be combined as desired mutatis mutandis, to the extent they are not mutually exclusive to one another.

We claim:

1. A sample handling system comprising:
   a sample-liquid input;
   an encapsulating-liquid input;
   a carrier-liquid conduit;
   a liquid-handling system; and
   a controller operably connected to the liquid-handling system;
   wherein the controller is programmed to cause the liquid-handling system to:
   (1) draw an encapsulating liquid from the encapsulating-liquid input;
   (2) discharge the drawn encapsulating liquid onto a free surface of a carrier liquid in the carrier-liquid conduit, the encapsulating liquid being immiscible with the carrier liquid, so that the discharged encapsulating liquid does (a) not mix with the carrier liquid, and (b) floats on top of the carrier liquid;
   (3) draw a sample liquid from the sample-liquid input; and
   (4) discharge the drawn sample liquid, the sample liquid being immiscible with the encapsulating liquid and with the carrier liquid, so that the sample liquid does not mix with the encapsulating liquid or with the carrier liquid.

2. The system of claim 1, wherein the liquid-handling system comprises a control tube and a driver, and the controller is programmed to actuate the driver to cause the control tube to carry out steps (1) and (3) before carrying out steps (2) and (4).

3. The system of claim 2, wherein the controller is programmed to actuate the driver to cause the control tube to carry out step (1), then step (3), then to (5) draw additional encapsulating liquid, then to (6) discharge the encapsulating liquid, then to carry out step (4), then step (2), so that the encapsulating liquid, the sample liquid, and the additional encapsulating liquid are discharged as a unit from the control tube and onto the free surface of the carrier liquid in the carrier-liquid conduit, the encapsulating liquid and the additional encapsulating liquid thereby merging and surrounding the sample liquid to form a composite liquid cell.

4. The system of claim 3, wherein the controller is further programmed to actuate the driver to cause the control tube, after step (5) and before step (6), to (7) draw a separator.

5. The system of claim 4, wherein the separator comprises air.

6. The system of claim 4, wherein the controller is further programmed to actuate the driver to cause the control tube, after step (7) and before step (6), to (1a) draw an encapsulating liquid from an encapsulating-liquid input, then (3a) draw a sample liquid from a sample-liquid input, then (5a) draw additional encapsulating liquid, then (6a) discharge the encapsulating liquid of steps (1a) and (5a) with the sample liquid of step (3a) as a second unit from the control tube and onto the free surface of the carrier liquid in the carrier-liquid conduit, the second unit thereby forming a second composite liquid cell.

7. The system of claim 3, wherein the controller is further programmed to actuate the driver to cause the control tube, after step (5) and before step (6), to (8) draw a second sample liquid from a second sample-liquid input, the second sample liquid being immiscible with the carrier liquid and the encapsulating liquid, then (9) draw additional encapsulating liquid, then (10) discharge the additional encapsulating liquid of step (9) and the second sample liquid into the unit, so that the composite liquid cell thereby formed comprises a droplet of the sample liquid and a droplet of the second sample liquid.

8. The system of claim 1, wherein the liquid-handling system comprises a control tube and a driver, and the controller is programmed to actuate the driver to cause the control tube to carry out steps (1) through (4) in the order recited.

9. The system of claim 8, wherein the controller is programmed to perform step (1), then repeat step (2) at a plurality of predetermined locations, then perform step (3), then repeat step (4) at the plurality of predetermined locations, thereby forming a plurality of composite liquid cells distributed among the stabilization features.

10. The system of claim 8, wherein the controller is further programmed to actuate the driver to cause the control tube to (11) draw a reagent that is miscible with the sample liquid, and (12) discharge the reagent proximate to the discharged sample liquid.

11. The system of any preceding claim, further comprising a motion system that translates at least a discharging portion of the liquid-handling system relative to the carrier-liquid conduit.

12. The system of claim 11, wherein the controller is further programmed to actuate the motion system to cause the control tube to move a composite liquid cell formed on the free surface of the carrier liquid relative to the carrier liquid conduit.

13. The system of claim 1, wherein the controller is further programmed to cause the liquid-handling system to discharge sufficient encapsulating liquid between two composite liquid cells, formed on the free surface of the carrier liquid and separated by a gap, liquid to bridge the gap, thereby causing the two composite liquid cells to merge with one another.

14. The system of claim 1, wherein the controller is programmed to cause the liquid-handling system to discharge the sample liquid of step (4) proximate to the discharged encapsulating liquid.

15. The system of claim 1 wherein:
the carrier liquid conduit further comprises a plurality of stabilization features:
step (2) further comprises discharging the drawn encapsulating liquid proximate to one of the plurality of stabilization features; and
step (4) further comprises discharging the drawn sample liquid proximate to the same one of the plurality of stabilization features.

16. A sample handling method, comprising:
drawing an encapsulating liquid from an encapsulating-liquid input;
discharging the drawn encapsulating liquid (a) onto a free surface of a carrier liquid in a carrier-liquid conduit, the encapsulating liquid being immiscible with the carrier liquid, so that the discharged encapsulating liquid does not mix with the carrier liquid, and floats on top of the carrier liquid;
drawing a sample liquid from a sample-liquid input; and
discharging the drawn sample liquid, the sample liquid being immiscible with the encapsulating liquid and with the carrier liquid, so that the sample liquid does not mix with the encapsulating liquid or with the carrier liquid.

* * * * *